US012577327B2

(12) United States Patent
De Kruif

(10) Patent No.: US 12,577,327 B2
(45) Date of Patent: Mar. 17, 2026

(54) MIXED BINDING DOMAINS

(71) Applicant: Merus B.V., Utrecht (NL)

(72) Inventor: Cornelis Adriaan De Kruif, Utrecht (NL)

(73) Assignee: Merus B.V., Utrecht (NL)

( * ) Notice: Subject to any disclaimer, the term of this patent is extended or adjusted under 35 U.S.C. 154(b) by 1174 days.

(21) Appl. No.: 17/417,291

(22) PCT Filed: Dec. 27, 2019

(86) PCT No.: PCT/NL2019/050877
§ 371 (c)(1),
(2) Date: Jun. 22, 2021

(87) PCT Pub. No.: WO2020/141973
PCT Pub. Date: Jul. 9, 2020

(65) Prior Publication Data
US 2022/0073649 A1     Mar. 10, 2022

(30) Foreign Application Priority Data

Dec. 31, 2018     (EP) .................................... 18215995

(51) Int. Cl.
| | |
|---|---|
| *C07K 16/46* | (2006.01) |
| *A61K 39/00* | (2006.01) |
| *C07K 16/28* | (2006.01) |

(52) U.S. Cl.
CPC ........ C07K 16/461 (2013.01); C07K 16/2866 (2013.01); C07K 16/468 (2013.01); *A61K 2039/505* (2013.01); *C07K 2317/21* (2013.01); *C07K 2317/23* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | | |
|---|---|---|---|---|
| 6,680,376 | B2 | 1/2004 | Chiou | |
| 9,248,181 | B2 | 2/2016 | De Kruif et al. | |
| 9,358,286 | B2 | 6/2016 | De Kruif et al. | |
| 2010/0069262 | A1 | 3/2010 | Soegaard et al. | |
| 2014/0317765 | A1 * | 10/2014 | Leighton ............ | A01K 67/0275 800/19 |

FOREIGN PATENT DOCUMENTS

| | | | |
|---|---|---|---|
| AU | 784900 | B2 | 7/2006 |
| JP | 2001238676 | A | 9/2001 |
| JP | 2006241026 | A | 9/2006 |
| JP | 2006282521 | A | 10/2006 |
| WO | WO-9850431 | A2 | 11/1998 |
| WO | WO-0177342 | A1 | 10/2001 |
| WO | WO-2004009618 | A2 | 1/2004 |
| WO | WO-2007026689 | A1 | 3/2007 |
| WO | WO-2009126920 | A2 | 10/2009 |
| WO | WO-2009157771 | A2 * | 12/2009 | ......... A01K 67/0275 |
| WO | WO-2010135558 | A1 | 11/2010 |
| WO | WO-2010147171 | A1 | 12/2010 |
| WO | WO-2011084255 | A2 | 7/2011 |
| WO | WO-2012023053 | A2 | 2/2012 |
| WO | WO-2013033406 | A2 | 3/2013 |
| WO | WO-2013157953 | A1 | 10/2013 |
| WO | WO-2013157954 | A1 | 10/2013 |
| WO | WO-2014130690 | A1 * | 8/2014 | ......... A01K 67/0278 |
| WO | WO-2015186721 | A1 * | 12/2015 | ............ C07K 16/10 |
| WO | WO-2016105450 | A2 | 6/2016 |
| WO | WO-2017035274 | A1 | 3/2017 |
| WO | WO-2017069628 | A2 | 4/2017 |
| WO | WO-2018045110 | A1 | 3/2018 |
| WO | WO-2019190327 | A2 | 10/2019 |
| WO | WO-2020141973 | A1 | 7/2020 |

OTHER PUBLICATIONS

Chen, H., "Construction and identification of an immune single chain antibody library derived from a chicken," Chin J Cell Mol Immunol 23(7):645-648, Fourth Military Medical University, China (2007).
Adachi, K., et al., "Ostrich Produce Cross-reactive Neutralization Antibodies Against Pandemic Influenza Virus A/H1N1 Following Immunization With a Seasonal Influenza Vaccine," Experimental and Therapeutic Medicine 2(1):41-45, Spandidos Pub., Greece (Jan. 2011).
Andris-Widhopf, J., et al., "Methods for the Generation of Chicken Monoclonal Antibody Fragments by Phage Display," Journal of Immunological Methods 242(1-2):159-181, Elsevier, Netherlands (Aug. 2000).
Bins, A.D., et al., "A Rapid and Potent DNA Vaccination Strategy Defined by in Vivo Monitoring of Antigen Expression," Nature Medicine 11(8):899-904, Nature Publishing Company, United States (Aug. 2005).
Carnec, X., et al., "Anti-CXCR4 Monoclonal Antibodies Recognizing Overlapping Epitopes Differ Significantly in Their Ability To Inhibit Entry of Human Immunodeficiency Virus Type 1," Journal of Virology 79(3):1930-1933, American Society For Microbiology, United States (Feb. 2005).
Ching, K.H., et al., "Chickens With Humanized Immunoglobulin Genes Generate Antibodies With High Affinity and Broad Epitope Coverage to Conserved Targets," mAbs 10(1):71-80, Taylor & Francis, United States (Jan. 2018).
Chiou, V.Y.N., "The Development of IgY(DeltaFc) Antibody Based Neuro Toxin Antivenoms and the Study on Their Neutralization Efficacies," Clinical Toxicology 46(6):539-544, Informa Healthcare, England (Jul. 2008).

(Continued)

*Primary Examiner* — Daniel E Kolker
*Assistant Examiner* — Maureen Varina Driscoll
(74) *Attorney, Agent, or Firm* — Sterne, Kessler, Goldstein & Fox P.L.L.C.

(57) ABSTRACT

A binding domain or a multimer or a variant thereof which comprises a variable region encoded by a nucleic acid based on, derived or obtained from an animal phylogenetically distal from a human, which variable region is paired with a human variable region.

23 Claims, 33 Drawing Sheets
Specification includes a Sequence Listing.

(56)          References Cited

OTHER PUBLICATIONS

De Haard, H.J., et al., "A Large Non-immunized Human Fab Fragment Phage Library That Permits Rapid Isolation and Kinetic Analysis of High Affinity Antibodies," Journal of Biological Chemistry 274(26):18218-18230, American Society for Biochemistry and Molecular Biology, United States (Jun. 1999).

De Meulenaer, B. and Huyghebaert, A., "Isolation and Purification of Chicken Egg Yolk Immunoglobulins: A Review," Food and Agricultural Immunology 13(4):275-288, Taylor & Francis Ltd, England (Dec. 2001).

Digiammarino, E. L., et al., "Ligand Association Rates to the Inner-variable-domain of a Dual-variable-domain Immunoglobulin Are Significantly Impacted by Linker Design," mAbs 3(5):487-494, Taylor & Francis, United States (2011), XP009168882.

Genovis/Lance Leve, "Smart Enzymes," Jan. 1, 2015, 18 pages, accessed at [http://www.chayon.co.kr/wp-content/uploads/2018/04/Genovis_Proteases-1.pdf].

Ha, J.H., et al., "Immunoglobulin Fc Heterodimer Platform Technology: From Design to Applications in Therapeutic Antibodies and Proteins," Frontiers in Immunology 7:394, Frontiers Research Foundation, Switzerland (Oct. 2016), XP055377975.

Harris, K. E., et al., "Sequence-Based Discovery Demonstrates That Fixed Light Chain Human Transgenic Rats Produce a Diverse Repertoire of Antigen-Specific Antibodies," Frontiers in Immunology 9:889, Frontiers Research Foundation, Switzerland (Apr. 2018). XP055682908.

Hoogenboom, H.R., "Selecting and Screening Recombinant Antibody Libraries," Nature Biotechnology 23(9):1105-1116, Nature America Publishing, United States (2005).

International Search Report and Written Opinion for International Application No. PCT/NL2019/050877, European Patent Office, Netherlands, mailed on Mar. 12, 2020.

Wu, L., et al., "Fundamental Characteristics of the Immunoglobulin VH Repertoire of Chickens in Comparison With Those of Humans, Mice, and Camelids," Journal of Immunology 188(1):322-333, American Association of Immunologists, United States (Jan. 2012).

Kontermann, R.E., "Dual Targeting Strategies with Bispecific Antibodies," mAbs 4(2):182-197, Taylor and Francis, United States (2012), XP055566203.

Krah, S., et al., "Generation of Human Bispecific Common Light Chain Antibodies by Combining Animal Immunization and Yeast Display," Protein Engineering, Design & Selection 30(4):291-301, Oxford University Press, England(Apr. 2017), XP055690141.

Kramer, R.A., et al., "A Novel Helper Phage That Improves Phage Display Selection Efficiency by Preventing the Amplification of Phages Without Recombinant Protein," Nucleic Acids Research 31(11):e59, Oxford University Press, England (Jun. 2003).

Marks, J.D., et al., "By-passing Immunization. Human Antibodies from V-gene Libraries Displayed on Phage," Journal of Molecular Biology 222(3):581-597, Academic Press Limited, United States (Dec. 1991).

Morrison, S.L., "Two Heads Are Better Than One," Nature Biotechnology 25(11):1233-1234, Nature America Publishing, United States (Nov. 2007).

Pettinello, R. and Dooley, H., "The Immunoglobulins of Cold-Blooded Vertebrates," Biomolecules 4(4):1045-1069, MDPI, Switzerland (Nov. 2014).

Pokorna, D. et al. "DNA-vaccination via tattooing induces stronger humoral and cellular immune response than intramuscular delivery supported by molecular adjuvants," Genet Vaccines Ther., vol. 6(4):198-208 (2008).

Reynaud, C.A., et al., "A Hyperconversion Mechanism Generates the Chicken Light Chain Preimmune Repertoire," Cell 48(3):379-388, Cell Press, United States (Feb. 1987).

Reynaud, C.A., et al., "A Single Rearrangement Event Generates Most of the Chicken Immunoglobulin Light Chain Diversity," Cell 40(2):283-291, Cell Press, United States (Feb. 1985).

Reynaud, C.A., et al., "Somatic Hyperconversion Diversifies the Single Vh Gene of the Chicken With a High Incidence in the D Region," Cell 59(1):171-183, Cell Press, United States (Oct. 1989).

Roth, L., et al., "Facile Generation of Antibody Heavy and Light Chain Diversities for Yeast Surface Display by Golden Gate Cloning," Biological Chemistry 400(3):383-393, Walter De Gruyter, Germany (Feb. 2019).

Schade, R. and Staak, C., "The Production of Avian (Egg Yolk) Antibodies: IgY: The Report and Recommendations of ECVAM Workshop 21," Alternatives to Laboratory Animals 24(6):925-934, SAGE Journals, United States (Nov. 1996).

Schade, R., et al., "Chicken Egg Yolk Antibodies (IgY-technology): A Review of Progress in Production and Use in Research and Human and Veterinary Medicine," Alternatives to Laboratory Animals 33(2):129-154, SAGE Publications, England (Apr. 2005).

Shih, H.H., et al., "An Ultra-specific Avian Antibody to Phosphorylated Tau Protein Reveals a Unique Mechanism for Phosphoepitope Recognition," The Journal of Biological Chemistry 287(53):44425-44434, Elsevier Inc., United States (Dec. 2012).

Thompson, J.D., et al., "CLUSTAL W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, England (Nov. 1994).

Witkowski, P.T., et al., "Gene Gun-supported DNA Immunisation of Chicken for Straightforward Production of Poxvirus-specific IgY Antibodies," Journal of Immunological Methods 341(1-2):146-153, Elsevier, Netherlands (Feb. 2009).

Geuijen, C., et al., "Unbiased Combinatorial Screening Identifies a Bispecific IgG1 that Potently Inhibits HER3 Signaling via HER2-Guided Ligand Blockade," Cancer Cell 33(5):922-936, CellPress, United States (2018).

Lundqvist, M.L., et al., "Immunoglobulins of the non-galliform birds: antibody expression and repertoire in the duck," Dev Comp Immunol 30(1-2):93-100, Elsevier, Netherlands (Jan. 2006).

* cited by examiner

```
                                     -----                   ---------------
chVH1     AVTLDESGGGLQTPGRSLSLVCKASGFTFSSYNMGWVRQAPGKGLESVSSIDNSGRYTGYSSVKGRATIS
huVH1-02  QVQLVQSGAENKKPGASVKVSCKASGNTFSYYMHWVRQAPGSGLEWMGWINPNSGGTNYAQSSGRVTM
                                                            ---
chVH1     RDNGQSTSRLQSNNLRAEDTSTYYCAKAAG
huVH1-02  RDTSISTAYMSSSRLRSDDTAVYYCARR---
```

Fig. 2

```
              ---------
     chJH  --TAGSSDAWGSGTEVIVSS
huIGHJ1  ---AEYSSHWGSGTLVIVSS
huIGHJ2  ---YWYFDLWGSGTLVTVSS
huIGHJ3  -----DAFDIWGSGTMVTVSS
huIGHJ4  ------YFDYWGSGTLVTVSS
huIGHJ5  ----NWFDPWGSGTLVTVSS
huIGHJ6  YYYYYSDVWGSGTTVTVSS
```

Fig. 3

|  | Hybrid Chicken | MF3178 | Identical | Equivalent |
|---|---|---|---|---|
| Total | 24 | 20 | 7 | 5 |
| Hydrogen Bond | 12 | 7 | 1 | 4 |
| Hydrophobic | 12 | 13 | 6 | 1 |

| # | Hybrid chicken (chicken VH-human VL) | MF3178 (human VH-human VL) | Category | Identical | Equivalent |
|---|---|---|---|---|---|
| 1 | A:ASN34:HD21 - B:GLY100H:O | A:ASN34:ND2 - B:TYR100D:O | Hydrogen Bond |  | * |
| 2 | A:ASN34:HD22 - B:ALA100G:O |  | Hydrogen Bond |  |  |
| 3 | A:TYR36:HH - B:GLY100H:O | A:TYR36:OH - B:PHE100G | Hydrogen Bond |  | * |
| 4 | A:GLN38:HE21 - B:TYR91:OH |  | Hydrogen Bond |  |  |
| 5 | A:GLN38:HE22 - B:GLN39:OE1 | A:GLN38:NE2 - B:GLN39:OE1 | Hydrogen Bond | * |  |
| 6 | A:LEU46:HA - B:ILE100J:O |  | Hydrogen Bond |  |  |
| 7 | A:GLN89:HE22 - B:GLY100H:O | A:GLN89:NE2 - B:TRP100E:O | Hydrogen Bond |  | * |
|  |  | A:GLN89:NE2 - B:PHE100G | Hydrogen Bond |  |  |
| 8 | A:SER91:HG - B:ALA100G:O |  | Hydrogen Bond |  |  |
| 9 | A:SER91:HB1 - B:ALA100G:O | B:GLN39:NE2 - A:GLN38:OE1 | Hydrogen Bond |  |  |
| 10 | B:ILE100J:HN - A:TYR36:OH | B:PHE100G:N - A:TYR36:OH | Hydrogen Bond |  | * |
| 11 | B:CYS100I:HA - A:TYR36:OH |  | Hydrogen Bond |  |  |
| 12 | B:TRP103:HD1 - A:PRO44:O |  | Hydrogen Bond |  |  |
|  |  | A:TYR32 - B:TYR100D | Hydrophobic |  |  |
|  |  | A:PRO44 - B:LEU45 | Hydrophobic |  |  |
| 13 | A:TYR49 - B:CYS100I |  | Hydrophobic |  |  |
|  |  | A:ALA50:CB - B:TYR100D | Hydrophobic |  |  |
| 14 | A:TYR87 - B:LEU45 | A:TYR87 - B:LEU45 | Hydrophobic | * |  |
| 15 | A:PHE98 - B:VAL37 |  | Hydrophobic |  |  |
| 16 | A:PHE98 - B:LEU45 |  | Hydrophobic |  |  |
|  |  | B:LEU45:CD1 - A:PHE98 | Hydrophobic |  |  |
| 17 | B:TRP47 - A:PRO96 | B:TRP47 - A:PRO96 | Hydrophobic | * |  |
| 18 | B:TRP47 - A:PRO96 | B:TRP47 - A:PRO96 | Hydrophobic | * |  |
| 19 | B:TYR91 - A:ALA43 | B:TYR91 - A:ALA43 | Hydrophobic | * |  |
| 20 | B:ALA96 - A:LEU46 | B:HIS96 - A:TYR49 | Hydrophobic |  | * |
| 21 | B:CYS100I - A:LEU46 | B:TRP100E - A:PRO96 | Hydrophobic |  |  |
| 22 | B:TRP103 - A:ALA43 | B:TRP103 - A:ALA43 | Hydrophobic |  |  |
| 23 | B:TRP103 - A:PRO44 | B:TRP103 - A:PRO44 | Hydrophobic | * |  |
| 24 | B:TRP103 - A:PRO44 | B:TRP103 - A:PRO44 | Hydrophobic | * |  |

Fig. 4a

|  | Hybrid Ostrich | MF3178 | Identical | Equivalent |
|---|---|---|---|---|
| Total | 14 | 20 | 7 | 1 |
| HBond | 6 | 7 | 2 | 1 |
| Hydrophobic | 8 | 13 | 5 | 0 |

| # | Hybrid Ostrich | MF3178 | Category | Identical | Equivalent |
|---|---|---|---|---|---|
|  |  | A:ASN34:ND2 - B:TYR100D:O | Hydrogen Bond |  |  |
| 1 | A:TYR36:HH - B:ASN100F:OD1 | A:TYR36:OH - B:PHE100G | Hydrogen Bond |  | * |
| 2 | A:GLN38:HE21 - B:GLN39:OE1 | A:GLN38:NE2 - B:GLN39:OE1 | Hydrogen Bond | * |  |
| 3 | A:TYR87:HH - B:GLN39:OE1 |  | Hydrogen Bond |  |  |
|  |  | A:GLN89:NE2 - B:TRP100E:O | Hydrogen Bond |  |  |
|  |  | A:GLN89:NE2 - B:PHE100G | Hydrogen Bond |  |  |
| 4 | A:SER91:HB1 - B:PRO100D:O |  | Hydrogen Bond |  |  |
| 5 | A:SER91:HB2 - B:PRO100D:O |  | Hydrogen Bond |  |  |
| 6 | B:GLN39:HE21 - A:GLN38:OE1 | B:GLN39:NE2 - A:GLN38:OE1 | Hydrogen Bond | * |  |
|  |  | B:PHE100G:N - A:TYR36:OH | Hydrogen Bond |  |  |
|  |  | A:TYR32 - B:TYR100D | Hydrophobic |  |  |
|  |  | A:PRO44 - B:LEU45 | Hydrophobic |  |  |
|  |  | A:ALA50:CB - B:TYR100D | Hydrophobic |  |  |
| 7 | A:TYR87 - B:LEU45 | A:TYR87 - B:LEU45 | Hydrophobic | * |  |
| 8 | A:PRO96 - B:PRO47 |  | Hydrophobic |  |  |
| 9 | A:PHE98 - B:LEU45 |  | Hydrophobic |  |  |
|  |  | B:LEU45:CD1 - A:PHE98 | Hydrophobic |  |  |
|  |  | B:TRP47 - A:PRO96 | Hydrophobic |  |  |
|  |  | B:TRP47 - A:PRO96 | Hydrophobic |  |  |
| 10 | B:TYR91 - A:ALA43 | B:TYR91 - A:ALA43 | Hydrophobic | * |  |
|  |  | B:HIS96 - A:TYR49 | Hydrophobic |  |  |
|  |  | B:TRP100E - A:PRO96 | Hydrophobic |  |  |
| 11 | B:TRP103 - A:ALA43 | B:TRP103 - A:ALA43 | Hydrophobic | * |  |
| 12 | B:TRP103 - A:PRO44 | B:TRP103 - A:PRO44 | Hydrophobic | * |  |
| 13 | B:TRP103 - A:ALA43 |  | Hydrophobic |  |  |
| 14 | B:TRP103 - A:PRO44 | B:TRP103 - A:PRO44 | Hydrophobic | * |  |

Fig. 7a

Ostrich VH

Human VL

CH1

CL

VH cLC

|  | Hybrid Duck | MF3178 | Identical | Equivalent |
|---|---|---|---|---|
| Total | 28 | 20 | 12 | 1 |
| HBond | 12 | 7 | 3 | 0 |
| Hydrophobic | 15 | 13 | 9 | 0 |
| Electrostatic | 1 | 0 | 0 | 0 |

Fig. 10a

| # | Hybrid Duck | MF3178 | Category | Identical | Equivalent |
|---|---|---|---|---|---|
| | | A:ASN34:ND2 - B:TYR100D:O | Hydrogen Bond | | |
| 1 | A:TYR36:HH - B:ALA100H:O | A:TYR36:OH - B:PHE100G | Hydrogen Bond | | * |
| 2 | A:GLN38:HE21 - B:GLN39:OE1 | A:GLN38:NE2 - B:GLN39:OE1 | Hydrogen Bond | * | |
| 3 | A:TYR87:HH - B:GLN39:OE1 | | Hydrogen Bond | | |
| 4 | A:TYR87:HH - B:LYS43:O | | Hydrogen Bond | | |
| | | A:GLN89:NE2 - B:TRP100E:O | Hydrogen Bond | | |
| | | A:GLN89:NE2 - B:PHE100G | Hydrogen Bond | | |
| 5 | A:GLN89:HE21 - B:ALA100H:O | | | | |
| 6 | A:SER91:HB2 - B:TYR100D:O | | Hydrogen Bond | | |
| 7 | B:GLN39:HE21 - A:GLN38:OE1 | B:GLN39:NE2 - A:GLN38:OE1 | Hydrogen Bond | * | |
| 8 | B:GLY44:HA2 - A:TYR87:OH | | Hydrogen Bond | | |
| 9 | B:GLY100E:HA1 - A:SER91:O | | Hydrogen Bond | | |
| 10 | B:GLY100E:HA2 - A:SER91:O | | Hydrogen Bond | | |
| 11 | B:ASP100I:HA - A:TYR36:OH | B:PHE100G:N - A:TYR36:OH | Hydrogen Bond | * | |
| 12 | B:ILE100J:HN - A:TYR36:OH | | Hydrogen Bond | | |
| 13 | B:ASP100I:OD1 - A:TYR49 | | Electrostatic | | |
| 14 | A:TYR32 - B:TYR100D | A:TYR32 - B:TYR100D | Hydrophobic | * | |
| 15 | A:PRO44:C,O;LYS45:N - B:TRP103 | | Hydrophobic | | |
| 16 | A:PRO44:C,O;LYS45:N - B:TRP103 | | Hydrophobic | | |
| 17 | A:PRO44 - B:LEU45 | A:PRO44 - B:LEU45 | Hydrophobic | * | |
| | | A:ALA50:CB - B:TYR100D | Hydrophobic | | |
| 18 | A:TYR87 - B:LEU45 | A:TYR87 - B:LEU45 | Hydrophobic | * | |
| 19 | A:PHE98 - B:LEU45 | | Hydrophobic | | |
| | | B:LEU45:CD1 - A:PHE98 | Hydrophobic | | |
| 20 | B:TRP47 - A:PRO96 | B:TRP47 - A:PRO96 | Hydrophobic | * | |
| 21 | B:TRP47 - A:PRO95 | | Hydrophobic | | |
| 22 | B:TRP47 - A:PRO96 | B:TRP47 - A:PRO96 | Hydrophobic | * | |
| 23 | B:TYR91 - A:ALA43 | B:TYR91 - A:ALA43 | Hydrophobic | * | |
| | | B:HIS96 - A:TYR49 | Hydrophobic | | |
| 24 | B:ALA100H - A:PRO96 | | Hydrophobic | | |
| | | B:TRP100E - A:PRO96 | Hydrophobic | | |
| 25 | B:TYR100D - A:ALA50 | | Hydrophobic | | |
| 26 | B:TRP103 - A:ALA43 | B:TRP103 - A:ALA43 | Hydrophobic | * | |
| 27 | B:TRP103 - A:PRO44 | B:TRP103 - A:PRO44 | Hydrophobic | * | |
| 28 | B:TRP103 - A:PRO44 | B:TRP103 - A:PRO44 | Hydrophobic | * | |

Fig. 10a continued

```
  1 GTTGGATGGC CAAAAAACGG TTGTTTTTTT TTTTTTTTAA CCAAAATGGG CGGTTTTCGC CCGAAAAGAG
                                                                     JH
                                                         ~~~~~~~~~~~~~~~~~~~~~~~~~~
                                                          T   A   G   S   I   D   A   W
 71 TGGGTGGAGT TTTTGGGTGA AAAAAGGCGG ATTTTGGGGC ATTGTGGTAC TGCTGGTAGC ATCGACGCAT
               JH
    ~~~~~~~~~~~~~~~~~~~~~~~~~~~~~~~~~~~~~~
      G   H   G   T   E   V   I   V   S   S
141 GGGGCCACGG GACCGAAGTC ATCGTCTCCT CCGGTGAGTC TTCAACCCCC CCCAAAATTG CCGCGGCGAT
211 TTTGG
```

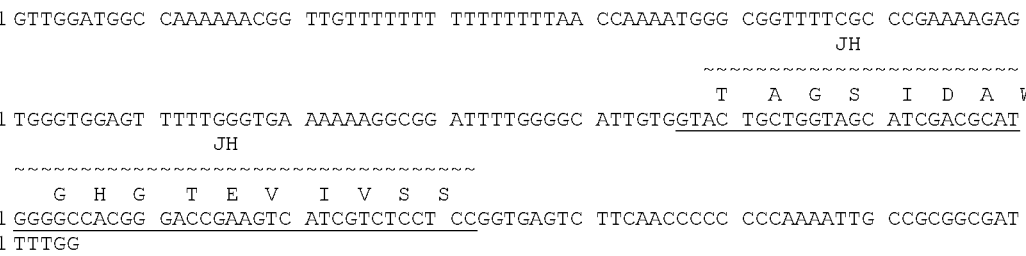

Fig. 12

```
                         SfiI
                ~~~~~~~~~~~~~~~~~~~~
    V   L   A   T   A   A   Q   P   A   M   A   A   V   T   L   D   E   S
  1 GTC CTC GCA ACT GCG GCC CAG CCG GCC ATG GCC GCC GTC ACT TTG GAC GAG TCC
```

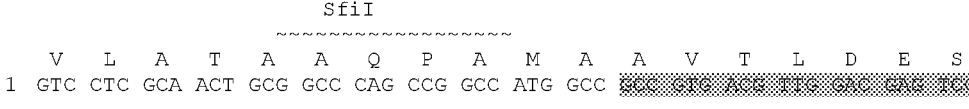

Fig. 13

```
                         SfiI
                ~~~~~~~~~~~~~
       MV1511 GGATTGTTATTACTCGCGGCCCAGCCGGCCATGGCGATGCCTGCTTGCCGAATATCATGGTGG
      chVH-FW ---GTCCTCGCAACTGCGGCCCAGCCGGCCATGGCCGCCGTGACGTTGGACGAGTCC------
M30319-chickenVH1 CAGCGCTCTCTGTCCTTCCCCACAGGGCTGATGGCGGCCGTGACGTTGGACGAGTCCGGGGGC
```

Fig. 14

```
                               BstEII
                               ~~~~~~~~~~
             G    T    E    V    T    V    S    S
          1  GGG  ACC  GAG  GTC  ACC  GTC  TCC  TCC
```

Fig. 15

```
                                            BstEII
                                            ~~~~~~
        MV1511  AAGTACGCCCCCTATTGACGTCAATGACGGTCACCGTCTCGAGCGCCTCCACCAAGGGCCCAT
     chVH-RV rc  -------------------GGGACCGAGGTCACCGTCTCCTCC------------------
M30320-chickenJH  GCATCGACGCATGGGGCCACGGGACCGAAGTCATCGTCTCCTCCGGTGAGTCTTCAACCCCCC
```

Fig. 16

Figure 17A (SEQ ID NO: 5)

DIQMTQSPSSLSASVGDRVTITCRASQSISSYLNWYQQKPGKAPKLLIYAASSLQSGVPSRFSGS
GSGTDFTLTISSLQPEDFATYYCQQSYSTPPTFGQGTKVEIKRTVAAPSVFIFPPSDEQLKSGTA
SVVCLLNNFYPREAKVQWKVDNALQSGNSQESVTEQDSKDSTYSLSSTLTLSKADYEKHKVYACE
VTHQGLSSPVTKSFNRGEC

Figure 17B (SEQ ID NOs: 6 and 7)

gacatccagatgacccagtctccatcctccctgtctgcatctgtaggagacagagtcacc
 D   I   Q   M   T   Q   S   P   S   S   L   S   A   S   V   G   D   R   V   T
atcacttgccgggcaagtcagagcattagcagctacttaaattggtatcagcagaaacca
 I   T   C   R   A   S   Q   S   I   S   S   Y   L   N   W   Y   Q   Q   K   P
gggaaagcccctaagctcctgatctatgctgcatccagtttgcaaagtggggtcccatca
 G   K   A   P   K   L   L   I   Y   A   A   S   S   L   Q   S   G   V   P   S
aggttcagtggcagtggatctgggacagatttcactctcaccatcagcagtctgcaacct
 R   F   S   G   S   G   S   G   T   D   F   T   L   T   I   S   S   L   Q   P
gaagattttgcaacttactactgtcaacagagttacagtacccctccaacgttcggccaa
 E   D   F   A   T   Y   Y   C   Q   Q   S   Y   S   T   P   P   T   F   G   Q
gggaccaaggtggagatcaaa
 G   T   K   V   E   I   K

Figure 17C (SEQ ID NOs: 8 and 9)

```
cgaactgtggctgcaccatctgtcttcatcttcccgccatctgatgagcagttgaaatct
 R   T   V   A   A   P   S   V   F   I   F   P   P   S   D   E   Q   L   K   S
ggaactgcctctgttgtgtgcctgctgaataacttctatcccagagaggccaaagtacag
 G   T   A   S   V   V   C   L   L   N   N   F   Y   P   R   E   A   K   V   Q
tggaaggtggataacgccctccaatcgggtaactcccaggagagtgtcacagagcaggac
 W   K   V   D   N   A   L   Q   S   G   N   S   Q   E   S   V   T   E   Q   D
agcaaggacagcacctacagcctcagcagcaccctgacgctgagcaaagcagactacgag
 S   K   D   S   T   Y   S   L   S   S   T   L   T   L   S   K   A   D   Y   E
aaacacaaagtctacgcctgcgaagtcacccatcagggcctgagctcgcccgtcacaaag
 K   H   K   V   Y   A   C   E   V   T   H   Q   G   L   S   S   P   V   T   K
agcttcaacagggggagagtgttag
 S   F   N   R   G   E   C   -
```

Figure 17D (SEQ ID NO: 10)

```
DIQMTQSPSSLSASVGDRVTITCRASQSISSYLNWYQQKPGKAPKLLIYAASSLQSGVPSRFSGS
GSGTDFTLTISSLQPEDFATYYCQQSYSTPPITFGQGTRLEIK
```

Figure 17E (SEQ ID NO: 11)

```
DIQMTQSPSSLSASVGDRVTITCRASQSISSYLNWYQQKPGKAPKLLIYAASSLQSGVPSRFSGS
GSGTDFTLTISSLQPEDFATYYCQQSYSTP
```

Figure 19A (SEQ ID NO: 87) IgVκ3-15/IGJκ1

EIVMTQSPATLSVSPGERATLSCRASQSVSSNLAWYQQKPGQAPRLLIYGASTRATGIPARFSGS
GSGTEFTLTISSLQSEDFAVYYCQQYNNWPWTFGQGTKVEIK

Figure 19B (SEQ ID NO: 88) IgVκ3-20/IGJκ1

EIVLTQSPGTLSLSPGERATLSCRASQSVSSSYLAWYQQKPGQAPRLLIYGASSRATGIPDRFSG
SGSGTDFTLTISRLEPEDFAVYYCQQYGSSPWTFGQGTKVEIK

Figure 19C (SEQ ID NO: 89) IgVλ3-21/IGJλ3

SYVLTQPPSVSVAPGETARITCGGDNIGRKSVYWYQQKSGQAPVLVIYYDSDRPSGIPERFSGSN
SGNTATLTISRVEAGDEADYYCQVWDGSSDHWVFGGGTKLTVL

Figure 19D (SEQ ID NO: 90) IgVκ3-15

EIVMTQSPATLSVSPGERATLSCRASQSVSSNLAWYQQKPGQAPRLLIYGASTRATGIPARFSGS
GSGTEFTLTISSLQSEDFAVYYCQQYNNWP

Figure 19E (SEQ ID NO: 91) IgVκ3-20

EIVLTQSPGTLSLSPGERATLSCRASQSVSSSYLAWYQQKPGQAPRLLIYGASSRATGIPDRFSG
SGSGTDFTLTISRLEPEDFAVYYCQQYGSSP

Figure 19F (SEQ ID NO: 92) VH 4GLR + Human CH1

AVTLDESGGGLQTPGGGLSLVCKASGFTLSSYQMMWVRQAPGKGLEWVAGITSRGGVTGYGSAVK
GRATISRDNGQSTVRLQLNNLRAEDTGTYYCAKPALDSDQCGFPEAGCIDAWGHGTEVTVSSAST
KGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKRV

Figure 19G (SEQ ID NO: 93) VK1-39/IGJK5/Ckappa

DIQMTQSPSSLSASVGDRVTITCRASQSISSYLNWYQQKPGKAPKLLIYAASSLQSGVPSRFSGS
GSGTDFTLTISSLQPEDFATYYCQQSYSTPPITFGQGTRLEIKRTVAAPSVFIFPPSDEQLKSGT
ASVVCLLNNFYPREAKVQWKVDNALQSGNSQESVTEQDSKDSTYSLSSTLTLSKADYEKHKVYAC
EVTHQGLSSPVTKSFNRGEC

Figure 19H (SEQ ID NO: 94) IgVκ3-15/IGJκ1/Ckappa

EIVMTQSPATLSVSPGERATLSCRASQSVSSNLAWYQQKPGQAPRLLIYGASTRATGIPARFSGS
GSGTEFTLTISSLQSEDFAVYYCQQYNNWPWTFGQGTKVEIKRTVAAPSVFIFPPSDEQLKSGTA
SVVCLLNNFYPREAKVQWKVDNALQSGNSQESVTEQDSKDSTYSLSSTLTLSKADYEKHKVYACE
VTHQGLSSPVTKSFNRGEC

Figure 19I (SEQ ID NO: 95) IgVκ3-20/IGJκ1/Ckappa

```
EIVLTQSPGTLSLSPGERATLSCRASQSVSSSYLAWYQQKPGQAPRLLIYGASSRATGIPDRFSG
SGSGTDFTLTISRLEPEDFAVYYCQQYGSSPWTFGQGTKVEIKRTVAAPSVFIFPPSDEQLKSGT
ASVVCLLNNFYPREAKVQWKVDNALQSGNSQESVTEQDSKDSTYSLSSTLTLSKADYEKHKVYAC
EVTHQGLSSPVTKSFNRGEC
```

Figure 19J (SEQ ID NO: 96) IgVλ3-21/IGJλ3/Clambda

```
SYVLTQPPSVSVAPGETARITCGGDNIGRKSVYWYQQKSGQAPVLVIYYDSDRPSGIPERFSGSN
SGNTATLTISRVEAGDEADYYCQVWDGSSDHWVFGGGTKLTVLGQPKAAPSVTLFPPSSEELQAN
KATLVCLISDFYPGAVTVAWKADSSPVKAGVETTTPSKQSNNKYAASSYLSLTPEQWKSHRSYSC
QVTHEGSTVEKTVAPTECS
```

Figure 19K (SEQ ID NO: 97) IgVλ3-21

```
SYVLTQPPSVSVAPGETARITCGGDNIGRKSVYWYQQKSGQAPVLVIYYDSDRPSGIPERFSGSN
SGNTATLTISRVEAGDEADYYCQVWDGSSDH
```

Figure 20

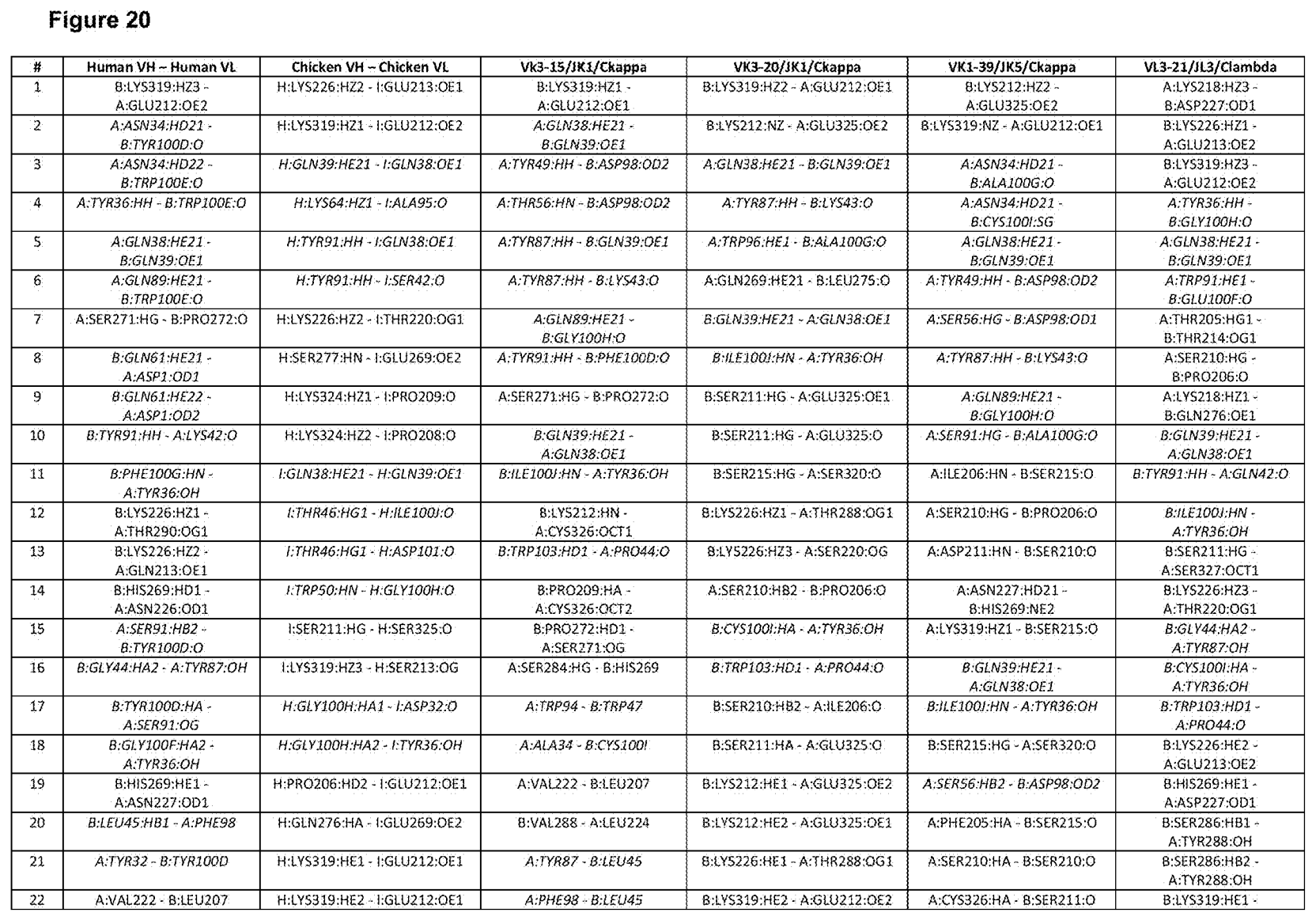

| # | Human VH – Human VL | Chicken VH – Chicken VL | VK3-15/JK1/Ckappa | VK3-20/JK1/Ckappa | VK1-39/JK5/Ckappa | Vl3-21/Jl3/Clambda |
|---|---|---|---|---|---|---|
| 1 | B:LYS319:HZ3 - A:GLU212:OE2 | H:LYS319:HZ3 - I:GLU213:OE1 | B:LYS319:HZ1 - A:GLU212:OE1 | B:LYS319:HZ2 - A:GLU212:OE1 | B:LYS212:HZ2 - A:GLU325:OE2 | A:LYS218:H23 - B:ASP227:OD1 |
| 2 | A:ASN34:HD21 - B:TYR100D:O | H:LYS319:HZ1 - I:GLU212:OE2 | A:GLN38:HE21 - B:GLN39:OE1 | B:LYS212:NZ - A:GLU325:OE2 | B:LYS319:NZ - A:GLU212:OE1 | B:LYS226:HZ1 - A:GLU213:OE2 |
| 3 | A:ASN34:HD22 - B:TRP100E:O | H:GLN39:HE21 - I:THR220:OG1 | A:TYR49:HH - B:ASP98:OD2 | A:GLN38:HE21 - B:GLN39:OE1 | A:ASN34:HD21 - B:ALA100G:O | B:LYS319:H23 - A:GLU212:OE2 |
| 4 | A:TYR36:HH - B:TRP100E:O | H:LYS64:HZ1 - I:ALA95:O | A:THR56:HN - B:ASP98:OD2 | A:TYR87:HH - B:LYS43:O | A:ASN34:HD21 - B:CYS100I:SG | A:TYR36:HH - B:GLY100H:O |
| 5 | A:GLN38:HE21 - B:GLN39:OE1 | H:TYR91:HH - I:GLN38:OE1 | A:TYR87:HH - B:GLN39:OE1 | A:TRP96:HE1 - B:ALA100G:O | A:GLN38:HE21 - B:GLN39:OE1 | A:GLN38:HE21 - B:GLN39:OE1 |
| 6 | A:GLN89:HE21 - B:TRP100E:O | H:TYR91:HH - I:SER42:O | A:TYR87:HH - B:LYS43:O | A:GLN269:HE21 - B:LEU275:O | A:TYR49:HH - B:ASP98:OD2 | A:TRP91:HE1 - B:GLU100F:O |
| 7 | A:SER271:HG - B:PRO272:O | H:LYS226:HZ2 - I:THR220:OG1 | A:GLN89:HE21 - B:GLY100H:O | B:GLN39:HE21 - A:GLN38:OE1 | A:SER56:HG - B:ASP98:OD1 | A:THR205:HG1 - B:THR214:OG1 |
| 8 | B:GLN61:HE1 - A:ASP1:OD1 | H:SER277:HN - I:GLU269:OE2 | A:TYR91:HH - B:PHE100D:O | B:ILE100J:HN - A:TYR36:OH | A:TYR87:HH - B:LYS43:O | A:SER210:HG - B:PRO206:O |
| 9 | B:GLN61:HE22 - A:ASP1:OD2 | H:LYS324:HZ1 - I:PRO209:O | A:SER271:HG - B:PRO272:O | B:SER211:HG - A:GLU325:OE1 | A:GLN89:HE21 - B:GLY100H:O | A:LYS218:HZ1 - B:GLN276:OE1 |
| 10 | B:TYR91:HH - A:LYS42:O | H:LYS324:HZ2 - I:PRO208:O | B:GLN39:HE21 - A:GLN38:OE1 | B:SER211:HG - A:GLU325:O | A:SER91:HG - B:ALA100G:O | B:GLN39:HE21 - A:GLN38:OE1 |
| 11 | B:PHE100G:HN - A:TYR36:OH | I:GLN38:HE21 - H:GLN39:OE1 | B:ILE100J:HN - A:TYR36:OH | B:SER215:HG - A:SER320:O | A:ILE206:HN - B:SER215:O | B:TYR91:HH - A:GLN42:O |
| 12 | B:LYS226:HZ1 - A:THR290:OG1 | I:THR46:HG1 - H:ILE100I:O | B:LYS212:HN - A:CYS326:OCT1 | B:LYS226:HZ1 - A:THR288:OG1 | A:SER210:HG - B:PRO206:O | B:ILE100J:HN - A:TYR36:OH |
| 13 | B:LYS226:HZ2 - A:GLN213:OE1 | I:THR46:HG1 - H:ASP101:O | B:TRP103:HD1 - A:PRO44:O | B:LYS226:HZ3 - A:SER220:OG | A:ASP211:HN - B:SER210:O | B:SER211:HG - A:SER327:OCT1 |
| 14 | B:HIS269:HD1 - A:ASN226:OO1 | I:TRP50:HN - H:GLY100H:O | B:PRO209:HA - A:CYS326:OCT2 | A:SER210:HB2 - B:PRO206:O | A:ASN227:HD21 - B:HIS269:NE2 | B:LYS226:H23 - A:THR220:OG1 |
| 15 | B:SER91:HB2 - B:TYR100D:O | I:SER211:HG - H:SER325:O | B:PRO272:HD1 - A:SER271:OG | B:CYS100I:HA - A:TYR36:OH | A:LYS319:HZ1 - B:SER215:O | B:GLY44:HA2 - A:TYR87:OH |
| 16 | B:GLY44:HA2 - A:TYR87:OH | I:LYS319:H23 - H:SER213:OG | A:SER284:HG - B:HIS269 | B:TRP103:HD1 - A:PRO44:O | B:GLN39:HE21 - A:GLN38:OE1 | B:CYS100I:HA - A:TYR36:OH |
| 17 | B:TYR100D:HA - A:SER91:OG | H:GLY100H:HA1 - I:ASP32:O | A:TRP94 - B:TRP47 | B:SER210:HB2 - A:ILE206:O | B:ILE100J:HN - A:TYR36:OH | B:TRP103:HD1 - A:PRO44:O |
| 18 | B:GLY100F:HA2 - A:TYR36:OH | H:GLY100H:HA2 - I:TYR36:OH | A:ALA34 - B:CYS100I | B:SER211:HA - A:GLU325:O | B:SER215:HG - A:SER320:O | B:LYS226:HE2 - A:GLU213:OE2 |
| 19 | B:HIS269:HE1 - A:ASN227:OD1 | H:PRO206:HD2 - I:GLU212:OE1 | A:VAL222 - B:LEU207 | B:LYS212:HE1 - A:GLU325:OE2 | A:SER56:HB2 - B:ASP98:OD2 | B:HIS269:HE1 - A:ASP227:OD1 |
| 20 | B:LEU45:HB1 - A:PHE98 | H:GLN276:HA - I:GLU269:OE2 | B:VAL288 - A:LEU224 | B:LYS212:HE2 - A:GLU325:OE1 | A:PHE205:HA - B:SER215:O | B:SER286:HB1 - A:TYR288:OH |
| 21 | A:TYR32 - B:TYR100D | H:LYS319:HE1 - I:GLU212:OE1 | A:TYR87 - B:LEU45 | B:LYS226:HE1 - A:THR288:OG1 | A:SER210:HA - B:SER210:O | B:SER286:HB2 - A:TYR288:OH |
| 22 | A:VAL222 - B:LEU207 | H:LYS319:HE2 - I:GLU212:OE1 | A:PHE98 - B:LEU45 | B:LYS319:HE2 - A:GLU212:OE2 | A:CYS326:HA - B:SER211:O | B:LYS319:HE1 - |

Figure 20 (continued)

| # | | | | | | |
|----|----|----|----|----|----|----|
| 23 | B:VAL288 - A:LEU224 | I:GLY41:HA2 - H:THR89:OG1 | A:PHE205 - B:ALA220 | A:TRP96:HB1 - B:TRP47 | B:SER211:HB2 - A:PRO209:O | A:GLU212:OE1 |
| 24 | A:PHE205 - B:ALA220 | I:GLY41:HA2 - H:TYR91:OH | A:PHE207 - B:LEU207 | B:MET35:SD - A:TRP96 | B:GLY216:HA1 - A:ILE206:O | B:LYS319:HE2 - A:GLU212:OE2 |
| 25 | A:PHE207 - B:LEU207 | I:TYR49:HA - H:GLY100H:O | A:PHE207 - B:PRO209 | B:MET35:SD - A:TRP96 | B:GLY216:HA2 - A:ILE206:O | A:LYS275:NZ - B:HIS269 |
| 26 | B:TRP47 - A:PRO96 | I:GLY96:HA1 - H:PRO100E:O | A:PHE207 - B:ALA220 | A:TRP96 - B:TRP47 | B:HIS269:HE1 - A:ASN227:OD1 | A:TRP96:HN - B:TRP47 |
| 27 | B:TRP47 - A:PRO95 | I:GLY96:HA2 - H:PRO100E:O | B:TYR91 - A:ALA43 | A:TRP96 - B:TRP47 | B:LYS319:HE1 - A:GLU212:OE2 | A:HIS95B - B:TRP47 |
| 28 | B:TRP47 - A:PRO96 | H:TRP103 - I:TYR36 | B:TRP103 - A:ALA43 | A:TRP96 - B:TRP47 | A:SER284:HG - B:HIS269 | A:PRO44 - B:LEU45 |
| 29 | B:TYR91 - A:ALA43 | H:LEU207:C,O;ALA208:N - I:PHE207 | B:TRP103 - A:PRO44 | B:TRP47 - A:TRP96 | A:TYR36 - B:TRP103 | A:VAL222 - B:LEU207 |
| 30 | B:TYR100D - A:ALA50 | I:PRO44 - H:LEU45 | B:TRP103 - A:ALA43 | A:PRO44 - B:LEU45 | A:PRO44 - B:LEU45 | A:VAL268 - B:VAL274 |
| 31 | B:TRP100E - A:PRO96 | I:VAL222 - H:LEU207 | B:TRP103 - A:PRO44 | A:VAL222 - B:LEU207 | A:PRO208 - B:LYS212 | B:CYS100I - A:LEU46 |
| 32 | B:TRP103 - A:ALA43 | I:VAL222 - H:LEU224 | | A:VAL222 - B:LEU224 | A:VAL222 - B:LEU207 | B:ALA220 - A:LEU224 |
| 33 | B:TRP103 - A:PRO44 | H:TYR91 - I:PRO44 | | B:CYS100I - A:LEU46 | B:ALA62 - A:PRO95A | A:TYR34 - B:ALA100G |
| 34 | B:TRP103 - A:ALA43 | H:TRP103 - I:PRO44 | | B:VAL288 - A:LEU224 | B:CYS100I - A:LEU46 | A:TYR34 - B:CYS100I |
| 35 | B:TRP103 - A:PRO44 | H:TRP103 - I:PRO44 | | A:TYR32 - B:ALA100G | B:VAL288 - A:LEU224 | A:TYR87 - B:LEU45 |
| 36 | | H:PHE205 - I:ALA216 | | A:TYR36 - B:ILE100J | A:TYR32 - B:ALA100G | A:TRP91 - B:ALA100G |
| 37 | | H:HIS269 - I:ALA284 | | A:TYR49 - B:CYS100I | A:TYR36 - B:ILE100J | A:PHE98 - B:LEU45 |
| 38 | | H:PHE271 - I:LEU224 | | A:TYR87 - B:LEU45 | A:TYR87 - B:ILE45 | A:PHE207 - B:LEU207 |
| 39 | | I:TYR36 - H:ILE100J | | A:PHE98 - B:VAL37 | A:PHE98 - B:VAL37 | B:TYR91 - A:ALA43 |
| 40 | | I:TYR49 - H:ALA96 | | A:PHE98 - B:LEU45 | A:PHE98 - B:LEU45 | B:TRP103 - A:ALA43 |
| 41 | | I:TRP50 - H:CYS100B | | A:PHE205 - B:ALA220 | A:PHE205 - B:ALA220 | B:TRP103 - A:PRO44 |
| 42 | | I:TRP50 - H:CYS100I | | A:PHE207 - B:LEU207 | B:TRP47 - A:PRO95A | B:TRP103 - A:ALA43 |
| 43 | | I:TYR87 - H:LEU45 | | A:PHE207 - B:ALA220 | B:TYR91 - A:ALA43 | B:HIS269 - A:LYS275 |
| 44 | | I:TYR91 - H:PRO100E | | B:TRP103 - A:ALA43 | B:TRP103 - A:PRO44 | B:PHE271 - A:ALA284 |
| 45 | | I:PHE98 - H:VAL37 | | B:TRP103 - A:PRO44 | B:TRP103 - A:PRO44 | |
| 46 | | I:PHE98 - H:LEU45 | | B:TRP103 - A:PRO44 | | |
| 47 | | I:PHE98 - H:ALA100G | | B:PHE271 - A:LEU224 | | |
| 48 | | I:PHE207 - H:LEU207 | | | | |
| 49 | | I:PHE207 - H:ALA220 | | | | |
| 50 | | I:TYR288 - H:VAL274 | | | | |

Figure 22 (SEQ ID NO: 98) Human control MF1025 VH sequence

EVQLVESGGGLVQPGGSLRLSCAASGFTFSSYAMSWVRQAPGKGLEWVSAISGSGGSTYYADSVK
GRFTISRDNSKNTLYLQMNSLRAEDTAVYYCARADWWATFDYWGQGTLVTVSS

Figure 23
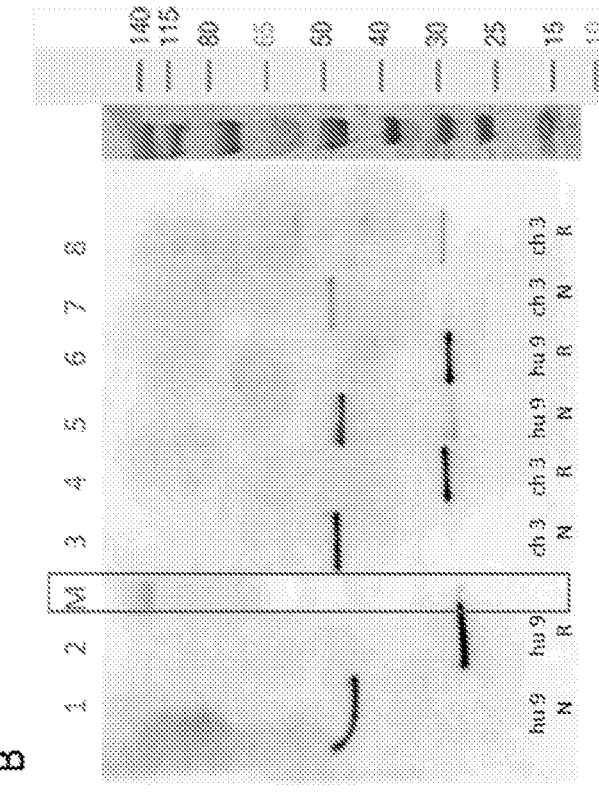
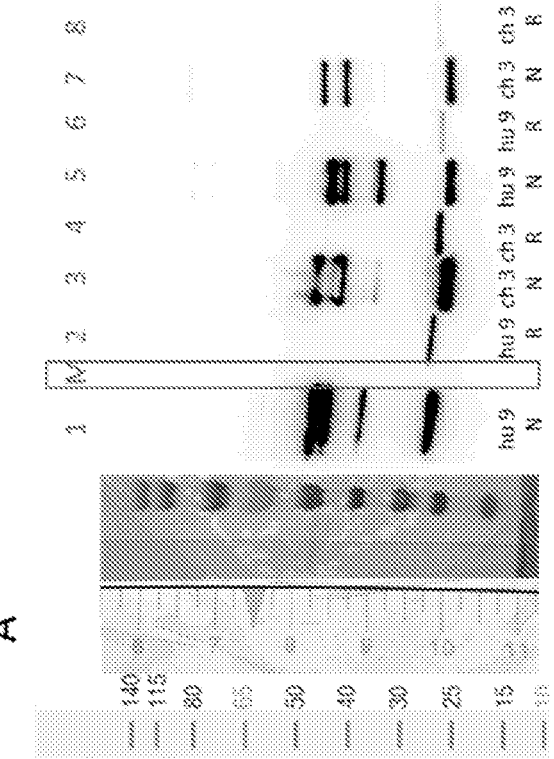

Figure 24 (SEQ ID NO: 99) WT full length sequence mouse CXCR4 GenBank: AAH98322.1

MEPISVSIYT SDNYSEEVGS GDYDSNKEPC FRDENVHFNR IFLPTIYFII
FLTGIVGNGL VILVMGYQKK LRSMTDKYRL HLSVADLLFV ITLPFWAVDA
MADWYFGKFL CKAVHIIYTV NLYSSVLILA FISLDRYLAI VHATNSQRPR
KLLAEKAVYV GVWIPALLLT IPDFIFADVS QGDISQGDDR YICDRLYPDS
LWMVVFQFQH IMVGLILPGI VILSCYCIII SKLSHSKGHQ KRKALKTTVI LILAFFACWL
PYYVGISIDS FILLGVIKQG CDFESIVHKW ISITEALAFF HCCLNPILYA FLGAKFKSSA
QHALNSMSRG SSLKILSKGK RGGHSSVSTE SESSSFHSS

Figure 26A (SEQ ID NO: 100) cLC CXCR4 - 1

AVTLDESGGGLQTPGGALSLVCKASGFTFSSYRGMHWVRQAPGKGLEWVAGIYSSG
SSTAYGAAVKGRATISRDDGQSTVRLQLNNLRAEDTGTYYCAKDAGSCWYGRRSGFN
CDPYGGNIDAWGHGTEVIVSS

Figure 26B (SEQ ID NO: 101) cLC CXCR4 - 2

AVTLDESGGGLQTPGGALSLVCKASGFSFSSYDMSWVRQAPGKGLEWVAGIYSIGRD
AGYGAAVKGRATISRDNGQSTVRLQLNNLRAEDTGTYYCAKESGSACRYAARHGYICA
GYLGSIDAWGHGTEVIVSS

Figure 26C (SEQ ID NO: 102) cLC CXCR4 – 3

AVTLDESGGGLQTPGGALSLVCKASGFSIGSYGMGWVRQAPGKGLEFVAGISTIGGVT
WYGAAVKGRAIISRDNGQSTVRLQLNNLRAEDTGTYFCAKASDSPSCRYGSRSGWSC
PGWNYGGRIDAWGHGTEVIVSS

SEQUENCE LISTING

<160> NUMBER OF SEQ ID NOS: 102

<210> SEQ ID NO 1
<211> LENGTH: 124
<212> TYPE: PRT
<213> ORGANISM: Artificial Sequence
<220> FEATURE:
<223> OTHER INFORMATION: VH region of MF3178

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 2
<211> LENGTH: 127
<212> TYPE: PRT
<213> ORGANISM: Artificial Sequence
<220> FEATURE:
<223> OTHER INFORMATION: heavy chain variable region of the chicken Fab
      region PDB 4GLR

<400> SEQUENCE: 2

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Leu Ser Ser Tyr
            20                  25                  30

Gln Met Met Trp Val Arg Gln Ala Pro Gly Lys Gly Leu Glu Trp Val
        35                  40                  45

Ala Gly Ile Thr Ser Arg Gly Gly Val Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly His Gly Thr Glu Val Thr Val Ser Ser
        115                 120                 125
```

<210> SEQ ID NO 3
<211> LENGTH: 126
<212> TYPE: PRT
<213> ORGANISM: Anas platyrhynchos

<400> SEQUENCE: 3

-continued

```
Ala Glu Thr Leu Asp Glu Ser Gly Gly Gly Leu Val Ser Pro Gly Gly
1               5                   10                  15

Ser Leu Thr Leu Val Cys Lys Gly Ser Gly Phe Thr Phe Ser Ser Asn
            20                  25                  30

Glu Met Tyr Trp Val Arg Gln Ala Pro Gly Lys Gly Leu Glu Trp Val
        35                  40                  45

Ala Gly Ile Thr Thr Gly Gly Tyr Thr Gly Tyr Ala Pro Ala Val Lys
    50                  55                  60

Gly Arg Phe Thr Ile Ser Arg Asn Asn Gly Gln Ser Thr Leu Thr Leu
65                  70                  75                  80

Gln Met Asn Ser Leu Lys Ala Glu Asp Thr Ala Thr Tyr Tyr Cys Ala
                85                  90                  95

Lys Ile Thr Gly Tyr Ala Asn Cys Ala Gly Tyr Gly Cys Ala Ala Asp
                100                 105                 110

Ile Asp Leu Trp Gly His Gly Thr Glu Val Thr Val Ser Ser
                115                 120                 125
```

<210> SEQ ID NO 4
<211> LENGTH: 124
<212> TYPE: PRT
<213> ORGANISM: Struthio camelus

<400> SEQUENCE: 4

```
Ala Val Gln Leu Val Glu Ser Gly Gly Gly Leu Gln Gln Pro Gly Gly
1               5                   10                  15

Ser Leu Arg Leu Ser Cys Lys Gly Thr Gly Phe Thr Leu Ser Ser Phe
            20                  25                  30

Gly Met Ser Trp Ile Arg Gln Ala Pro Gly Lys Gly Leu Glu Pro Val
        35                  40                  45

Ala Gly Ile Ser Ser Ser Gly Ser Asp Thr Tyr Tyr Ala Asp Ala Val
    50                  55                  60

Gln Gly Arg Phe Thr Ile Ser Arg Asp Asn Gly Gln Ser Thr Leu Tyr
65                  70                  75                  80

Leu Gln Met Asn Gly Leu Lys Ala Glu Asp Thr Ala Thr Tyr Tyr Cys
                85                  90                  95

Ala Lys Cys Ala Thr Asp Trp Gly Ser Cys Gly Pro Trp Asn Leu Asp
                100                 105                 110

Ala Trp Gly Arg Gly Ala Ser Val Thr Val Ser Ser
                115                 120
```

<210> SEQ ID NO 5
<211> LENGTH: 214
<212> TYPE: PRT
<213> ORGANISM: Artificial Sequence
<220> FEATURE:
<223> OTHER INFORMATION: human kappa light chain IgVk1-39*01/IGJk1*01

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
                65                    70                   75                    80
Glu Asp Phe Ala Thr Tyr Tyr Cys Gln Gln Ser Tyr Ser Thr Pro Pro
                         85                    90                    95

Thr Phe Gly Gln Gly Thr Lys Val Glu Ile Lys Arg Thr Val Ala Ala
                100                   105                   110

Pro Ser Val Phe Ile Phe Pro Pro Ser Asp Glu Gln Leu Lys Ser Gly
                115                   120                   125

Thr Ala Ser Val Val Cys Leu Leu Asn Asn Phe Tyr Pro Arg Glu Ala
            130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                    165                   170                   175

Ser Thr Leu Thr Leu Ser Lys Ala Asp Tyr Glu Lys His Lys Val Tyr
                180                   185                   190

Ala Cys Glu Val Thr His Gln Gly Leu Ser Ser Pro Val Thr Lys Ser
                195                   200                   205

Phe Asn Arg Gly Glu Cys
    210

<210> SEQ ID NO 6
<211> LENGTH: 321
<212> TYPE: DNA
<213> ORGANISM: Artificial Sequence
<220> FEATURE:
<223> OTHER INFORMATION: common light chain variable region -
      IGKV1-39/jk1

<400> SEQUENCE: 6
gacatccaga tgacccagtc tccatcctcc ctgtctgcat ctgtaggaga cagagtcacc      60
atcacttgcc gggcaagtca gagcattagc agctacttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccaac gttcggccaa     300
gggaccaagg tggagatcaa a                                               321

<210> SEQ ID NO 7
<211> LENGTH: 107
<212> TYPE: PRT
<213> ORGANISM: Artificial Sequence
<220> FEATURE:
<223> OTHER INFORMATION: common light chain variable region -
      IGKV1-39/jk1

<400> SEQUENCE: 7

Asp Ile Gln Met Thr Gln Ser Pro Ser Ser Leu Ser Ala Ser Val Gly
1                   5                    10                   15

Asp Arg Val Thr Ile Thr Cys Arg Ala Ser Gln Ser Ile Ser Ser Tyr
                20                    25                   30

Leu Asn Trp Tyr Gln Gln Lys Pro Gly Lys Ala Pro Lys Leu Leu Ile
            35                    40                    45

Tyr Ala Ala Ser Ser Leu Gln Ser Gly Val Pro Ser Arg Phe Ser Gly
        50                    55                    60

Ser Gly Ser Gly Thr Asp Phe Thr Leu Thr Ile Ser Ser Leu Gln Pro
65                    70                    75                   80

Glu Asp Phe Ala Thr Tyr Tyr Cys Gln Gln Ser Tyr Ser Thr Pro Pro
```

-continued

```
                    85              90              95
Thr Phe Gly Gln Gly Thr Lys Val Glu Ile Lys
            100             105
```

```
<210> SEQ ID NO 8
<211> LENGTH: 324
<212> TYPE: DNA
<213> ORGANISM: Artificial Sequence
<220> FEATURE:
<223> OTHER INFORMATION: common light chain constant region

<400> SEQUENCE: 8
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                          324
```

```
<210> SEQ ID NO 9
<211> LENGTH: 107
<212> TYPE: PRT
<213> ORGANISM: Artificial Sequence
<220> FEATURE:
<223> OTHER INFORMATION: common light chain constant region

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100             105
```

```
<210> SEQ ID NO 10
<211> LENGTH: 108
<212> TYPE: PRT
<213> ORGANISM: Artificial Sequence
<220> FEATURE:
<223> OTHER INFORMATION: common light chain variable domain -
      IGKV1-39/jk5

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

-continued

```
         50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln Ser Tyr Ser Thr Pro Pro
                     85                    90                    95

Ile Thr Phe Gly Gln Gly Thr Arg Leu Glu Ile Lys
            100                   105

<210> SEQ ID NO 11
<211> LENGTH: 95
<212> TYPE: PRT
<213> ORGANISM: Artificial Sequence
<220> FEATURE:
<223> OTHER INFORMATION: common light chain variable domain V gene
      segment - IGKV1-39

<400> SEQUENCE: 11

Asp Ile Gln Met Thr Gln Ser Pro Ser Ser Leu Ser Ala Ser Val Gly
1               5                    10                    15

Asp Arg Val Thr Ile Thr Cys Arg Ala Ser Gln Ser Ile Ser Ser Tyr
                20                    25                    30

Leu Asn Trp Tyr Gln Gln Lys Pro Gly Lys Ala Pro Lys Leu Leu Ile
            35                    40                    45

Tyr Ala Ala Ser Ser Leu Gln Ser Gly Val Pro Ser Arg Phe Ser Gly
         50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln Ser Tyr Ser Thr Pro
                     85                    90                    95

<210> SEQ ID NO 12
<211> LENGTH: 100
<212> TYPE: PRT
<213> ORGANISM: Anas platyrhynchos

<400> SEQUENCE: 12

Asn Ile Lys Met Val Ala Ser Gly Pro Lys Glu Gly Lys Ile Leu Gly
1               5                    10                    15

Ser Leu Pro Leu Thr Cys Thr Val Ile Gly Ala Pro Leu Asp Ser Pro
                20                    25                    30

Arg Tyr Asp Trp Asn Tyr Val Arg Leu Ala Pro Thr Gly Glu Leu Gln
            35                    40                    45

Phe Leu Ala Trp Val Tyr Pro Phe Gly Asn Asn Thr Gly Tyr Ala Pro
         50                    55                    60

Pro Phe Gln Ser Arg Ala Thr Ile Ser Ala Asp Lys Ala Lys Lys Lys
65                    70                    75                    80

Val Ser Leu Gln Leu His Ala Leu Thr Ala Val Asp Thr Ala Thr Tyr
                     85                    90                    95

Phe Cys Ala Arg
            100

<210> SEQ ID NO 13
<211> LENGTH: 98
<212> TYPE: PRT
<213> ORGANISM: Struthio camelus

<400> SEQUENCE: 13

Ala Glu Gln Leu Val Glu Ser Gly Gly Gly Arg Gln Gln Pro Gly Gly
1               5                    10                    15
```

```
Ser Leu Arg Leu Ser Cys Lys Gly Thr Gly Phe Thr Phe Ser Ser Phe
         20              25              30

Asn Met Glu Trp Val Arg Gln Ala Pro Gly Lys Gly Leu Glu Trp Val
     35              40              45

Ala Ala Ile Tyr Ser Ser Gly Ser Ser Thr Ser Tyr Ala Pro Ser Val
 50              55              60

Gln Gly Arg Phe Thr Ile Ser Arg Asp Asn Gly Gln Ser Thr Leu Tyr
65              70              75              80

Leu Gln Met Asn Ser Leu Lys Ala Glu Asp Thr Ala Thr Tyr Tyr Cys
             85              90              95

Ala Lys
```

```
<210> SEQ ID NO 14
<211> LENGTH: 101
<212> TYPE: PRT
<213> ORGANISM: Gallus gallus

<400> SEQUENCE: 14

Ala Val Thr Leu Asp Glu Ser Gly Gly Gly Leu Gln Thr Pro Gly Arg
1               5               10              15

Ala Leu Ser Leu Val Cys Lys Ala Ser Gly Phe Thr Phe Ser Ser Tyr
         20              25              30

Asn Met Gly Trp Val Arg Gln Ala Pro Gly Lys Gly Leu Glu Phe Val
     35              40              45

Ala Gly Ile Asp Asn Thr Gly Arg Tyr Thr Gly Tyr Gly Ser Ala Val
 50              55              60

Lys Gly Arg Ala Thr Ile Ser Arg Asp Asn Gly Gln Ser Thr Val Arg
65              70              75              80

Leu Gln Leu Asn Asn Leu Arg Ala Glu Asp Thr Gly Thr Tyr Tyr Cys
             85              90              95

Ala Lys Ala Ala Gly
         100
```

```
<210> SEQ ID NO 15
<211> LENGTH: 54
<212> TYPE: DNA
<213> ORGANISM: Artificial Sequence
<220> FEATURE:
<223> OTHER INFORMATION: chVH-FW primer

<400> SEQUENCE: 15
gtcctcgcaa ctgcggccca gccggccatg gccgccgtga cgttggacga gtcc          54
```

```
<210> SEQ ID NO 16
<211> LENGTH: 24
<212> TYPE: DNA
<213> ORGANISM: Artificial Sequence
<220> FEATURE:
<223> OTHER INFORMATION: chVH-RV primer

<400> SEQUENCE: 16
ggaggagacg gtgacctcgg tccc                                            24
```

```
<210> SEQ ID NO 17
<211> LENGTH: 870
<212> TYPE: DNA
<213> ORGANISM: Homo sapiens

<400> SEQUENCE: 17
```

```
atgcagatcc cacaggcgcc ctggccagtc gtctgggcgg tgctacaact gggctggcgg        60
ccaggatggt tcttagactc cccagacagg ccctggaacc cccccacctt ctccccagcc       120
ctgctcgtgg tgaccgaagg ggacaacgcc accttcacct gcagcttctc caacacatcg       180
gagagcttcg tgctaaactg gtaccgcatg agccccagca accagacgga caagctggcc       240
gccttccccg aggaccgcag ccagcccggc caggactgcc gcttccgtgt cacacaactg       300
cccaacgggc gtgacttcca catgagcgtg gtcagggccc ggcgcaatga cagcggcacc       360
tacctctgtg gggccatctc cctggccccc aaggcgcaga tcaaagagag cctgcgggca       420
gagctcaggg tgacagagag aagggcagaa gtgcccacag cccaccccag cccctcaccc       480
aggccagccg gccagttcca aaccctggtg gttggtgtcg tgggcggcct gctgggcagc       540
ctggtgctgc tagtctgggt cctggccgtc atctgctccc gggccgcacg agggacaata       600
ggagccaggc gcaccggcca gcccctgaag gaggacccct cagccgtgcc tgtgttctct       660
gtggactatg gggagctgga tttccagtgg cgagagaaga ccccggagcc ccccgtgccc       720
tgtgtccctg agcagacgga gtatgccacc attgtctttc ctagcggaat gggcacctca       780
tcccccgccc gcaggggctc agctgacggc cctcggagtg cccagccact gaggcctgag       840
gatggacact gctcttggcc cctctgatga                                        870
```

```
<210> SEQ ID NO 18
<211> LENGTH: 462
<212> TYPE: DNA
<213> ORGANISM: Artificial Sequence
<220> FEATURE:
<223> OTHER INFORMATION: human PD-1 codon-optimized for expression in
      chicken

<400> SEQUENCE: 18
ggatccccag gatggttcct ggatagcccc gacagaccat ggaacccacc aacattcagc        60
cccgctctgc tggtggttac cgagggcgat aacgccacct tcacatgcag cttcagcaac       120
accagcgaga gcttcgtgct gaactggtac agaatgagcc ccagcaacca gaccgacaag       180
ctggctgctt ccccgagga tagaagccag ccaggccagg actgcagatt cagagtgaca       240
cagctgccca cggcagaga cttccacatg tctgttgtgc gcgccagaag aaacgacagc       300
ggcacatatc tgtgcggcgc cattagcctg ctccaaagg ctcagatcaa agagagcctg       360
agagccgagc tgagagtgac agagcgcaga gctgaagtgc ccacagctca cccatctcca       420
tctccaagac cagccggcca gttccagaca ctggtgctcg ag                         462
```

```
<210> SEQ ID NO 19
<211> LENGTH: 33
<212> TYPE: DNA
<213> ORGANISM: Artificial Sequence
<220> FEATURE:
<223> OTHER INFORMATION: Forward primer

<400> SEQUENCE: 19
gtcctcgcaa ctgcggccca gccggccatg gcc                                     33
```

```
<210> SEQ ID NO 20
<211> LENGTH: 21
<212> TYPE: DNA
<213> ORGANISM: Artificial Sequence
<220> FEATURE:
<223> OTHER INFORMATION: forward primer

<400> SEQUENCE: 20
```

```
gccgtgacgt tggacgagtc c                                                    21

<210> SEQ ID NO 21
<211> LENGTH: 98
<212> TYPE: PRT
<213> ORGANISM: Artificial Sequence
<220> FEATURE:
<223> OTHER INFORMATION: human VH1-02 (DP-75)

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 22
<211> LENGTH: 98
<212> TYPE: PRT
<213> ORGANISM: Artificial Sequence
<220> FEATURE:
<223> OTHER INFORMATION: human VH1-02 (DP-8)

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 23
<211> LENGTH: 98
<212> TYPE: PRT
<213> ORGANISM: Artificial Sequence
<220> FEATURE:
<223> OTHER INFORMATION: human VH1-08 (DP-15)

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
```

-continued

```
              35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                    85                  90                  95
Ala Arg

<210> SEQ ID NO 24
<211> LENGTH: 98
<212> TYPE: PRT
<213> ORGANISM: Artificial Sequence
<220> FEATURE:
<223> OTHER INFORMATION: human VH1-46 (DP-7)

<400> SEQUENCE: 24

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                    85                  90                  95
Ala Arg

<210> SEQ ID NO 25
<211> LENGTH: 98
<212> TYPE: PRT
<213> ORGANISM: Artificial Sequence
<220> FEATURE:
<223> OTHER INFORMATION: human VH1-03 (DP-25)

<400> SEQUENCE: 25

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Ala Met His Trp Val Arg Gln Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                    85                  90                  95
Ala Arg

<210> SEQ ID NO 26
<211> LENGTH: 98
<212> TYPE: PRT
<213> ORGANISM: Artificial Sequence
<220> FEATURE:
```

<223> OTHER INFORMATION: human VH1-18 (DP-14)

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg
```

<210> SEQ ID NO 27
<211> LENGTH: 98
<212> TYPE: PRT
<213> ORGANISM: Artificial Sequence
<220> FEATURE:
<223> OTHER INFORMATION: human VH1-45 (DP-4)

<400> SEQUENCE: 27

```
Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg
```

<210> SEQ ID NO 28
<211> LENGTH: 98
<212> TYPE: PRT
<213> ORGANISM: Artificial Sequence
<220> FEATURE:
<223> OTHER INFORMATION: human VH1-58 (DP-2)

<400> SEQUENCE: 28

```
Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80
```

-continued

```
Met Glu Leu Ser Ser Leu Arg Ser Glu Asp Thr Ala Val Tyr Tyr Cys
            85                  90                  95

Ala Ala

<210> SEQ ID NO 29
<211> LENGTH: 98
<212> TYPE: PRT
<213> ORGANISM: Artificial Sequence
<220> FEATURE:
<223> OTHER INFORMATION: human VH1-69 (DP-10)

<400> SEQUENCE: 29

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 30
<211> LENGTH: 98
<212> TYPE: PRT
<213> ORGANISM: Artificial Sequence
<220> FEATURE:
<223> OTHER INFORMATION: human VH1-e (DP-88)

<400> SEQUENCE: 30

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg

<210> SEQ ID NO 31
<211> LENGTH: 98
<212> TYPE: PRT
<213> ORGANISM: Artificial Sequence
<220> FEATURE:
<223> OTHER INFORMATION: human VH1-24 (DP-5)

<400> SEQUENCE: 31

Gln Val Gln Leu Val Gln Ser Gly Ala Glu Val Lys Lys Pro Gly Ala
1               5                  10                  15

Ser Val Lys Val Ser Cys Lys Val Ser Gly Tyr Thr Leu Thr Glu Leu
```

-continued

```
            20              25              30
Ser Met His Trp Val Arg Gln Ala Pro Gly Lys Gly Leu Glu Trp Met
        35              40              45
Gly Gly Phe Asp Pro Glu Asp Gly Glu Thr Ile Tyr Ala Gln Lys Phe
    50              55              60
Gln Gly Arg Val Thr Met Thr Glu Asp Thr Ser Thr Asp Thr Ala Tyr
65              70              75              80
Met Glu Leu Ser Ser Leu Arg Ser Glu Asp Thr Ala Val Tyr Tyr Cys
                85              90              95
Ala Thr

<210> SEQ ID NO 32
<211> LENGTH: 98
<212> TYPE: PRT
<213> ORGANISM: Artificial Sequence
<220> FEATURE:
<223> OTHER INFORMATION: human VH1-f (DP-3)

<400> SEQUENCE: 32

Glu Val Gln Leu Val Gln Ser Gly Ala Glu Val Lys Lys Pro Gly Ala
1               5               10              15
Thr Val Lys Ile Ser Cys Lys Val Ser Gly Tyr Thr Phe Thr Asp Tyr
            20              25              30
Tyr Met His Trp Val Gln Gln Ala Pro Gly Lys Gly Leu Glu Trp Met
        35              40              45
Gly Leu Val Asp Pro Glu Asp Gly Glu Thr Ile Tyr Ala Glu Lys Phe
    50              55              60
Gln Gly Arg Val Thr Ile Thr Ala Asp Thr Ser Thr Asp Thr Ala Tyr
65              70              75              80
Met Glu Leu Ser Ser Leu Arg Ser Glu Asp Thr Ala Val Tyr Tyr Cys
                85              90              95
Ala Thr

<210> SEQ ID NO 33
<211> LENGTH: 98
<212> TYPE: PRT
<213> ORGANISM: Artificial Sequence
<220> FEATURE:
<223> OTHER INFORMATION: human VH7-81

<400> SEQUENCE: 33

Gln Val Gln Leu Val Gln Ser Gly His Glu Val Lys Gln Pro Gly Ala
1               5               10              15
Ser Val Lys Val Ser Cys Lys Ala Ser Gly Tyr Ser Phe Thr Thr Tyr
            20              25              30
Gly Met Asn Trp Val Pro Gln Ala Pro Gly Gln Gly Leu Glu Trp Met
        35              40              45
Gly Trp Phe Asn Thr Tyr Thr Gly Asn Pro Thr Tyr Ala Gln Gly Phe
    50              55              60
Thr Gly Arg Phe Val Phe Ser Met Asp Thr Ser Ala Ser Thr Ala Tyr
65              70              75              80
Leu Gln Ile Ser Ser Leu Lys Ala Glu Asp Met Ala Met Tyr Tyr Cys
                85              90              95
Ala Arg

<210> SEQ ID NO 34
<211> LENGTH: 98
```

-continued

```
<212> TYPE: PRT
<213> ORGANISM: Artificial Sequence
<220> FEATURE:
<223> OTHER INFORMATION: human VH5-51 (DP-73)

<400> SEQUENCE: 34

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 35
<211> LENGTH: 100
<212> TYPE: PRT
<213> ORGANISM: Artificial Sequence
<220> FEATURE:
<223> OTHER INFORMATION: human VH2-05

<400> SEQUENCE: 35

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 36
<211> LENGTH: 100
<212> TYPE: PRT
<213> ORGANISM: Artificial Sequence
<220> FEATURE:
<223> OTHER INFORMATION: human VH2-70 (DP-28)

<400> SEQUENCE: 36

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Cys Val Ser Trp Ile Arg Gln Pro Pro Gly Lys Ala Leu Glu
            35                  40                  45

Trp Leu Ala Leu Ile Asp Trp Asp Asp Asp Lys Tyr Tyr Ser Thr Ser
        50                  55                  60
```

```
Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

<210> SEQ ID NO 37
<211> LENGTH: 100
<212> TYPE: PRT
<213> ORGANISM: Artificial Sequence
<220> FEATURE:
<223> OTHER INFORMATION: human VH2-26 (DP-26)

<400> SEQUENCE: 37

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile
            100
```

<210> SEQ ID NO 38
<211> LENGTH: 97
<212> TYPE: PRT
<213> ORGANISM: Artificial Sequence
<220> FEATURE:
<223> OTHER INFORMATION: human VH4-04

<400> SEQUENCE: 38

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

<210> SEQ ID NO 39
<211> LENGTH: 97
<212> TYPE: PRT
<213> ORGANISM: Artificial Sequence
<220> FEATURE:
<223> OTHER INFORMATION: human VH4-59 (DP-71)

-continued

```
<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 40
<211> LENGTH: 99
<212> TYPE: PRT
<213> ORGANISM: Artificial Sequence
<220> FEATURE:
<223> OTHER INFORMATION: human VH4-61 (DP-66)

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 41
<211> LENGTH: 99
<212> TYPE: PRT
<213> ORGANISM: Artificial Sequence
<220> FEATURE:
<223> OTHER INFORMATION: human VH4-39 (DP-79)

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg

<210> SEQ ID NO 42
<211> LENGTH: 99
<212> TYPE: PRT
<213> ORGANISM: Artificial Sequence
<220> FEATURE:
<223> OTHER INFORMATION: human VH4-31 (DP-65)

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 43
<211> LENGTH: 98
<212> TYPE: PRT
<213> ORGANISM: Artificial Sequence
<220> FEATURE:
<223> OTHER INFORMATION: human VH4-28 (DP-68)

<400> SEQUENCE: 43

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 44
<211> LENGTH: 97
<212> TYPE: PRT
<213> ORGANISM: Artificial Sequence
<220> FEATURE:
<223> OTHER INFORMATION: human VH4-34 (DP-63)

<400> SEQUENCE: 44

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 45
<211> LENGTH: 101
<212> TYPE: PRT
<213> ORGANISM: Artificial Sequence
<220> FEATURE:
<223> OTHER INFORMATION: human VH6-01 (DP-74)

<400> SEQUENCE: 45

Gln Val Gln Leu Gln Gln Ser Gly Pro Gly Leu Val Lys Pro Ser Gln
1                   5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
                100

<210> SEQ ID NO 46
<211> LENGTH: 100
<212> TYPE: PRT
<213> ORGANISM: Artificial Sequence
<220> FEATURE:
<223> OTHER INFORMATION: human VH3-15 (DP-38)

<400> SEQUENCE: 46

Glu Val Gln Leu Val Glu Ser Gly Gly Gly Leu Val Lys Pro Gly Gly
1                   5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
                100

<210> SEQ ID NO 47
<211> LENGTH: 100

```
<212> TYPE: PRT
<213> ORGANISM: Artificial Sequence
<220> FEATURE:
<223> OTHER INFORMATION: human VH3-49

<400> SEQUENCE: 47

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 48
<211> LENGTH: 100
<212> TYPE: PRT
<213> ORGANISM: Artificial Sequence
<220> FEATURE:
<223> OTHER INFORMATION: human VH3-72 (DP-29)

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 49
<211> LENGTH: 100
<212> TYPE: PRT
<213> ORGANISM: Artificial Sequence
<220> FEATURE:
<223> OTHER INFORMATION: human VH3-73

<400> SEQUENCE: 49

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
```

-continued

```
        50              55              60

Ser Val Lys Gly Arg Phe Thr Ile Ser Arg Asp Asp Ser Lys Asn Thr
65                  70              75              80

Ala Tyr Leu Gln Met Asn Ser Leu Lys Thr Glu Asp Thr Ala Val Tyr
                85              90              95

Tyr Cys Thr Arg
            100

<210> SEQ ID NO 50
<211> LENGTH: 98
<212> TYPE: PRT
<213> ORGANISM: Artificial Sequence
<220> FEATURE:
<223> OTHER INFORMATION: human VH3-16

<400> SEQUENCE: 50

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Asn Ser
                20              25              30

Asp Met Asn Trp Ala Arg Lys Ala Pro Gly Lys Gly Leu Glu Trp Val
            35              40              45

Ser Gly Val Ser Trp Asn Gly Ser Arg Thr His Tyr Val Asp Ser Val
            50              55              60

Lys Arg Arg Phe Ile Ile Ser Arg Asp Asn Ser Arg Asn Ser Leu Tyr
65              70              75              80

Leu Gln Lys Asn Arg Arg Arg Ala Glu Asp Met Ala Val Tyr Tyr Cys
                85              90              95

Val Arg

<210> SEQ ID NO 51
<211> LENGTH: 98
<212> TYPE: PRT
<213> ORGANISM: Artificial Sequence
<220> FEATURE:
<223> OTHER INFORMATION: human VH3-35 (DP-59)

<400> SEQUENCE: 51

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Asn Ser
                20              25              30

Asp Met Asn Trp Val His Gln Ala Pro Gly Lys Gly Leu Glu Trp Val
            35              40              45

Ser Gly Val Ser Trp Asn Gly Ser Arg Thr His Tyr Ala Asp Ser Val
            50              55              60

Lys Gly Arg Phe Ile Ile Ser Arg Asp Asn Ser Arg Asn Thr Leu Tyr
65                  70              75              80

Leu Gln Thr Asn Ser Leu Arg Ala Glu Asp Thr Ala Val Tyr Tyr Cys
                85              90              95

Val Arg

<210> SEQ ID NO 52
<211> LENGTH: 99
<212> TYPE: PRT
<213> ORGANISM: Artificial Sequence
<220> FEATURE:
<223> OTHER INFORMATION: human VH3-09 (DP-31)
```

-continued

```
<400> SEQUENCE: 52

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 53
<211> LENGTH: 98
<212> TYPE: PRT
<213> ORGANISM: Artificial Sequence
<220> FEATURE:
<223> OTHER INFORMATION: human VH3-20 (DP-32)

<400> SEQUENCE: 53

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 54
<211> LENGTH: 99
<212> TYPE: PRT
<213> ORGANISM: Artificial Sequence
<220> FEATURE:
<223> OTHER INFORMATION: human VH3-43 (DP-33)

<400> SEQUENCE: 54

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95
```

Ala Lys Asp

<210> SEQ ID NO 55
<211> LENGTH: 98
<212> TYPE: PRT
<213> ORGANISM: Artificial Sequence
<220> FEATURE:
<223> OTHER INFORMATION: human VH3-07 (DP-54)

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 56
<211> LENGTH: 98
<212> TYPE: PRT
<213> ORGANISM: Artificial Sequence
<220> FEATURE:
<223> OTHER INFORMATION: human VH3-30 (DP-49)

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 57
<211> LENGTH: 98
<212> TYPE: PRT
<213> ORGANISM: Artificial Sequence
<220> FEATURE:
<223> OTHER INFORMATION: human VH3-33 (DP-50)

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

-continued

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 58
<211> LENGTH: 98
<212> TYPE: PRT
<213> ORGANISM: Artificial Sequence
<220> FEATURE:
<223> OTHER INFORMATION: human VH3-74 (DP-53)

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 59
<211> LENGTH: 97
<212> TYPE: PRT
<213> ORGANISM: Artificial Sequence
<220> FEATURE:
<223> OTHER INFORMATION: human VH3-13 (DP-48)

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 60
<211> LENGTH: 98
<212> TYPE: PRT
<213> ORGANISM: Artificial Sequence
<220> FEATURE:
<223> OTHER INFORMATION: human VH3-11 (DP-35)

<400> SEQUENCE: 60

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 61
<211> LENGTH: 98
<212> TYPE: PRT
<213> ORGANISM: Artificial Sequence
<220> FEATURE:
<223> OTHER INFORMATION: human VH3-21 (DP-77)

<400> SEQUENCE: 61

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 62
<211> LENGTH: 98
<212> TYPE: PRT
<213> ORGANISM: Artificial Sequence
<220> FEATURE:
<223> OTHER INFORMATION: human VH3-48 (DP-51)

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Asp Glu Asp Thr Ala Val Tyr Tyr Cys
            85                  90                  95

Ala Arg

<210> SEQ ID NO 63
<211> LENGTH: 98
<212> TYPE: PRT
<213> ORGANISM: Artificial Sequence
<220> FEATURE:
<223> OTHER INFORMATION: human VH3-23 (DP-47)

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 64
<211> LENGTH: 98
<212> TYPE: PRT
<213> ORGANISM: Artificial Sequence
<220> FEATURE:
<223> OTHER INFORMATION: human VH3-64

<400> SEQUENCE: 64

Glu Val Gln Leu Val Glu Ser Gly Glu Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
            85                  90                  95

Ala Arg

<210> SEQ ID NO 65
<211> LENGTH: 96
<212> TYPE: PRT
<213> ORGANISM: Artificial Sequence
<220> FEATURE:
<223> OTHER INFORMATION: human VH3-38

<400> SEQUENCE: 65

Glu Val Gln Leu Val Glu Ser Gly Gly Gly Leu Val Gln Pro Arg Gly
1               5                   10                  15
```

```
Ser Leu Arg Leu Ser Cys Ala Ala Ser Gly Phe Thr Val Ser Ser Asn
        20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
        50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Gly Thr Ala Val Tyr Tyr Cys Ala Arg
                85                  90                  95
```

```
<210> SEQ ID NO 66
<211> LENGTH: 97
<212> TYPE: PRT
<213> ORGANISM: Artificial Sequence
<220> FEATURE:
<223> OTHER INFORMATION: human VH3-53 (DP-42)

<400> SEQUENCE: 66

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
        20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

```
<210> SEQ ID NO 67
<211> LENGTH: 97
<212> TYPE: PRT
<213> ORGANISM: Artificial Sequence
<220> FEATURE:
<223> OTHER INFORMATION: human VH3-66

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
        20                  25                  30

Tyr Met Ser Trp Val Arg Gln Ala Pro Gly Lys Gly Leu Glu Trp Val
        35                  40                  45

Ser Val Ile Tyr Ser Cys Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

```
<210> SEQ ID NO 68
<211> LENGTH: 18
<212> TYPE: PRT
```

```
<213> ORGANISM: Artificial Sequence
<220> FEATURE:
<223> OTHER INFORMATION: chicken JH gene segment

<400> SEQUENCE: 68

Thr Ala Gly Ser Ile Asp Ala Trp Gly His Gly Thr Glu Val Ile Val
1               5                   10                  15

Ser Ser

<210> SEQ ID NO 69
<211> LENGTH: 17
<212> TYPE: PRT
<213> ORGANISM: Artificial Sequence
<220> FEATURE:
<223> OTHER INFORMATION: human JH gene segment

<400> SEQUENCE: 69

Ala Glu Tyr Phe Gln His Trp Gly Gln Gly Thr Leu Val Thr Val Ser
1               5                   10                  15

Ser

<210> SEQ ID NO 70
<211> LENGTH: 17
<212> TYPE: PRT
<213> ORGANISM: Artificial Sequence
<220> FEATURE:
<223> OTHER INFORMATION: human JH gene segment

<400> SEQUENCE: 70

Tyr Trp Tyr Phe Asp Leu Trp Gly Arg Gly Thr Leu Val Thr Val Ser
1               5                   10                  15

Ser

<210> SEQ ID NO 71
<211> LENGTH: 16
<212> TYPE: PRT
<213> ORGANISM: Artificial Sequence
<220> FEATURE:
<223> OTHER INFORMATION: human JH gene segment

<400> SEQUENCE: 71

Asp Ala Phe Asp Ile Trp Gly Gln Gly Thr Met Val Thr Val Ser Ser
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: human JH gene segment

<400> SEQUENCE: 72

Tyr Phe Asp Tyr Trp Gly Gln Gly Thr Leu Val Thr Val Ser Ser
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: human JH gene segment

<400> SEQUENCE: 73

Asn Trp Phe Asp Pro Trp Gly Gln Gly Thr Leu Val Thr Val Ser Ser
1               5                   10                  15
```

```
<210> SEQ ID NO 74
<211> LENGTH: 20
<212> TYPE: PRT
<213> ORGANISM: Artificial Sequence
<220> FEATURE:
<223> OTHER INFORMATION: human JH gene segment

<400> SEQUENCE: 74

Tyr Tyr Tyr Tyr Tyr Tyr Met Asp Val Trp Gly Lys Gly Thr Thr Val
1               5                   10                  15

Thr Val Ser Ser
            20

<210> SEQ ID NO 75
<211> LENGTH: 710
<212> TYPE: DNA
<213> ORGANISM: Gallus gallus

<400> SEQUENCE: 75
acgcgctaac gaagccggag ccctccttat gcaaattagc ccctccagag ggccataaaa      60
gcgccggctc tccgacggag gagcaccagt cggctccgca accatgagcc cactcgtctc     120
ctccctcctg ctcctggccg ccctgccagg tgagggcgct gtggggctct atggggctct     180
atggggtctc agcggggctc tgcgggctca atggggggcca aaggggggggt ctgcgggctc     240 tatgggggggg tcaacggggg gtctcacggg gggccggctc cgcgaggccg tgtggcggcg     300
gctccgtcag cgctctctgt ccttccccac agggctgatg gcggccgtga cgttggacga     360 gtccggggggc ggcctccaga cgcccggaag agcgctcagc ctcgtctgca aggcctccgg     420
gttcaccttc agcagttaca acatgggttg ggtgcgacag gcgcccggca aggggctgga     480
gttcgtcgct ggtattgaca cactggtag atacacaggc tacgggtcgg cggtgaaggg     540
ccgtgccacc atctcgaggg acaacgggca gagcacagtg aggctgcagc tgaacaacct     600
cagggctgag gacaccggca cctactactg cgccaaagct gctggtcacg gtgacaccga     660
tccccagcac gggtggcaca aaacccaccg ttgcaaccca aggcggtgaa     710

<210> SEQ ID NO 76
<211> LENGTH: 120
<212> TYPE: PRT
<213> ORGANISM: Gallus gallus

<400> SEQUENCE: 76

Met Ser Pro Leu Val Ser Ser Leu Leu Leu Leu Ala Ala Leu Pro Gly
1               5                   10                  15

Leu Met Ala Ala Val Thr Leu Asp Glu Ser Gly Gly Gly Leu Gln Thr
            20                  25                  30

Pro Gly Arg Ala Leu Ser Leu Val Cys Lys Ala Ser Gly Phe Thr Phe
        35                  40                  45

Ser Ser Tyr Asn Met Gly Trp Val Arg Gln Ala Pro Gly Lys Gly Leu
    50                  55                  60

Glu Phe Val Ala Gly Ile Asp Asn Thr Gly Arg Tyr Thr Gly Tyr Gly
65                  70                  75                  80

Ser Ala Val Lys Gly Arg Ala Thr Ile Ser Arg Asp Asn Gly Gln Ser
                85                  90                  95

Thr Val Arg Leu Gln Leu Asn Asn Leu Arg Ala Glu Asp Thr Gly Thr
            100                 105                 110

Tyr Tyr Cys Ala Lys Ala Ala Gly
```

```
                115                     120

<210> SEQ ID NO 77
<211> LENGTH: 215
<212> TYPE: DNA
<213> ORGANISM: Gallus gallus

<400> SEQUENCE: 77
gttggatggc caaaaaacgg ttgttttttt tttttttttaa ccaaaatggg cggttttcgc      60
ccgaaaagag tgggtggagt ttttgggtga aaaaaggcgg attttggggc attgtggtac      120
tgctggtagc atcgacgcat ggggccacgg gaccgaagtc atcgtctcct ccggtgagtc      180 ttcaacccccc cccaaaattg ccgcggcgat tttgg                                 215

<210> SEQ ID NO 78
<211> LENGTH: 18
<212> TYPE: PRT
<213> ORGANISM: Gallus gallus

<400> SEQUENCE: 78

Thr Ala Gly Ser Ile Asp Ala Trp Gly His Gly Thr Glu Val Ile Val
1               5                   10                  15

Ser Ser

<210> SEQ ID NO 79
<211> LENGTH: 18
<212> TYPE: PRT
<213> ORGANISM: Artificial Sequence
<220> FEATURE:
<223> OTHER INFORMATION: forward primer chVH-FW annotation

<400> SEQUENCE: 79

Val Leu Ala Thr Ala Ala Gln Pro Ala Met Ala Ala Val Thr Leu Asp
1               5                   10                  15

Glu Ser

<210> SEQ ID NO 80
<211> LENGTH: 63
<212> TYPE: DNA
<213> ORGANISM: Artificial Sequence
<220> FEATURE:
<223> OTHER INFORMATION: past of vector MV1511

<400> SEQUENCE: 80
ggattgttat tactcgcggc ccagccggcc atggcgatgc ctgcttgccg aatatcatgg      60
tgg                                                                     63

<210> SEQ ID NO 81
<211> LENGTH: 63
<212> TYPE: DNA
<213> ORGANISM: Artificial Sequence
<220> FEATURE:
<223> OTHER INFORMATION: part of the functional chicken VH

<400> SEQUENCE: 81
cagcgctctc tgtccttccc cacagggctg atggcggccg tgacgttgga cgagtccggg      60
ggc                                                                     63

<210> SEQ ID NO 82
<211> LENGTH: 24
<212> TYPE: DNA
<213> ORGANISM: Artificial Sequence
```

```
<220> FEATURE:
<223> OTHER INFORMATION: reverse complement of chVH-RV reverse primer
<220> FEATURE:
<221> NAME/KEY: CDS
<222> LOCATION: (1)..(24)

<400> SEQUENCE: 82 ggg acc gag gtc acc gtc tcc tcc                                         24
Gly Thr Glu Val Thr Val Ser Ser
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Construct

<400> SEQUENCE: 83

Gly Thr Glu Val Thr Val Ser Ser
1               5

<210> SEQ ID NO 84
<211> LENGTH: 63
<212> TYPE: DNA
<213> ORGANISM: Artificial Sequence
<220> FEATURE:
<223> OTHER INFORMATION: part of vector MV1511

<400> SEQUENCE: 84
aagtacgccc cctattgacg tcaatgacgg tcaccgtctc gagcgcctcc accaagggcc      60
cat                                                                    63

<210> SEQ ID NO 85
<211> LENGTH: 63
<212> TYPE: DNA
<213> ORGANISM: Artificial Sequence
<220> FEATURE:
<223> OTHER INFORMATION: part of chicken JH gene segment

<400> SEQUENCE: 85
gcatcgacgc atggggccac gggaccgaag tcatcgtctc ctccggtgag tcttcaaccc      60
ccc                                                                    63

<210> SEQ ID NO 86
<211> LENGTH: 15
<212> TYPE: DNA
<213> ORGANISM: Artificial Sequence
<220> FEATURE:
<223> OTHER INFORMATION: nonsense sequence

<400> SEQUENCE: 86
aaaaaaaaaa aaaaa                                                        15

<210> SEQ ID NO 87
<211> LENGTH: 107
<212> TYPE: PRT
<213> ORGANISM: Artificial Sequence
<220> FEATURE:
<223> OTHER INFORMATION: common light chain variable region
     IgVk3-15/IGJk1

<400> SEQUENCE: 87

Glu Ile Val Met Thr Gln Ser Pro Ala Thr Leu Ser Val Ser Pro Gly
1               5                   10                  15
```

```
Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105
```

```
<210> SEQ ID NO 88
<211> LENGTH: 108
<212> TYPE: PRT
<213> ORGANISM: Artificial Sequence
<220> FEATURE:
<223> OTHER INFORMATION: common light chain variable region
      IgVk3-20/IGJk1

<400> SEQUENCE: 88
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

```
<210> SEQ ID NO 89
<211> LENGTH: 108
<212> TYPE: PRT
<213> ORGANISM: Artificial Sequence
<220> FEATURE:
<223> OTHER INFORMATION: common light chain variable region
      IgVl3-21/IGJl3

<400> SEQUENCE: 89
```

```
Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95
```

```
Trp Val Phe Gly Gly Gly Thr Lys Leu Thr Val Leu
            100                     105

<210> SEQ ID NO 90
<211> LENGTH: 95
<212> TYPE: PRT
<213> ORGANISM: Artificial Sequence
<220> FEATURE:
<223> OTHER INFORMATION: Variable gene region sequence IgVk3-15

<400> SEQUENCE: 90

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
            85                  90                  95

<210> SEQ ID NO 91
<211> LENGTH: 96
<212> TYPE: PRT
<213> ORGANISM: Artificial Sequence
<220> FEATURE:
<223> OTHER INFORMATION: Variable gene region sequence IgVk3-20

<400> SEQUENCE: 91

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
            85                  90                  95

<210> SEQ ID NO 92
<211> LENGTH: 225
<212> TYPE: PRT
<213> ORGANISM: Artificial Sequence
<220> FEATURE:
<223> OTHER INFORMATION: heavy chain variable region of the chicken Fab
      region PDB 4GLR and a human constant region CH1

<400> SEQUENCE: 92

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Leu Ser Ser Tyr
            20                  25                  30

Gln Met Met Trp Val Arg Gln Ala Pro Gly Lys Gly Leu Glu Trp Val
        35                  40                  45
```

-continued

```
Ala Gly Ile Thr Ser Arg Gly Gly Val Thr Gly Tyr Gly Ser Ala Val
    50              55                  60

Lys Gly Arg Ala Thr Ile Ser Arg Asp Asn Gly Gln Ser Thr Val Arg
65              70                  75                  80

Leu Gln Leu Asn Asn Leu Arg Ala Glu Asp Thr Gly Thr Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly His Gly Thr Glu Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Arg
    210                 215                 220

Val
225
```

```
<210> SEQ ID NO 93
<211> LENGTH: 215
<212> TYPE: PRT
<213> ORGANISM: Artificial Sequence
<220> FEATURE:
<223> OTHER INFORMATION: human kappa light chain IgVk1-39/IGJk5/Ckappa

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 94
<211> LENGTH: 214
<212> TYPE: PRT
<213> ORGANISM: Artificial Sequence
<220> FEATURE:
<223> OTHER INFORMATION: human kappa light chain IgVk3-15/IGJk1/Ckappa

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 95
<211> LENGTH: 215
<212> TYPE: PRT
<213> ORGANISM: Artificial Sequence
<220> FEATURE:
<223> OTHER INFORMATION: human kappa light chain IgVk3-20/IGJk1/Ckappa

<400> SEQUENCE: 95

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50              55              60
Gly Ser Gly Ser Gly Thr Asp Phe Thr Leu Thr Ile Ser Arg Leu Glu
65              70              75              80
Pro Glu Asp Phe Ala Val Tyr Tyr Cys Gln Gln Tyr Gly Ser Ser Pro
                85              90              95
Trp Thr Phe Gly Gln Gly Thr Lys Val Glu Ile Lys Arg Thr Val Ala
            100             105             110
Ala Pro Ser Val Phe Ile Phe Pro Pro Ser Asp Glu Gln Leu Lys Ser
        115             120             125
Gly Thr Ala Ser Val Val Cys Leu Leu Asn Asn Phe Tyr Pro Arg Glu
    130             135             140
Ala Lys Val Gln Trp Lys Val Asp Asn Ala Leu Gln Ser Gly Asn Ser
145             150             155             160
Gln Glu Ser Val Thr Glu Gln Asp Ser Lys Asp Ser Thr Tyr Ser Leu
                165             170             175
Ser Ser Thr Leu Thr Leu Ser Lys Ala Asp Tyr Glu Lys His Lys Val
            180             185             190
Tyr Ala Cys Glu Val Thr His Gln Gly Leu Ser Ser Pro Val Thr Lys
        195             200             205
Ser Phe Asn Arg Gly Glu Cys
    210             215

<210> SEQ ID NO 96
<211> LENGTH: 214
<212> TYPE: PRT
<213> ORGANISM: Artificial Sequence
<220> FEATURE:
<223> OTHER INFORMATION: human lambda light chain IgVl3-21/IGJl3/Clambda

<400> SEQUENCE: 96

Ser Tyr Val Leu Thr Gln Pro Pro Ser Val Ser Val Ala Pro Gly Glu
1               5               10              15
Thr Ala Arg Ile Thr Cys Gly Gly Asp Asn Ile Gly Arg Lys Ser Val
            20              25              30
Tyr Trp Tyr Gln Gln Lys Ser Gly Gln Ala Pro Val Leu Val Ile Tyr
        35              40              45
Tyr Asp Ser Asp Arg Pro Ser Gly Ile Pro Glu Arg Phe Ser Gly Ser
    50              55              60
Asn Ser Gly Asn Thr Ala Thr Leu Thr Ile Ser Arg Val Glu Ala Gly
65              70              75              80
Asp Glu Ala Asp Tyr Tyr Cys Gln Val Trp Asp Gly Ser Ser Asp His
                85              90              95
Trp Val Phe Gly Gly Gly Thr Lys Leu Thr Val Leu Gly Gln Pro Lys
            100             105             110
Ala Ala Pro Ser Val Thr Leu Phe Pro Pro Ser Ser Glu Glu Leu Gln
        115             120             125
Ala Asn Lys Ala Thr Leu Val Cys Leu Ile Ser Asp Phe Tyr Pro Gly
    130             135             140
Ala Val Thr Val Ala Trp Lys Ala Asp Ser Ser Pro Val Lys Ala Gly
145             150             155             160
Val Glu Thr Thr Thr Pro Ser Lys Gln Ser Asn Asn Lys Tyr Ala Ala
                165             170             175
Ser Ser Tyr Leu Ser Leu Thr Pro Glu Gln Trp Lys Ser His Arg Ser
            180             185             190
```

Tyr Ser Cys Gln Val Thr His Glu Gly Ser Thr Val Glu Lys Thr Val
        195                     200                 205

Ala Pro Thr Glu Cys Ser
        210

<210> SEQ ID NO 97
<211> LENGTH: 96
<212> TYPE: PRT
<213> ORGANISM: Artificial Sequence
<220> FEATURE:
<223> OTHER INFORMATION: Variable gene region sequence IgVl3-21

<400> SEQUENCE: 97

Ser Tyr Val Leu Thr Gln Pro Pro Ser Val Ser Val Ala Pro Gly Glu
1                   5                   10                  15

Thr Ala Arg Ile Thr Cys Gly Gly Asp Asn Ile Gly Arg Lys Ser Val
                20                  25                  30

Tyr Trp Tyr Gln Gln Lys Ser Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95

<210> SEQ ID NO 98
<211> LENGTH: 118
<212> TYPE: PRT
<213> ORGANISM: Artificial Sequence
<220> FEATURE:
<223> OTHER INFORMATION: Human control MF1025 VH sequence

<400> SEQUENCE: 98

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Trp Trp Ala Thr Phe Asp Tyr Trp Gly Gln Gly Thr
                100                 105                 110

Leu Val Thr Val Ser Ser
        115

<210> SEQ ID NO 99
<211> LENGTH: 359
<212> TYPE: PRT
<213> ORGANISM: Mus musculus

<400> SEQUENCE: 99

Met Glu Pro Ile Ser Val Ser Ile Tyr Thr Ser Asp Asn Tyr Ser Glu
1                   5                   10                  15

```
Glu Val Gly Ser Gly Asp Tyr Asp Ser Asn Lys Glu Pro Cys Phe Arg
         20                  25                  30

Asp Glu Asn Val His Phe Asn Arg Ile Phe Leu Pro Thr Ile Tyr Phe
         35                  40                  45

Ile Ile Phe Leu Thr Gly Ile Val Gly Asn Gly Leu Val Ile Leu Val
         50                  55                  60

Met Gly Tyr Gln Lys Lys Leu Arg Ser Met Thr Asp Lys Tyr Arg Leu
65                  70                  75                  80

His Leu Ser Val Ala Asp Leu Leu Phe Val Ile Thr Leu Pro Phe Trp
              85                  90                  95

Ala Val Asp Ala Met Ala Asp Trp Tyr Phe Gly Lys Phe Leu Cys Lys
             100                 105                 110

Ala Val His Ile Ile Tyr Thr Val Asn Leu Tyr Ser Ser Val Leu Ile
             115                 120                 125

Leu Ala Phe Ile Ser Leu Asp Arg Tyr Leu Ala Ile Val His Ala Thr
         130                 135                 140

Asn Ser Gln Arg Pro Arg Lys Leu Leu Ala Glu Lys Ala Val Tyr Val
145                 150                 155                 160

Gly Val Trp Ile Pro Ala Leu Leu Leu Thr Ile Pro Asp Phe Ile Phe
             165                 170                 175

Ala Asp Val Ser Gln Gly Asp Ile Ser Gln Gly Asp Asp Arg Tyr Ile
             180                 185                 190

Cys Asp Arg Leu Tyr Pro Asp Ser Leu Trp Met Val Val Phe Gln Phe
             195                 200                 205

Gln His Ile Met Val Gly Leu Ile Leu Pro Gly Ile Val Ile Leu Ser
         210                 215                 220

Cys Tyr Cys Ile Ile Ile Ser Lys Leu Ser His Ser Lys Gly His Gln
225                 230                 235                 240

Lys Arg Lys Ala Leu Lys Thr Thr Val Ile Leu Ile Leu Ala Phe Phe
             245                 250                 255

Ala Cys Trp Leu Pro Tyr Tyr Val Gly Ile Ser Ile Asp Ser Phe Ile
             260                 265                 270

Leu Leu Gly Val Ile Lys Gln Gly Cys Asp Phe Glu Ser Ile Val His
             275                 280                 285

Lys Trp Ile Ser Ile Thr Glu Ala Leu Ala Phe Phe His Cys Cys Leu
         290                 295                 300

Asn Pro Ile Leu Tyr Ala Phe Leu Gly Ala Lys Phe Lys Ser Ser Ala
305                 310                 315                 320

Gln His Ala Leu Asn Ser Met Ser Arg Gly Ser Ser Leu Lys Ile Leu
             325                 330                 335

Ser Lys Gly Lys Arg Gly Gly His Ser Ser Val Ser Thr Glu Ser Glu
             340                 345                 350

Ser Ser Ser Phe His Ser Ser
             355
```

```
<210> SEQ ID NO 100
<211> LENGTH: 134
<212> TYPE: PRT
<213> ORGANISM: Artificial Sequence
<220> FEATURE:
<223> OTHER INFORMATION: VH region of CXCR4-1

<400> SEQUENCE: 100
```

```
Ala Val Thr Leu Asp Glu Ser Gly Gly Gly Leu Gln Thr Pro Gly Gly
1                   5                  10                  15
```

```
Ala Leu Ser Leu Val Cys Lys Ala Ser Gly Phe Thr Phe Ser Ser Tyr
            20                  25                  30

Arg Gly Met His Trp Val Arg Gln Ala Pro Gly Lys Gly Leu Glu Trp
            35                  40                  45

Val Ala Gly Ile Tyr Ser Ser Gly Ser Ser Thr Ala Tyr Gly Ala Ala
    50                  55                  60

Val Lys Gly Arg Ala Thr Ile Ser Arg Asp Asp Gly Gln Ser Thr Val
65                  70                  75                  80

Arg Leu Gln Leu Asn Asn Leu Arg Ala Glu Asp Thr Gly Thr Tyr Tyr
                85                  90                  95

Cys Ala Lys Asp Ala Gly Ser Cys Trp Tyr Gly Arg Arg Ser Gly Phe
            100                 105                 110

Asn Cys Asp Pro Tyr Gly Gly Asn Ile Asp Ala Trp Gly His Gly Thr
            115                 120                 125

Glu Val Ile Val Ser Ser
    130
```

<210> SEQ ID NO 101
<211> LENGTH: 134
<212> TYPE: PRT
<213> ORGANISM: Artificial Sequence
<220> FEATURE:
<223> OTHER INFORMATION: VH region of CXCR4-2

<400> SEQUENCE: 101

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Ser Phe Ser Ser Tyr
            20                  25                  30

Asp Met Ser Trp Val Arg Gln Ala Pro Gly Lys Gly Leu Glu Trp Val
            35                  40                  45

Ala Gly Ile Tyr Ser Ile Gly Arg Asp Ala Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Glu Ser Gly Ser Ala Cys Arg Tyr Ala Ala Arg His Gly Tyr
            100                 105                 110

Ile Cys Ala Gly Tyr Leu Gly Ser Ile Asp Ala Trp Gly His Gly Thr
            115                 120                 125

Glu Val Ile Val Ser Ser
    130
```

<210> SEQ ID NO 102
<211> LENGTH: 137
<212> TYPE: PRT
<213> ORGANISM: Artificial Sequence
<220> FEATURE:
<223> OTHER INFORMATION: VH region of CXCR4-3

<400> SEQUENCE: 102

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Ser Ile Gly Ser Tyr
            20                  25                  30

Gly Met Gly Trp Val Arg Gln Ala Pro Gly Lys Gly Leu Glu Phe Val
```

-continued

```
          35                   40                   45

Ala Gly Ile Ser Thr Ile Gly Gly Val Thr Trp Tyr Gly Ala Ala Val
     50                   55                   60

Lys Gly Arg Ala Ile Ile Ser Arg Asp Asn Gly Gln Ser Thr Val Arg
65                   70                   75                   80

Leu Gln Leu Asn Asn Leu Arg Ala Glu Asp Thr Gly Thr Tyr Phe Cys
              85                   90                   95

Ala Lys Ala Ser Asp Ser Pro Ser Cys Arg Tyr Gly Ser Arg Ser Gly
              100                  105                  110

Trp Ser Cys Pro Gly Trp Asn Tyr Gly Gly Arg Ile Asp Ala Trp Gly
         115                  120                  125

His Gly Thr Glu Val Ile Val Ser Ser
    130                  135
```

MIXED BINDING DOMAINS

CROSS-REFERENCE TO RELATED APPLICATIONS

This application is a U.S. national stage filing of International Application No. PCT/NL2019/050877, filed Dec. 27, 2019; which claims priority to EP Application No. 18215995.4, filed Dec. 31, 2018. The entire contents of International Application No. PCT/NL2019/050877 and EP Application No. 18215995.4 are hereby incorporated herein by reference.

REFERENCE TO A SEQUENCE LISTING SUBMITTED ELECTRONICALLY VIA EFS-WEB

The content of the electronically submitted sequence listing in ASCII text file (Name: 4096_0360001_Seqlisting_ST25.txt; Size: 93,536 bytes; and Date of Creation: Jun. 21, 2021) filed with the application is incorporated herein by reference in its entirety.

The invention relates to a binding domain or multimer or a variant thereof, and to methods for making such a binding domain or multimer or a variant thereof. The binding domain or multimer or a variant thereof comprises a variable region based on, derived or obtained from an animal phylogenetically distal to a human, wherein such variable region pairs with a human variable region of a cognate chain. The invention also relates to a phage or other organism suitable for peptide display, which comprises in its genome a nucleic acid encoding a binding domain or multimer, or a variant thereof; to a display library which comprises a plurality of such organisms and to a method for the preparation of such a display library. Further, the invention relates to host cells that produce such a binding domain or multimer, or a variant thereof. Further, the invention relates to a pharmaceutical composition which comprises the binding domain or multimer or a variant thereof; to its use in the treatment of the human or animal by therapy; and to a method for the treatment of a human or animal suffering from a medical indication using the binding domain or multimer or a variant thereof.

BACKGROUND

The development of hybridoma technology by Kohler and Milstein opened the door to the use of antibodies for the prevention and treatment of human disease and mice became a frequent choice for the generation of antibodies.

Originally, attempts were made to use mice antibodies directly for human therapy. After experience with a human anti-mouse antibody (HAMA) response, which caused an immunogenic response to the administration of mice antibodies to humans leading to illness and potentially death, transgenic mice were developed having immune systems, harboring nucleic acid encoding human variable and/or constant regions, which are capable of generating antibodies, which could then be analyzed for the development of human therapeutics. Similarly, phage display libraries were generated with human immunoglobulin encoding nucleic acids. Such humanized mice and phage display libraries have been responsible for contributing to an array of successful therapeutic antibodies on the market today, with many more in clinical development.

Human transgenic animals have also been described previously, which harbor nucleic acid encoding a human common immunoglobulin chain comprising a rearranged light or heavy variable chain, and encoding an unrearranged variable region of the cognate chain(s) in the germline of such animals. Such transgenic animals are capable of producing antibodies having diversity generated through one of the two cognate chains of the immunoglobulin, e.g., the unrearranged heavy or light chain, which undergoes somatic recombination during B-cell development and affinity maturation after antigen exposure. These transgenic animals, such as MeMo® mice (e.g. WO2009/15771), are capable of producing diverse repertoires of antibodies against an array of antigens, where the nucleic acids encoding or based on, for example, the heavy chain variable regions of such repertoires against different antigens or epitopes of the same antigen can then be combined into host cells that encode large panels of bispecific antibodies, Biclonics®. These cells can be readily screened for the efficient production of bispecific antibodies having differentiated and novel biology (e.g. WO2017/069628).

Whilst humanized transgenic mice have led to medical breakthroughs and offer promise for further advances, in view of the evolutionary similarity between mice and humans, there can be epitopes on antigens that are immunologically blind to humans (e.g., self-antigens), which may similarly be immunologically blind to transgenic mice or other animals evolutionarily similar to humans.

Since humans and mice share many conserved domains for a given antigen, this may lead to instances when immunization of such transgenic animals may give rise to antibodies at low levels or none at all without additional labor at modifying the transgenic animal or engaging in potentially laborious immunization protocols.

Similarly, there are instances where immunization of the transgenic organism generates antibodies, but where such antibodies are not cross-reactive for a human and transgenic animal, making the assaying and testing of such antibodies less efficient. Further, there are more rare instances where immunization of wild-type animals, such as rodents or mice, and immunization of transgenic animals with humanized immune systems with the same target may yield antibody repertoires comprised of antibodies that bind similar epitopes across species.

Accordingly, there is a need for the generation of therapeutic antibodies that recognize novel epitopes on human antigens.

SUMMARY OF THE INVENTION

Without being bound to any theory, the present inventors believe that the evolutionary similarity between humans and the animal immunized, where such an animal is evolutionarily proximate to humans, may lead to an immune response in such an animal, which develops antibodies targeting the same or similar epitopes to those antibodies produced by the human repertoire, leading potentially to novel or neoepitopes not being identified by such transgenic animals. That is to say, generally, evolutionary similarity results in antibody repertoires that recognize epitopes that are different between the species and not typically antibodies that recognize epitopes that are similar or identical between species.

Accordingly, it may be beneficial to obtain binding domains or antibodies, including chimeric or humanized binding domains or antibodies, that contain variable regions and/or complementary determining regions (CDR), and the nucleic acids that encode said variable regions, that are based on, derived or obtained from a nucleic acid of species that are evolutionarily distant to humans. This may allow novel antibodies to be generated, including those capable of binding epitopes not readily identified by human, humanized or chimeric antibodies having variable regions from human and more evolutionarily proximate species (e.g., rodent and other mammalian species). Use of evolutionarily distant species for the production of binding domains or antibodies harboring variable regions and nucleic acids that encode them, which are based on, derived or obtained from a nucleic acid of such species also offers advantages in the capability of generating antibodies that are human, murine and cyno-molgus cross-reactive.

One potential source of such variable regions may be birds, for example domesticated birds, such as chickens, ducks and ostriches, which can readily be bred and immunized in a controlled environment. Birds have not shared a common ancestor with humans in more than 300 million years and are among the few known survivors of the Archosaurs group of animals. The variable region and immune system of this group, which is evolutionarily distal to humans, renders its immune response suitable for the generation of titers of antibodies capable of binding therapeutic targets that are conserved, and may be immunologically blind or impaired, among mammals (e.g., humans, rodent, and cynomolgus). Moreover, antibody repertoires generated via immunization of birds, for example chickens, ducks and ostriches, may identify unique epitopes when compared to antibodies generated via the immunization of mice or other species evolutionarily close to humans (e.g., rodents and cynomolgus).

Without being bound to any theory, this may be due to the evolutionary distance between humans and birds, such as chickens. For example, different amino acid usage in chicken complementary determining regions (CDRs), as exemplified by an unusually low representation of tyrosine and an unusually high representation of cysteine in chicken HCDR3 sequences, and different immunogenic response of the repertoire to antigens than occurs with respect to humans (and evolutionarily more related species) to the same antigens offer the capacity to generate antibodies that are unique in comparison to the human immune response or the immune response of classical transgenic animals employed, such as mice, rats or rabbits among other animals.

Previously, the risk of immunogenicity with use of antibodies harboring variable regions and/or CDRs based on, derived or obtained from a nucleic acid of animals highly unrelated to humans, for example chicken antibodies, has been understood to be an impediment to the use of such antibodies, more so than with more evolutionarily proximate species such as mice. Humanization of polypeptides of antibodies having sequences based on, derived or obtained from a nucleic acid of birds, whereby the variable region or complementary determining region of such antibodies may be grafted on to a human antibody format, has been understood to be an impediment to rendering such antibodies or antibodies comprising such variable regions from being used in a human clinical development or therapeutic setting.

Moreover, the ability to combine bird (e.g., chicken) antibody variable regions or antibody domains with human antibody formats to generate chimeric chicken/human antibodies has been considered an arduous and uncertain exercise with a potential for destabilization and/or loss of affinity and efficacy of such antibodies from such repertoires, again limiting the usefulness of the benefits of utilizing such antibodies and hosts to generate antibodies.

Thus, for at least the reasons provided above, binding domains or multimers, including antibodies, and variants thereof, which comprise variable regions based on, derived or obtained from a nucleic acid of animals evolutionarily distal to humans paired with human variable regions of a cognate chain; and the methods of making such binding domains, or multimers, including antibodies; nucleic acids that encode them; the production of display libraries that present variable regions of such binding domains; the screening of such binding domains or multimers, including antibodies; making of host cells that produce them; and pharmaceuticals comprising them, are highly desirable and are an advance in the art and such inventions are set out here.

Despite the evolutionary distance between birds and humans that has diversified many proteins, and despite the fact that the limited number of functional VH gene segments of species of birds do not share significant homology at the primary amino acid sequence with human VH gene segments, the inventors have identified that chicken, duck and ostrich VH gene segments share significant tertiary structural similarity with human VH gene segments when analyzing the rearranged variable regions.

For example, we have generated a 3D homology model of a human/chicken hybrid Fab generated based on the crystal structure of a human Fab having MF3178 (PDB entry 5O4O) comprising a heavy chain variable region having an amino acid sequence set forth in SEQ ID NO: 1 and a light chain variable region having an amino acid sequence set forth in SEQ ID NO: 7, which binds Her3. MF3178 is derived from a parental VH1-02 variable gene segment and comprises a human common light chain. In the model, the human VH region was replaced by a modeled VH region based on the amino acid sequence of a chicken VH region taken from the structure of a chicken Fab. Analysis of the model showed 24 non-bonded electrostatic interactions present between the chicken VH region and human common light chain interface, whereas 20 non-bonded electrostatic interactions were identified in the fully human interface of MF3178 and light chain. This indicates that the interface between a chicken VH and human VL is complimentary and that the human/chicken hybrid Fab is stabilized by these interactions and may be more stable than the fully human Fab. This is especially surprising given the low level of primary amino acid sequence homology, only 43% sequence identity, between the functional chicken V gene segment and the human VH1-02 gene segment from which the MF3178 exemplified herein originates.

Accordingly, the present inventors herein describe binding domains comprising rearranged VH regions generated by birds that are directly paired with human VL regions to form a new type of hybrid or chimeric binding domain. Fabs comprising such VH and VL regions can be generated, the CH1 and CL regions of which can both be human or both be of an animal evolutionarily distant to human (such as birds, including chickens, ducks or ostriches). It is also possible that the CH1 region is of the evolutionarily distant animal and the CL region is human. It may also be possible that the CH1 region is human and the CL region is of the evolutionarily distant animal.

For example, chicken heavy chain variable regions, share homology at the tertiary structure level with human heavy chain variable regions, such that chicken rearranged VH regions isolated from an immunized chicken may be directly paired, with human variable light (VL) regions, and preferably a VL region which may serve as a common chain, for generating panels of binding domains, multimers, antibodies, or variants, wherein the diversity of such domains and capacity to bind to an antigen of interest is primarily due to the chicken heavy chain variable region. Such mixed binding domains can be stably formed without the requirement that the bird variable region and human variable region co-evolve during B-cell maturation, but rather can be readily combined into a mixed binding domain by use of, for example, a wild-type rearranged bird heavy chain variable region and pairing it with a human light chain, preferably a human common light chain. This technology permits the production of display libraries that permit the large scale screening of such mixed binding domains for the potential identification of novel binding of known antigens and mixed binding domains that may be cross-reactive across mammalian species.

In this way, it is possible to directly generate chimeric binding domains, multimers and antibodies from the pairing of human variable regions, such as a human heavy or light chain variable region, preferably a human common heavy or common light chain variable region, with a rearranged variable heavy or light chain variable regions of birds, such as chicken, ducks and ostriches. The use of a human light chain variable region, preferably a human common light chain variable region, and not a cognate bird light chain variable region is preferred. First, by using a human common light chain variable region, half the binding domain is immediately humanized. Second, by use of a human common light chain variable region, wild type bird heavy chain variable regions are identified which pair with the human common light chain variable region, and are then capable of being used for the efficient generation of antibodies, in particular bispecific antibodies, or multivalent multimers.

A Fab is composed of a heavy and light chain part that should together make a domain structure that does not unfold and it is unexpected that this works to form a stable binding domain when heavy and light chains from evolutionarily distant species are combined. The use of display technology allows the identification of heavy chain variable region chains from animals phylogenetically distally related to humans which are capable of binding an antigen (used to immunize said animals) in the context of a (common) light chain derived from another antibody/animal/species.

Surprisingly, as described herein, nucleic acids encoding heavy chain variable regions from antibody repertoires from animals distally related to humans that bind to an antigen of interest, are capable of pairing with a human light chain. This results in a stable VH/VL interface capable of binding the antigen bound by an antibody comprising the native VH/VL pairing.

A nucleic acid that encodes these binding domains (comprised of a human variable region on the one hand paired with a bird variable region on the other) can be readily integrated into a host cell. Such a host cell may then express one or more heavy chain variable domains alongside a common human light chain, which permits the production of large panels of multimers, including multispecific antibodies, that are capable of binding a diverse array of antigens, including those that target epitopes which may not readily be identified by panels of antibodies based on or derived from human variable gene segments or variable gene segments based on or derived from species more evolutionarily proximate to humans, such as rodents, and other mammals. Furthermore, such binding domains comprised of paired variable regions from an animal distally related to a human paired with a human variable region, are more readily cross reactive to antigens present in a range of mammals (including murine, human and cynomolgus) than entirely human variable regions, or antibodies having variable regions based on, derived or obtained from a nucleic acid of immunized animals more phylogenetically close to humans.

Applicants have previously described the capability to express bispecific and multispecific antibodies from host cells containing a nucleic acid encoding two or more diverse immunoglobulin variable chains (heavy or light variable chains) and a common variable chain (heavy or light common variable chain), and the manner in which such variable chains can be paired to preferentially produce such bispecific and multispecific antibodies over homodimer antibodies by use of engineering of the Fc region, including CH3 engineering to drive the formation of heavy chain heterodimers (WO2013/157954). Other means of producing heterodimerization of different heavy chains, including through CH3 engineering charge differential or knob-in-hole are likewise known in the art.

Accordingly, an invention disclosed herein relates to binding domains and multimers, such as antibodies, which comprise a common variable region or common chain, typically a human common variable region or common chain, and a cognate variable region or cognate chain encoded by a nucleic acid based on, derived or obtained from a nucleic acid of an organism phylogenetically distal to a human, such as a bird. For example, the common chain may be a common light chain (cLC), such as a human common light chain, and the cognate variable region may be a heavy chain variable region (VH) encoded by a nucleic acid based on, derived or obtained from a nucleic acid of a bird, including a chicken, duck and ostrich.

Pairing a human light chain variable region, preferably a human common light chain variable region, with VH regions encoded by nucleic acid(s) based on, derived or obtained from a nucleic acid of bird (or vice versa) facilitates the production of binding domains, multimers and antibodies which may access epitopes which are not accessible or bound through traditional antibody generation platforms, including use of human synthetic phage display libraries and transgenic organisms harboring humanized immune systems.

Furthermore, the generation of binding domains, multimers and antibodies comprising variable regions from an animal phylogenetically distal from a human, preferably from a bird such as a chicken, paired with a human chain, preferably a human common chain, is useful for the generation of bispecific and multispecific multimers, including antibodies and variants. The use of a human chain, preferably a human common chain, allows half of the binding domain immediately to be humanized.

An animal phylogenetically distal from a human may be referred to herein as "an animal suitable for use in the invention".

As in all higher vertebrates, primary diversity in bird (such as a chicken) VH/VL regions is created by V(D)J recombination, followed by affinity maturation.

In contrast to humans and mammals such as mice, which have multiple functional V, D and J gene segments available for V(D)J recombination, a variety of birds, for example chickens, ducks and ostriches, contain only a limited number of functional gene segments each for VH, JH, VL and JL, in addition to a set of functional D gene segments. Indeed, chickens and ostriches have only one functional V gene segment. Ducks, for example, may have as few as one or two functional heavy chain V gene segments.

Additional diversification of the immune repertoire is generated in chickens due to a gene conversion process in which the recombined VH and VL regions are diversified via homologous recombination with a set of pseudogenes that comprise (part of) the corresponding V(D) sequences. These non-functional pseudogenes lack recombination signal sequences, promoters, signal peptides and Kozak translation initiation sites. Combined with somatic hypermutation of the generated VH and VL regions, this process leads to chicken antibody repertoires that have highly diverse CDRs, whereas the framework (FW) sequences remain very similar to the original functional genes; no or limited mutations are introduced in FW4 since chickens do not have JH/JL pseudogenes. In chickens, the main antibody isotype is IgY, which is structurally and functionally similar to IgG in mammals and therefore often mislabeled as IgG (Renaud et al., Cell 40, 283-291, 1985; Renaud et al., Cell 48, 379-388, 1987; Renaud et al., Cell 59, 171-183, 1989; and Wu et al., The Journal of Immunology 188, 322-333, 2012).

We have produced and herein disclose a 3D homology model of a human/chicken hybrid Fab generated (see the Examples below) based on the crystal structure of human Fab MF3178 (PDB entry 5O4O), which binds Her3 and where the VH region based on the amino acid sequence has the sequence set out in SEQ ID NO: 1. MF3178 is derived from a parental VH1-02 variable gene segment and is paired with an IgVκ1-39*01/IGJκ1*01 common light chain.

(SEQ ID NO: 1)
QVQLVQSGAEVKKPGASVKVSCKASGYTFTGYYMHWVRQAPGQGLEWMG

WINPNSGGTNYAQKFQGRVTMTRDTSISTAYMELSRLRSDDTAVYYCAR

DHGSRHFWSYWGFDYWGQGTLVTVSS

In the model, the human VH region was replaced by a modeled VH region based on the amino acid sequence of a chicken VH region (SEQ ID NO: 2) taken from the structure of a chicken Fab (PDB 4GLR; Shih et al. J. Biological Chemistry 287, 44425-44434, 2012). Surprisingly, analysis of the model showed 24 non-bonded electrostatic interactions present between the chicken VH region and the IgVκ1-39*01/IGJκ1*01 common light chain interface, whereas 20 non-bonded electrostatic interactions are identified in the fully human interface of MF3178 (see FIG. 4a) and light chain. Accordingly, described herein is a mixed binding domain obtained from a wildtype chicken variable region directly paired to a human cognate variable region, having a high number of contact residues and electrostatic interactions capable of forming a stable interface.

At the chimeric chicken VH region/human cLC interface, ten (10) of the electrostatic interactions are identical compared with the interface of the human VH and VL interface of the human Fab comprising a heavy chain variable region with SEQ ID NO: 1 and light chain variable region with SEQ ID NO: 7, and two (2) of the interactions between the chicken VH region and human common light chain are formed between homologous residues found at the equivalent positions in the chicken VH region and human VH region of the human Fab comprising a heavy chain variable region with SEQ ID NO:1 and light chain variable region with SEQ ID NO:7. Further, more hydrogen bonds—twelve (12) instead of six (6)—are present in the chicken VH region/human common light chain interface compared to the human VH/VL interaction of the human Fab comprising a heavy chain variable region with SEQ ID NO:1 and light chain variable region with SEQ ID NO: 7, indicating greater stability potential between the chicken VH region and human VL interface than for the fully human binding domain of the human Fab comprising a heavy chain variable region with SEQ ID NO: 1 and light chain variable region with SEQ ID NO:7.

Similarly, we demonstrate, that for ducks, which have a limited functional V gene segment, a rearranged heavy chain variable region creates an interface with a human cLC to generate a variety of contact points and electrostatic interactions. The human VH was replaced by a modeled VH based on the amino acid sequence of a duck VH taken from the structure of amino acids 1 to 133 of Genbank accession no. A46529 (SEQ ID NO: 3).

Surprisingly, the analysis of the model showed 28 non-bonded electrostatic interactions present between the duck VH region and the human IgVκ1-39*01/IGJκ1*01 common light chain variable region interface, compared to the 20 non-bonded electrostatic interactions identified in the fully human interface of the human Fab comprising a heavy chain variable region with SEQ ID NO: 1 and light chain variable region with SEQ ID NO: 7 (see FIG. 10a) with 12 of those interactions being identical and one equivalent when comparing the duck heavy/human light to the human heavy/human light found at the same positions of the human Fab comprising a heavy chain variable region with SEQ ID NO: 1 and light chain variable region with SEQ ID NO: 7.

It is further demonstrated that for ostrich, which have a limited functional V gene segment, a rearranged heavy chain variable region of an ostrich creates an interface with a human cLC to generate a variety of contact points and electrostatic interactions. The human VH was replaced by a modeled VH region based on the amino acid sequence of an ostrich VH region taken from the structure of Genbank accession no. AFN02388.1 (SEQ ID NO: 4), and 14 non-bonded electrostatic interactions are present between the ostrich VH region and common light chain interface.

At the chimeric ostrich VH region/human cLC interface, seven (7) of the electrostatic interactions are identical compared with the human VH and VL of the human Fab comprising a heavy chain variable region with SEQ ID NO: 1 and light chain variable region with SEQ ID NO: 7, and one (1) of the interactions between the ostrich VH region and human VL are formed between homologous residues found at human heavy/human light chains at the same positions of the human Fab comprising a heavy chain variable region with SEQ ID NO: 1 and light chain variable region with SEQ ID NO: 7.

Accordingly, the inventors have determined that recombined and affinity matured heavy chain variable regions of birds, for example, chicken heavy chain variable regions, may be directly paired with a human light chain variable region, preferably a common light chain variable region or common light chain, more preferably a germline light chain variable region or light chain, for example, IgVκ1-39*01/IGJκ1*01, to obtain functional binding domains, for example Fab, F(ab')n or scFv domains, including for generation of bivalent and multivalent antibodies and other multimers, without the need for co-evolution of the chicken VH and human VL through B-cell development and affinity maturation occurring in, for example, a transgenic organism, or extensive antibody engineering.

In principle, following the techniques and teaching set out here, one can take any evolutionarily distant animal, for example birds, such as chicken, antibody and replace the cognate chicken light chain or light chain variable region with a human light chain or light chain variable region, in particular a human common light chain or human common light chain variable region.

Structural homology between recombined and affinity matured heavy chain variable regions of birds and a human variable region of a light chain, in particular a common light chain, thus allows chimeric libraries to be generated from which antibodies may be selected in which the heavy chain variable region of the bird is dominant for affinity and specificity. The generation of libraries comprised of a human common chain and paired with a wild-type bird rearranged chain, permits the identification of those latter chains that are capable of specifically binding an antigen of interest, in the absence of being paired to its wild-type cognate chain. Thus, this library permits the identification of said heavy chains and nucleic acids that encode them for efficient generation of bispecific antibodies or multivalent multimers.

That is to say, an invention disclosed herein comprises a new mixed binding domain, for example, which may take the form of a multimer or an antibody, which comprises a VH region encoded by a nucleic acid based on, derived or obtained from a nucleic acid of an animal which is phylogenetically distal from a human, such as a bird, paired with a human VL region. Typically, such an animal is one which has only a limited repertoire of V gene segments, for example one, two, three or four heavy chain V gene segments. It may, for instance, also be an animal having V regions that have structural similarity to human V regions.

Preferably, such binding domain comprises a human light chain, for example a human common light chain, more preferably a germline light chain variable region or light chain, for example, IgV$_K$1-39*01/IGJ$_K$1*01. Such a binding domain, or antibody, multimer or variant incorporating such a binding domain, may be directly suitable for use as a therapeutic, or subject to a further humanization, including CDR grafting, and other modifications.

According to the invention, there is thus provided a binding domain, multimer, antibody or a variant thereof which comprises a variable region encoded by a nucleic acid based on, derived or obtained from, at least in part, a nucleic acid of an animal phylogenetically distal from a human ("an animal suitable for use in the invention"), which variable region is paired with a human variable region.

In such a binding domain, the number of contact points between the VH region of an animal suitable for use in the invention and a human VL may be substantially similar to and/or preferably at least as many as exist between a human VH region and a human VL binding domain, such as exemplified herein for a human Fab comprising a heavy chain variable region with SEQ ID NO: 1 and light chain variable region with SEQ ID NO: 7.

A repertoire of such binding domains, multimers, antibodies or variants may be made, for example in the form of a library. A repertoire of such binding domains, multimers, antibodies or variants may also be made, for example, by replacing the cognate light chain or light chain variable region of an antibody of an animal suitable for use in the invention with a human light chain or light chain variable region, in particular a human common light chain or human common light chain variable region. Binding domains, multimers, antibodies or variants may be selected having a desired specificity.

According to an invention disclosed herein, there is thus provided a binding domain, multimer, antibody or a variant thereof which comprises a variable region encoded by a nucleic acid based on, derived or obtained from, at least in part, a nucleic acid of an animal phylogenetically distal from a human, which variable region is paired with a human variable region. The invention also includes repertoires of such binding domains, multimers, antibodies or variants.

According to an invention disclosed herein, there is thus provided a binding domain, multimer, antibody or a variant thereof which comprises a variable region encoded by a nucleic acid based on, derived or obtained from, at least in part, a nucleic acid of an animal phylogenetically distal from a human paired with a human variable region, wherein such binding domain comprises 4, preferably 5, preferably 8 and more preferably 10 or more electrostatic interactions that are identical or equivilant to the electrostatic interactions present in a human heavy/human light chain variable region interface of a binding domain, such as exemplified herein fora human Fab comprising a heavy chain variable region with SEQ ID NO: 1 and light chain variable region with SEQ ID NO: 7.

Said animal phylogenetically distal from a human may be a bird as described above, preferably a chicken, duck and ostrich.

The invention also provides: a method for the preparation of a mixed binding domain, which method comprises:

exposing an animal phylogenetically distal from a human, such as a bird, to an antigen;

isolating nucleic acid encoding heavy or light chain variable regions from such animal; and pairing the heavy or light chain variable region encoded by the isolated nucleic acid with a human heavy or light chain variable region, thereby forming a mixed binding domain.

The mixed binding domain can be used for the preparation of an antibody or variant thereof, in particular a multispecific antibody, such as for instance a bispecific or trispecific antibody.

The invention also provides: a method for the preparation of an antibody or variant thereof, which method comprises:

exposing an animal phylogenetically distal from a human, such as a bird to an antigen;

isolating nucleic acid sequences encoding heavy or light chain variable regions from such animal which are capable of binding the antigen; and preparing a display library in which the heavy or light chain variable regions are encoded by genetic material isolated, based on, derived or obtained from a nucleic acid of the bird and wherein said heavy or light chain variable regions are paired with a human cognate chain variable region forming a mixed binding domain.

Said library may be comprised of phage, yeast, ribosomes, or other vessels for peptide display known in the art.

A library of the invention, for example a phage display library, may be used to identify or select, heavy or light chain variable regions from a bird capable of binding with a cognate chain variable region. Selection is carried out to determine which heavy or light chains from a bird within the library, when combined to a human (common) light or heavy chain are capable of binding the antigen ultimately used to immunize the bird.

The invention also provides:

a phage of the invention comprising in its genome: a nucleic acid sequence encoding a heavy chain variable region based on, derived or obtained at least in part from a heavy chain region of a bird; and a nucleic acid sequence encoding a human light chain variable region;

phage display library which comprises a plurality of phages of the invention;

a method for the preparation of a phage display library, which method comprises: immunizing a bird with an antigen;

isolating a plurality of nucleic acid sequences encoding heavy chain variable regions from such animal which are capable of binding the antigen; and preparing a phage display library using the nucleic acid sequences, thereby to prepare a phage display library;

a method for the preparation of a phage display library, which method comprises:

immunizing a bird with an antigen, wherein such animal comprises a functional VH gene segment, comprising 5, preferably 8 and more preferably 10 electrostatic interactions with a human VL variable region at the VH/VL interface;

isolating a plurality of nucleic acid sequences encoding heavy chain variable regions from such animal which are capable of binding the antigen; and preparing a phage display library using the nucleic acid sequences, thereby to prepare a phage display library;

a method for the identification of a binding domain or a multimer or a variant thereof by using the phage display library of the invention;

a host cell comprising a nucleic acid encoding two or more heavy chain variable regions based on, derived or obtained, at least in part, from a nucleic acid of a bird which are capable of binding an epitope paired with a human light chain, preferably wherein each encoded heavy chain variable regions is capable of binding the same or different targets or epitopes on a target;

a nucleic acid encoding two or more heavy chain variable regions based on, derived or obtained, at least in part, from a nucleic acid of a bird which are capable of binding an epitope paired with a human light chain, capable of expression and multimerization to form a variable binding domain, preferably a multimer, antibody or variant thereof, and more preferably a multispecific multimer, antibody or variant thereof;

a pharmaceutical composition which comprises an antibody according to any one of the invention and a pharmaceutically acceptable carrier and/or diluent;

an antibody of the invention for use in the treatment of the human or animal body by therapy; and a method for the treatment of a human or animal suffering from a medical indication, which method comprises administering to the human or animal a therapeutically effective amount of an antibody of the invention.

BRIEF DESCRIPTION OF THE DRAWINGS

FIG. 2 sets out a protein sequence alignment of the amino acid sequences encoded by the chicken VH1 gene segment and human VH1-02 gene segment. CDR residues according to Kabat numbering are shown with dashed lines.

FIG. 3 sets out a protein sequence alignment of the amino acid sequences encoded by the only functional chicken JH and the six (6) human JH gene segments. CDR residues according to Kabat numbering are shown with dashed lines.

4A) provides an analysis of non-covalent, electrostatic interactions in human Fab MF3178 targeting Her3 (PDB 5O4O) comprising heavy chain variable region (SEQ ID NO: 1) and light chain variable region of the IgV$_K$1-39*01/

IGJ$_K$1*01 common light chain (SEQ ID NO: 7) and compares this to a hybrid homology model in which the amino acid sequence of the human VH of MF3178 was replaced by the corresponding sequence of a chicken VH region (SEQ ID NO: 2; PDB 4GLR). Asterisks indicate if interaction between amino acids in the human Fab interface is identical or equivalent to the interaction between amino acids of the chicken VH region (SEQ ID NO: 2) and light chain variable region of the IgV$_K$1-39*01/IGJ$_K$1*01 common light chain (SEQ ID NO: 7) in the chimeric Fab. Twenty-four (24) electrostatic interactions between the chicken VH region and human common light chain variable region are observed in comparison with twenty (20) interactions in the human VH/human cLC interface, with thirteen (13) of the interactions between the chicken VH/human cLC interface being the equivalent or identical to the human VH/human cLC of MF3178. The upper Table shows the total non-bonded interactions (hydrogen bonds, salt bridges and hydrophobic interactions) between the VH and VL for the hybrid model (chicken VH-human VL), and for the human Fab (human VH-human VL). It lists the identical interactions (exact same residues involved) and the equivalent (same position with different residue). Chain A is the light chain. Chain B is the heavy chain. Kabat numbering used.

4B) Left: Structure alignment of the tertiary structure of the human VH/human cLC interface of MF3178 is provided (PDB 5O4O; light grey) and overlayed on the hybrid homology model of the chicken VH region/human VL interface (dark grey) evidencing a high degree of structural similarity. Non-bonded interactions between residues from the VH regions and the VL are shown as dashed lines (black for MF3178, grey for the homology model).

4B) Right: Depiction of the hydrogen bond formed between Thr110 and Gln12 in the homology model is provided, comparing the tertiary structure of the human VH/human cLC interface of MF3178 (PDB 5O4O; light grey), overlayed on the hybrid homology model of the chicken VH region/human cLC interface (dark grey). The model of the VH of the chicken Fab (PDB 4GLR) is modified to reflect a I110T positional change, which is done to reflect the introduction of a BstEII cloning site at the nucleic acid level. The introduction of the 111 OT positional change conserves the hydrogen bond formed with Gln12 on the opposite beta strand.

4C) Structure alignment of VL-VH regions of human Fab MF3178 (PDB 5O4O) in light grey and a chicken Fab (PDB 4GLR) in dark grey is provided, evidencing the similar conformational interaction between the human VH/VL of MF3178, and the chimeric chicken VH (SEQ ID NO: 2) and light chain variable region of the Vk1-39 cLC (SEQ ID NO: 7) interface.

Figure 5:
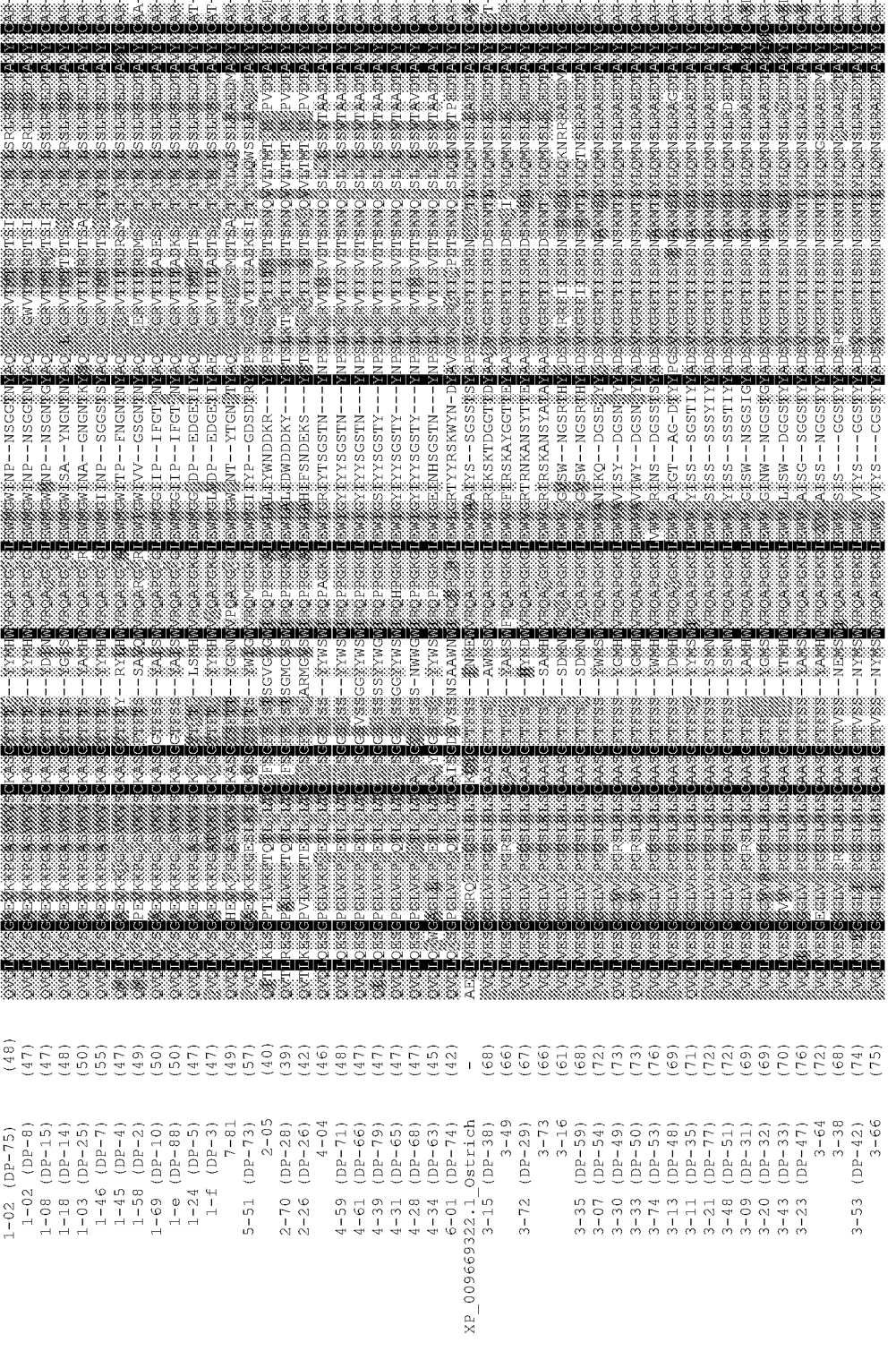

FIG. 5 sets out a protein sequence alignment of the amino acid sequences encoded by the one putative functional ostrich VH gene segment (XP_009669322.1—SEQ ID NO: 13) with 47 human germline VH gene segments that represent each of the 7 VH families obtained via AlignX. Percentage identity for each human VH gene segment is given between brackets. AlignX is a component of Vector NTI Advance 11.5.2 software, and alignment is obtained using default settings.

Figure 6:
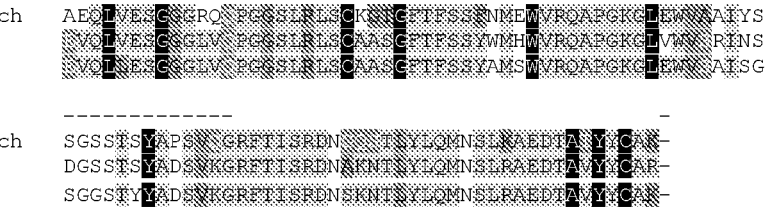

FIG. 6 sets out a protein sequence alignment of the amino acid sequences encoded by the ostrich VH gene segment (XP_009669322.1—SEQ ID NO: 13) and human VH3-23 and human VH3-74 gene segments. CDR residues according to Kabat numbering are underlined.

FIG. 7A provides an analysis of non-covalent, electrostatic interactions in human Fab MF3178 targeting Her3

(PDB 5O4O) comprising heavy chain variable region (SEQ ID NO: 1) and light chain variable region of the IgV$_K$1-39*01/IGJ$_K$1*01 common light chain (SEQ ID NO: 7) and compares this to a hybrid homology model in which the amino acid sequence of the human VH region of MF3178 was replaced by the corresponding sequence of an ostrich VH region (SEQ ID NO: 4). Asterisks indicate if interaction between amino acids in the MF3178 interface is identical or equivalent to the interaction between amino acids of the ostrich VH region (SEQ ID NO: 4) and light chain variable region of the IgV$_K$1-39*01/IGJ$_K$1*01 common light chain (SEQ ID NO: 7). Fourteen (14) electrostatic interactions at the ostrich VH region and human common light chain region are observed in comparison with twenty (20) interactions in the human VH/human cLC interface, with eight (8) of the interactions between the ostrich VH/human cLC interface being the equivalent or identical to the human VH/human cLC of MF3178. The upper Table shows the total non-bonded interactions (hydrogen bonds, salt bridges and hydrophobic interactions) between the VH and VL and for the hybrid model (chicken VH-human VL), and for the human Fab (human VH-human VL). It lists the identical interactions (exact same residues involved) and the equivalent (same position with different residue). Chain A is the light chain. Chain B is the heavy chain. Kabat numbering used.

7B) sets out the chimeric binding domain comprised of the ostrich heavy chain variable region, and human CH1 paired with the common light chain, including the variable region of the IgV$_K$1-39*01/IGJ$_K$1*01 common light chain (SEQ ID NO: 5—the full length common light chain sequence including the CL region).

7C) sets out the electrostatic interactions at the ostrich heavy chain variable region, human common light chain region interface and shows a graphical representation of the interactions set out in FIG. 7a.

Figure 8:
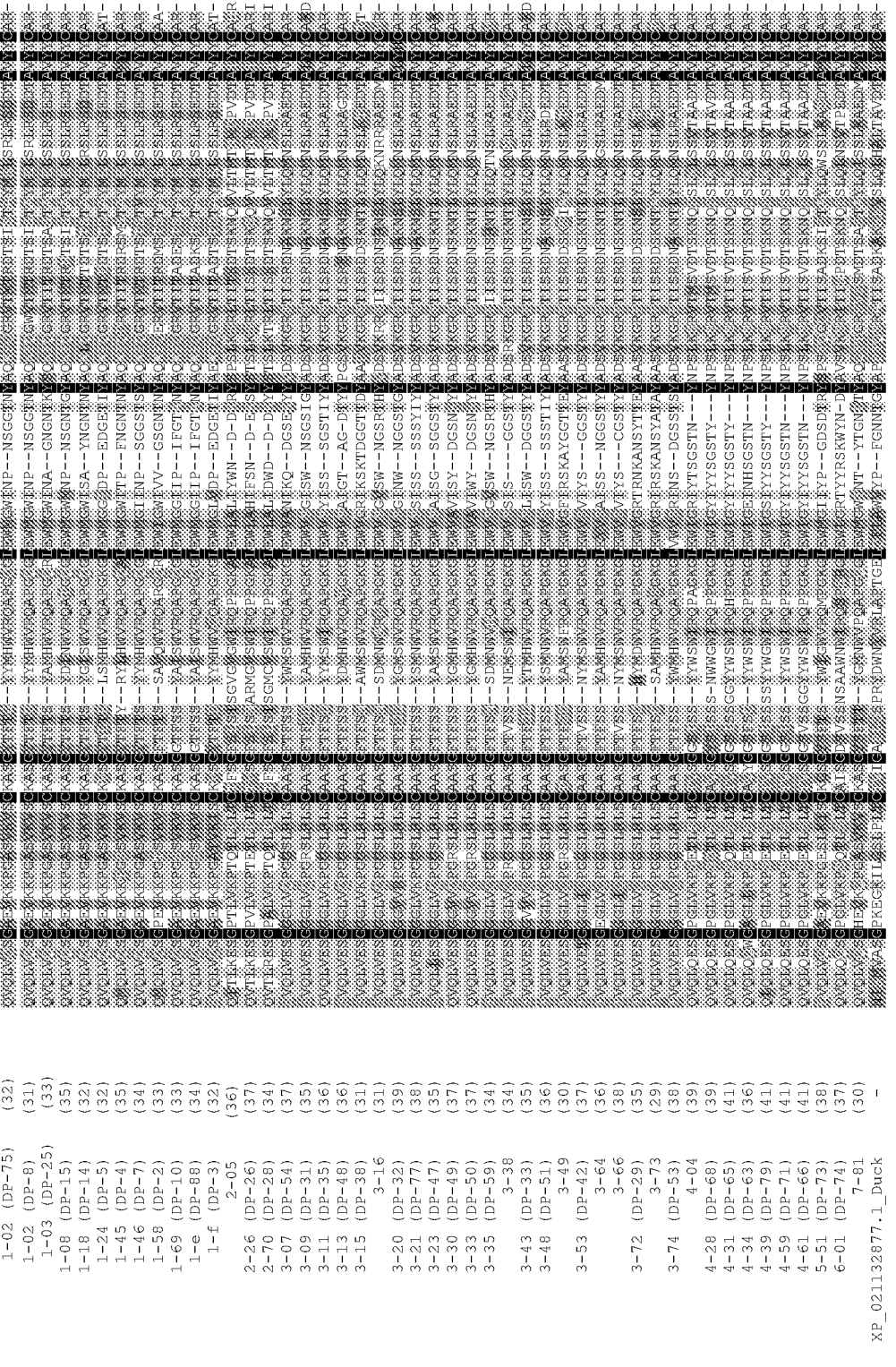

FIG. 8 sets out a protein sequence alignment of the amino acid sequences encoded by one putative functional duck VH gene segment (XP_021132877.1—SEQ ID NO: 12) with 47 human germline VH gene segments that represent each of the 7 VH families obtained via AlignX. Percentage identity for each human VH gene segment is given between brackets. AlignX is a component of Vector NTI Advance 11.5.2 software, and alignment is obtained using default settings.

Figure 9:

FIG. 9 sets out a protein sequence alignment of the amino acid sequences encoded by the duck VH gene segment (XP_021132877.1—SEQ ID NO: 12) and human VH4-59, VH4-61, VH4-39 and VH4-31 gene segments. CDR residues according to Kabat numbering are underlined.

FIG. 10A provides an analysis of non-covalent, electrostatic interactions in human Fab MF3178 targeting Her3 (PDB 5O4O) comprising heavy chain variable region (SEQ ID NO: 1) and light chain variable region of the IgV$_K$1-39*01/IGJ$_K$1*01 common light chain (SEQ ID NO: 7) and compares this to a hybrid homology model in which the amino acid sequence of the human VH region of MF3178 was replaced by the corresponding sequence of a duck VH region (SEQ ID NO: 3). Asterisks indicate if interaction between amino acids in the MF3178 interface is identical or equivalent to the interaction between amino acids of the duck VH (SEQ ID NO: 3) and light chain variable region of the IgV$_K$1-39*01/IGJ$_K$1*01 common light chain (SEQ ID NO: 7). Twenty-eight (28) electrostatic interactions at the duck VH region and human common light chain region are observed in comparison with twenty (20) interactions in the human VH/human cLC interface, with thirteen (13) of the interactions between the duck VH/human cLC interface being the equivalent or identical to the human VH/human cLC of MF3178. The upper Table shows the total non-bonded interactions (hydrogen bonds, salt bridges and hydrophobic interactions) between the VH and VL for the hybrid model (duck VH-human VL), and for the human Fab (human VH-human VL). It lists the identical interactions (exact same residues involved) and the equivalent (same position with different residue). Chain A is the light chain. Chain B is the heavy chain. Kabat numbering used.

Figure 10B:
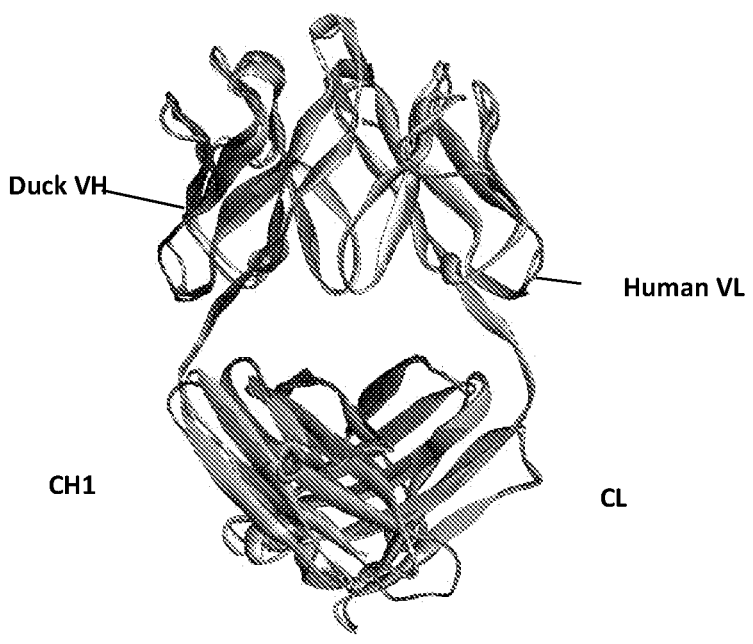

FIG. 10B) sets out the mixed binding domain comprised of the duck heavy chain variable region, and human CH1 paired with the human common light chain, including the variable region IgV$_K$1-39*01/IGJ$_K$1*01 (SEQ ID NO: 5).

Figure 10C:
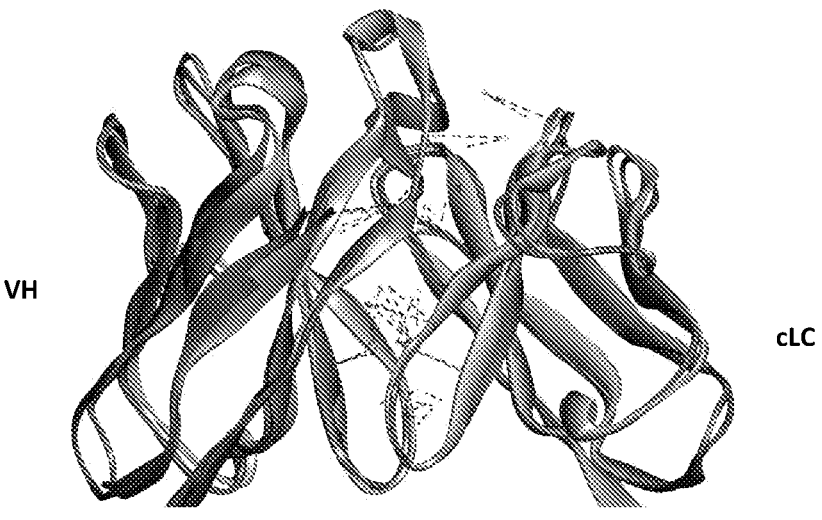

FIG. 10C sets out the electrostatic interactions at the duck heavy chain variable region, human common light chain variable region interface and shows a graphical representation of the interactions set out in FIG. 10a.

Figure 11:

FIG. 11 sets out the genomic DNA sequence comprising the single functional chicken VH gene segment (NCBI accession number M30319). DNA encoding the VH leader is highlighted light grey; DNA encoding mature VH is highlighted dark grey. The mature sequence is the amino acid sequence of the VH gene segment minus the leader sequence. Sequence upstream and downstream of the highlighted regions represent intergenic sequence.

FIG. 12 sets out the genomic DNA sequence comprising the functional chicken JH gene segment (NCBI accession number M30320). DNA encoding the JH is indicated underlined. Note that the DNA of the JH segment is larger than the amino acid translation, as it includes partial codons at start and end.

FIG. 13 sets out annotated sequence of the forward primer chVH-FW used to amplify this VH gene from cDNA. DNA encoding the start of mature VH is highlighted grey.

FIG. 14 sets out the DNA alignment of forward primer chVH-FW (SEQ ID NO: 15), part of the functional chicken VH, and part of vector MV1511. The SfiI site cloning site is indicated. The first codon of mature VH underlined.

FIG. 15 sets out the annotated reverse complement sequence of reverse primer chVH-RV (SEQ ID NO: 16) used to amplify this VH gene from cDNA. DNA encoding the end of the JH (in fact the entire primer sequence) is highlighted light grey. Mutations away from the chicken JH gene segment are underlined.

FIG. 16 sets out a DNA alignment of the reverse complement (rc) of reverse primer chVH-RV, part of the functional chicken JH, and part of vector MV1511. The BstEII site cloning site is indicated.

FIG. 17A: Amino acid sequence (SEQ ID NO: 5) of human common light chain IGKV1-39/jk1.

FIG. 17B: Common light chain variable domain DNA sequence (SEQ ID NO: 6) and amino acid sequence (SEQ ID NO: 7) of human common light chain IGKV1-39/jk1.

FIG. 17C: Light chain constant region DNA sequence (SEQ ID NO: 8) and amino acid sequence (SEQ ID NO: 9) of human common light chain IGKV1-39/jk1.

FIG. 17D: Amino acid sequence (SEQ ID NO: 10) of human common light chain variable domain IGKV1-39/jk5.

FIG. 17E: Amino acid sequence of the V-region (SEQ ID NO: 11) of IGKV1-39.

Figure 18:
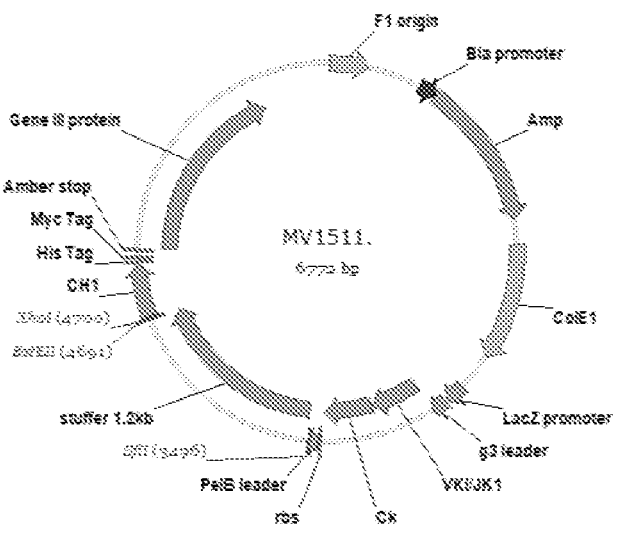

FIG. 18 sets out a schematic diagram of the phage display vector, MV1511.

FIG. 19A: Amino acid sequence (SEQ ID NO: 87) of human common light chain IGKV3-15/jk1.

FIG. 19B: Amino acid sequence (SEQ ID NO: 88) of human common light chain IGKV3-20/jk1.

FIG. 19C: Amino acid sequence (SEQ ID NO: 89) of human common light chain IGLV3-21/jl3.

FIG. 19D: Amino acid sequence (SEQ ID NO: 90) of the V-region of IGKV3-15.

FIG. 19E: Amino acid sequence (SEQ ID NO: 91) of the V-region of IGKV3-20.

FIG. 19F: Amino acid sequence (SEQ ID NO: 92) of the chicken variable heavy chain region of 4GLR and the human CH1 region.

FIG. 19G: Amino acid sequence (SEQ ID NO: 93) of human common light chain IGKV1-39/jk5 and kappa constant region.

FIG. 19H: Amino acid sequence (SEQ ID NO: 94) of human common light chain IGKV3-15/jk1 and kappa constant region.

FIG. 19I: Amino acid sequence (SEQ ID NO: 95) of human common light chain IGKV3-20/jk1 and kappa constant region.

FIG. 19J: Amino acid sequence (SEQ ID NO: 96) of human common light chain IgVλ3-21/IGJλ3 and lambda constant region.

FIG. 19K: Amino acid sequence (SEQ ID NO: 97) of the V-region of IGLV3-21

FIG. 20 provides an analysis of non-covalent, electrostatic interactions in a human Fab comprising a heavy chain comprising MF3178 targeting Her3 (PDB 5O4O; SEQ ID NO: 1) and the human CH1 region, and the human IgV$_K$1-39*01/IGJ$_K$1*01 common light chain (SEQ ID NO: 5) (column indicated with Human VH-Human VL). Thirty-five (35) electrostatic interactions between the human VH-human CH1 and the human IgV$_K$1-39*01/IGJ$_K$1*01 common light chain are observed, of which 24 are present in the VH-VL interface. This is compared to:

1) a homology model of a Fab comprising a heavy chain comprising a chicken VH region having an amino acid sequence as set forth in SEQ ID NO: 2 (from chicken Fab PDB 4GLR) and the human CH1 region, with a cognate chicken VL (from chicken Fab PDB 4GLR) and the human kappa constant region (column indicated with Chicken VH-Chicken VL). Fifty (50) electrostatic interactions between the chicken VH-human CH1 and the chicken VL-human kappa constant region are observed, of which 29 are present in the VH-VL interface;

2) a hybrid homology model of a Fab comprising a heavy chain comprising a VH region having an amino acid sequence as set forth in SEQ ID NO: 2 (from chicken Fab PDB 4GLR), and the human CH1, with a light chain comprising the amino acid sequence of common light chain Vk3-15/JK1 (SEQ ID NO: 94) (column indicated with Vk3-15/JK1/Ckappa). Thirty-one (31) electrostatic interactions between the chicken VH-human CH1 and the human common light chain Vk3-15/JK1 are observed, of which 19 are present in the VH-VL interface;

3) a hybrid homology model of a Fab comprising a heavy chain comprising a VH region having an amino acid sequence as set forth in SEQ ID NO: 2 (from chicken Fab PDB 4GLR), and the human CH1, with a light chain comprising the amino acid sequence of common light chain Vk3-20/JK1 (SEQ ID NO: 95) (column indicated with VK3-20/JK1/Ckappa). Forty-seven (47) electrostatic interactions between the chicken VH-human CH1 and the human common light chain Vk3-20/JK1 are observed, of which 25 are present in the VH-VL interface;

4) a hybrid homology model of a Fab comprising a heavy chain comprising a VH region having an amino acid sequence as set forth in SEQ ID NO: 2 (from chicken Fab PDB 4GLR), and the human CH1, with a light chain comprising the amino acid sequence of common light chain Vk1-39/JK5 (SEQ ID NO: 93) (column indicated with VK1-39/JK5/Ckappa). Forty-five (45) electrostatic interactions between the chicken VH-human CH1 and the human common light chain Vk1-39/JK5 are observed, of which 21 are present in the VH-VL interface;

5) a hybrid homology model of a Fab comprising a heavy chain comprising a VH region having an amino acid sequence as set forth in SEQ ID NO: 2 (from chicken Fab PDB 4GLR), and the human CH1, with a light chain comprising the amino acid sequence of common light chain VI3-21/J13 (SEQ ID NO: 96) (column indicated with VL3-21/JL3/Clambda). Forty-four (44) electrostatic interactions between the chicken VH-human CH1 and the human common light chain VI3-21/J13 are observed, of which 23 are present in the VH-VL interface.

Chain A is the light chain. Chain B is the heavy chain. Kabat numbering used. The interactions between de VH and VL are indicated in italic.

Figure 21:
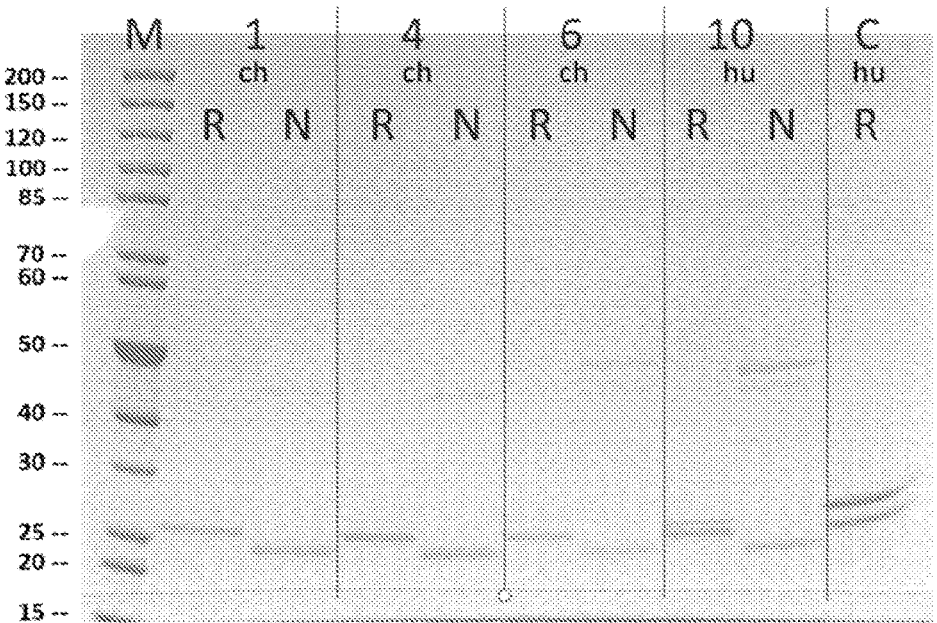

FIG. 21 shows SDS-PAGE blots under reduced (R) and non-reduced (N) conditions. Chimeric Fabs are indicated with 1, 4, and 6; human Fab is indicated with 10. C is a human Fab serving as a positive control for the presence of Fab.

FIG. 22 provides the amino acid sequence (SEQ ID NO: 98) of the VH in the human control Fab.

FIG. 23A shows a Western blot under reduced (R) and non-reduced (N) conditions. Chimeric Fab is loaded in lanes 3 and 4 (purified), and lanes 7 and 8 (non-purified). Human Fab is loaded in lanes 1 and 2 (purified) and lanes 5 and 6 (non-purified). Fabs are identified using ProtL-HRP. FIG. 23B shows a Western blot under reduced (R) and non-reduced (N) conditions. Chimeric Fab is loaded in lanes 3 and 4 (purified), and lanes 7 and 8 (non-purified). Human Fab is loaded in lanes 1 and 2 (purified) and lanes 5 and 6 (non-purified). Fabs are identified using α-myc-HRP.

FIG. 24 provides the wildtype amino acid full length sequence of mouse CXCR4.

FIGS. 25A and 25B show the mouse CXCR4 positive control and the human CXCR4 positive control, respectively. FIGS. 25C-E show the flow cytometry results for the binding of three different chicken VH-human VL Fabs to mouse and human CXCR4.

FIG. 26A provides the amino acid sequence (SEQ ID NO: 100) of the heavy chain variable region of a first chimeric Fab comprising a chicken VH paired with a human VL that binds to mouse and human CXCR4.

FIG. 26B provides the amino acid sequence (SEQ ID NO: 101) of the heavy chain variable region of a second chimeric Fab comprising a chicken VH paired with a human VL that binds to mouse and human CXCR4.

FIG. 26C provides the amino acid sequence (SEQ ID NO: 102) of the heavy chain variable region of a third chimeric Fab comprising a chicken VH paired with a human VL that binds to mouse and human CXCR4.

Figure 27A:
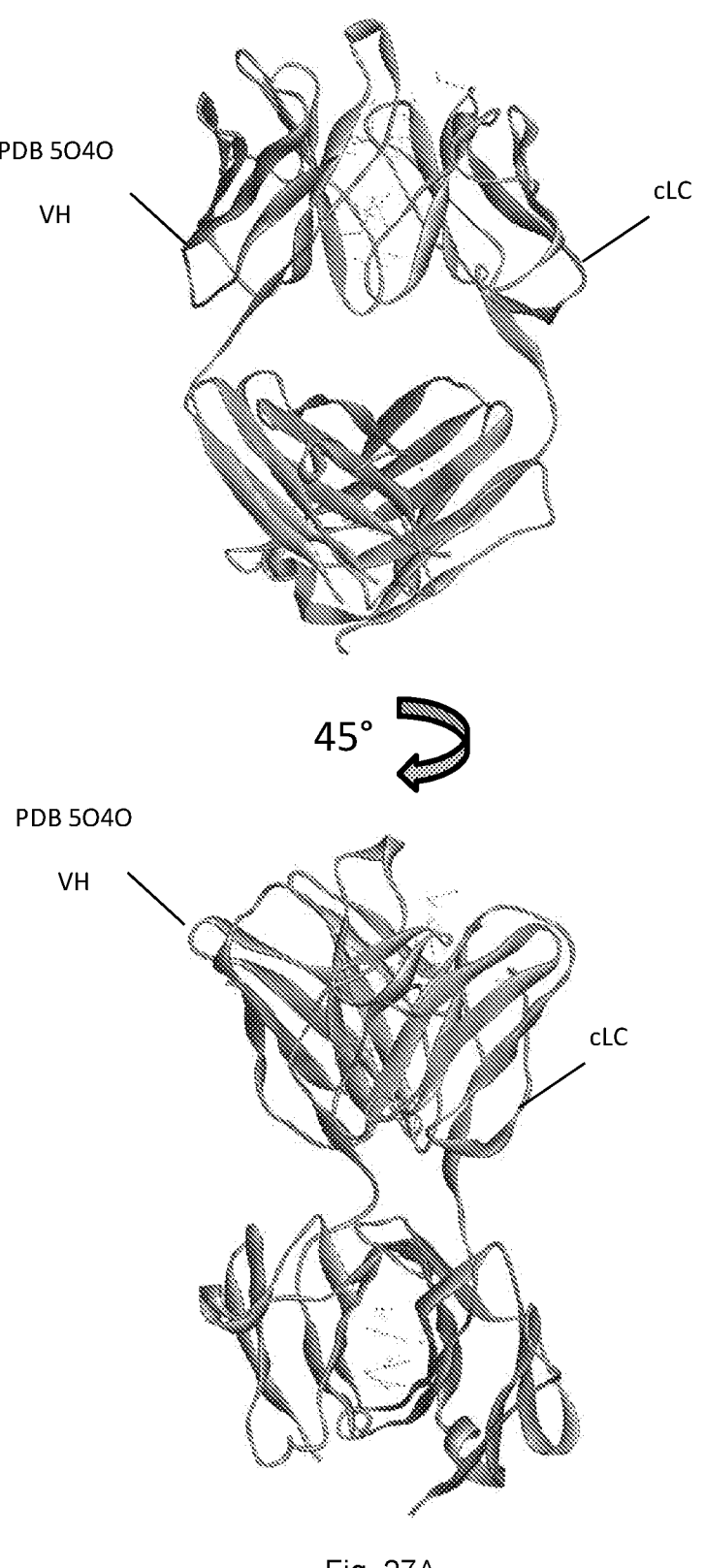

FIG. 27A sets out the binding domain comprised of the human heavy chain variable region of PDB 5O4O, and human CH1 paired with the common light chain, including the variable region of the IgV$_K$1-39/IGJ$_K$1 common light chain (SEQ ID NO: 5—the full length common light chain sequence including the CL region).

Figure 27B:
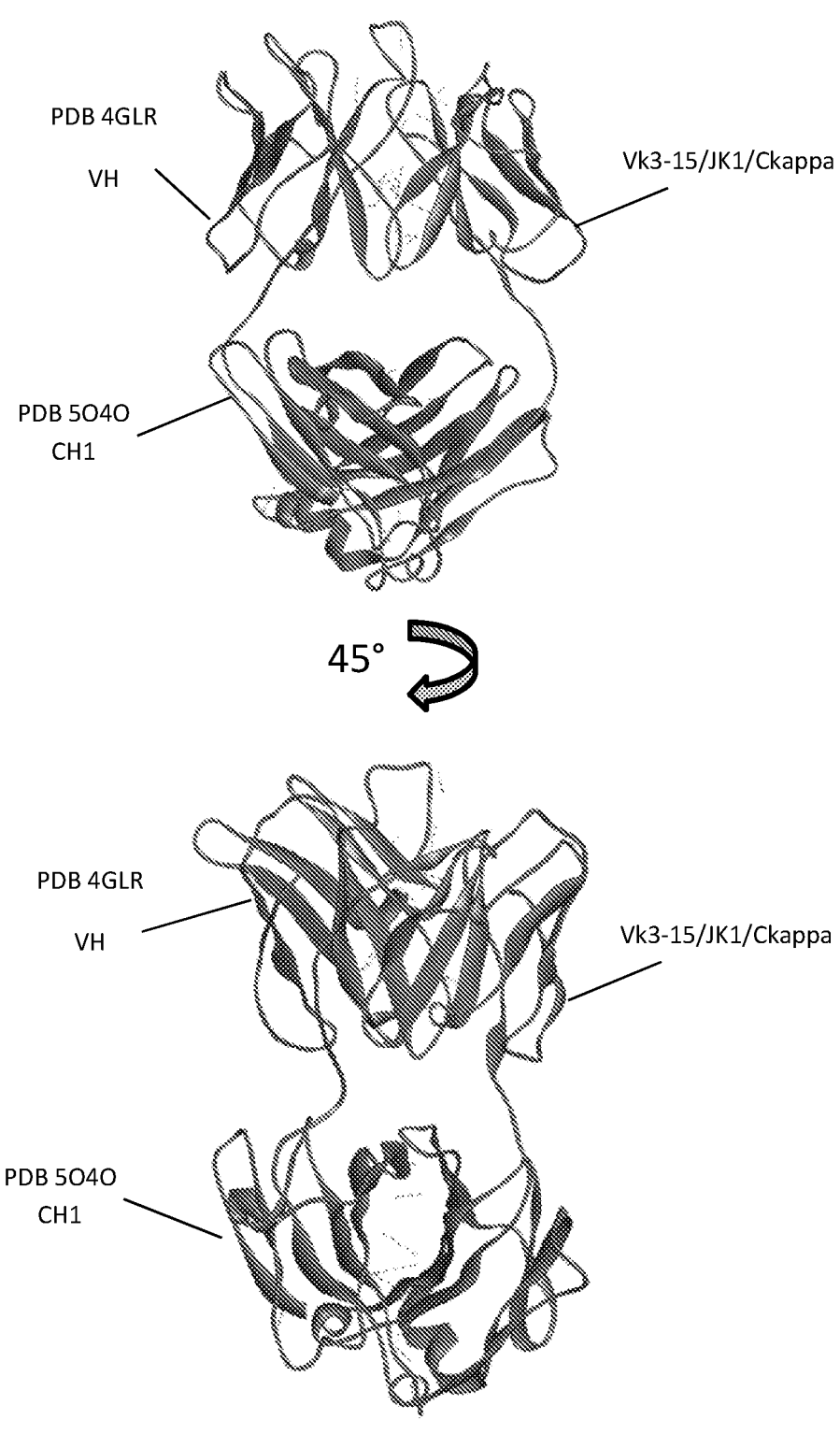

FIG. 27B sets out the binding domain comprised of the chicken heavy chain variable region of PDB 4GLR, and human CH1 paired with the common light chain, including the variable region of the IgV$_K$3-15/IGJ$_K$1 common light chain (SEQ ID NO: 26—the full length common light chain sequence including the CL region).

Figure 27C:
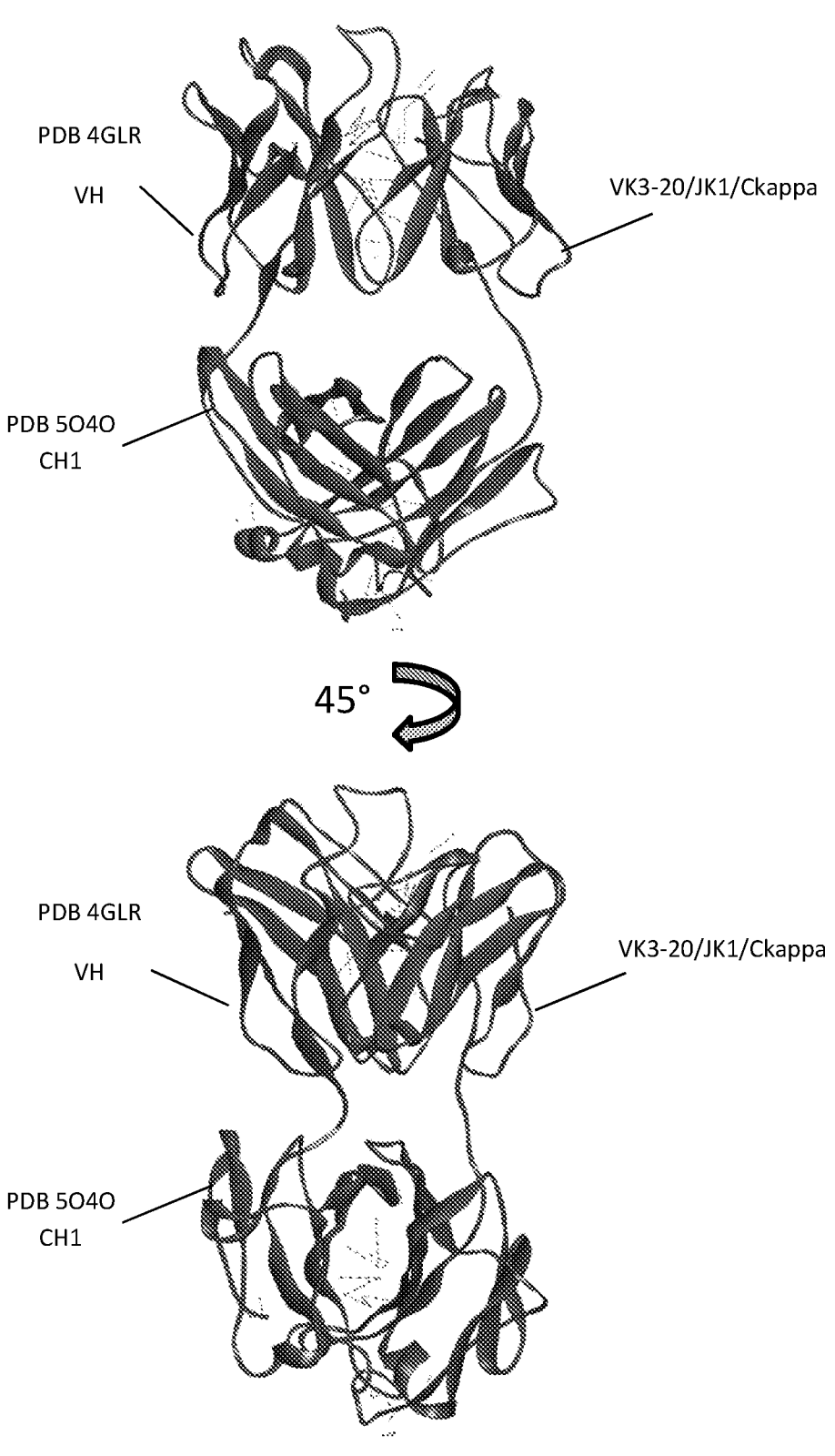

FIG. 27C sets out the binding domain comprised of the chicken heavy chain variable region of PDB 4GLR, and human CH1 paired with the common light chain, including the variable region of the IgV$_K$3-20/IGJ$_K$1 common light chain (SEQ ID NO: 95—the full length common light chain sequence including the CL region).

Figure 27D:
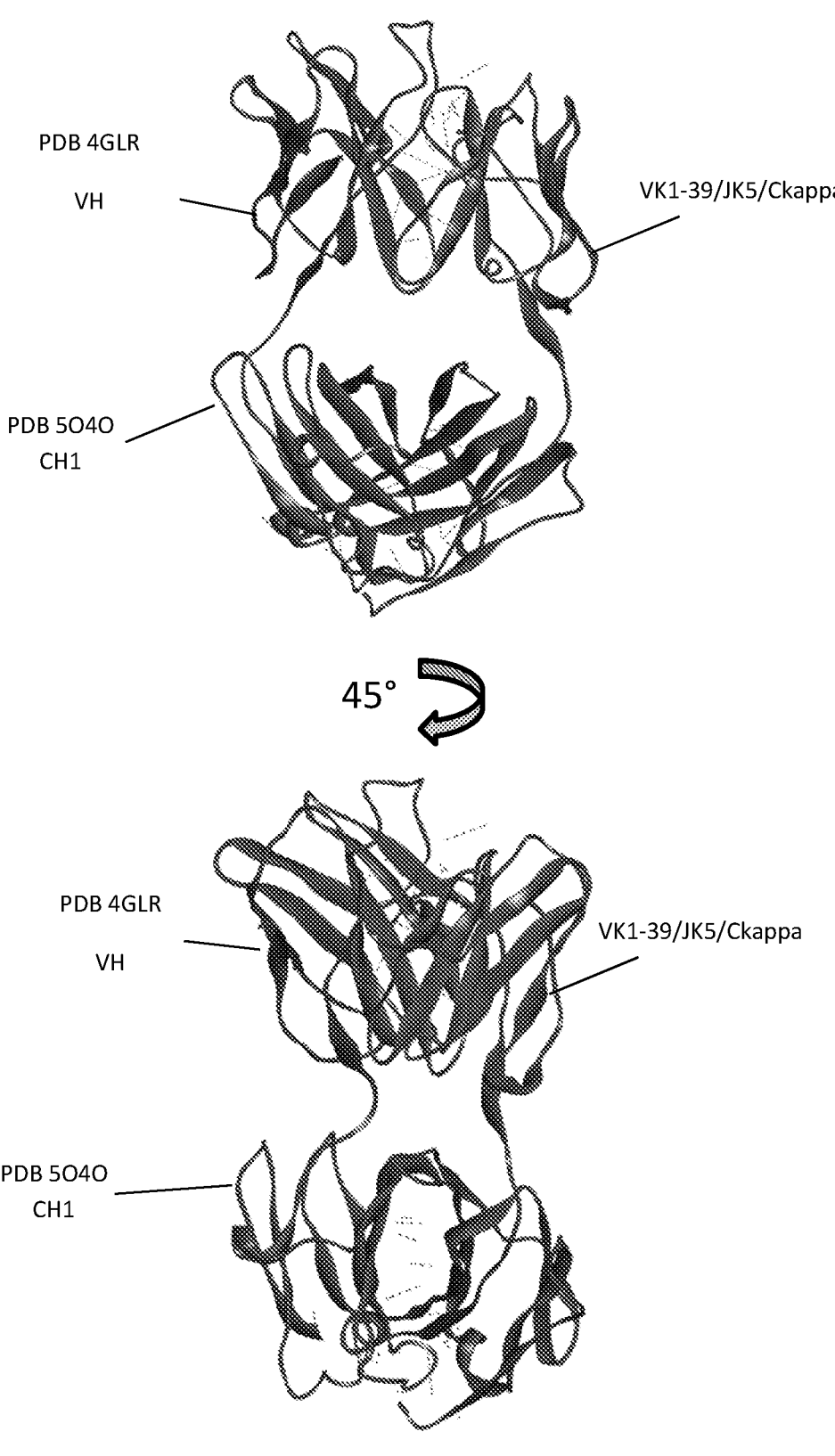

FIG. 27D sets out the binding domain comprised of the chicken heavy chain variable region of PDB 4GLR, and human CH1 paired with the common light chain, including the variable region of the IgV$_K$1-39/IGJ$_K$5 common light chain (SEQ ID NO: 93—the full length common light chain sequence including the CL region).

Figure 27E:
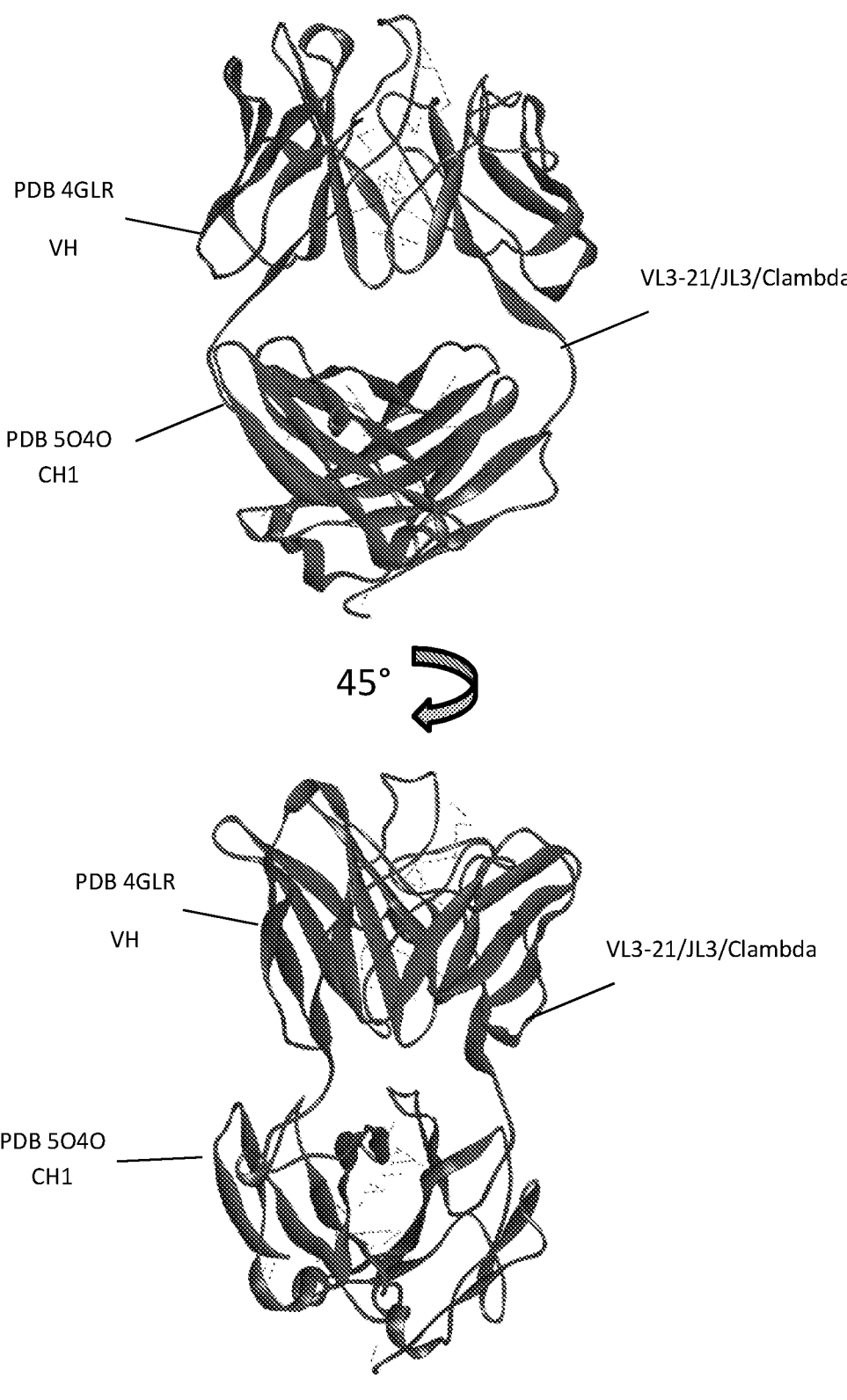

FIG. 27E sets out the binding domain comprised of the chicken heavy chain variable region of PDB 4GLR, and human CH1 paired with the common light chain, including the variable region of the IgVL3-21/IGJI3 common light chain (SEQ ID NO: 96—the full length common light chain sequence including the CL region).

DETAILED DESCRIPTION

An "antibody" is a proteinaceous molecule belonging to the immunoglobulin class of proteins, containing one or more domains that bind an epitope on an antigen, where such domains are derived from or share sequence homology with the variable region of an antibody.
Antibody binding has different qualities including specificity and affinity. The specificity determines which antigen or epitope thereof is specifically bound by the binding domain. The affinity is a measure for the strength of binding to a particular antigen or epitope. It is convenient to note here that the 'specificity' of an antibody refers to its selectivity for a particular antigen, whereas 'affinity' refers to the strength of the interaction between the antibody's antigen binding site and the epitope it binds.

Thus, the "binding specificity" as used herein refers to the ability of an individual antibody binding site to react with an antigenic determinant. Typically, the binding site of the antibody of the invention is located in the Fab portions and is constructed from the hypervariable regions of the heavy and light chains.

"Affinity" is the strength of the interaction between a single antigen-binding site and its antigen. A single antigen-binding site of an antibody of the invention for an antigen may be expressed in terms of the disassociation constant ($K_d$). Typically, antibodies for therapeutic applications may have affinities with a $K_d$ of down to $1 \times 10^{-10}$ M or even higher affinity (i.e. an even lower $K_d$).

An "antigen" is a molecule capable of inducing an immune response (to produce an antibody) in a host organism and/or being targeted by an antibody. At the molecular level, an antigen is characterized by its ability to be bound by the antigen-binding site of an antibody. Also mixtures of antigens can be regarded as an 'antigen', i.e. the skilled person would appreciate that sometimes a lysate of tumor cells, or viral particles may be indicated as 'antigen' whereas such tumor cell lysate or viral particle preparation exists of many antigenic determinants. An antigen comprises at least one, but often more, epitopes.

An "epitope" or "antigenic determinant" is a site on an antigen to which an immunoglobulin or antibody specifically binds. Epitopes can be formed from contiguous amino acids or noncontiguous amino acids juxtaposed by tertiary folding of a protein (so-called linear and conformational epitopes, respectively). Epitopes formed from contiguous, linear amino acids are typically retained on exposure to denaturing solvents, whereas epitopes formed by tertiary folding, conformation are typically lost on treatment with denaturing solvents. An epitope may typically include 3, 4, 5, 6, 7, 8, 9, 10, 11, 12, 13, 14 or 15 amino acids in a unique spatial conformation.

The term "heavy chain" or "immunoglobulin heavy chain" includes an immunoglobulin heavy chain constant region sequence from any organism, and unless otherwise specified includes a heavy chain variable domain (VH). The term heavy chain variable domains include three heavy chain CDRs and four frame work (FR) regions, unless otherwise specified. Fragments of heavy chains include CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen and that comprises at least one CDR.

The term "light chain" includes an immunoglobulin light chain variable domain, or $V_L$ (or functional fragment thereof); and an immunoglobulin constant domain, or $C_L$ (or functional fragment thereof) sequence from any organism. Unless otherwise specified, the term light chain may include a light chain selected from a human kappa, lambda, and a combination thereof. Light chain variable ($V_L$) domains typically include three light chain CDRs and four FR regions, unless otherwise specified. Generally, a full-length light chain includes, from N-terminus to C-terminus, a $V_L$ domain that includes FR1-CDR1-FR2-CDR2-FR3-CDR3-FR4 and a light chain constant domain. Light chains that can be used with this invention include those, e.g., that do not selectively bind an epitope selectively bound by the heavy chains.

Suitable light chains for use in an antibody of the invention include a common light chain (cLC), such as those that can be identified by screening for the most commonly employed light chains in existing antibody libraries (wet libraries or in silico), where the light chains do not substantially interfere with the affinity and/or selectivity of the epitope-binding domains of the heavy chains, but are also suitable to pair with an array of heavy chains. For example, a suitable light chain includes one from a transgenic animal, such as MeMo® having the common light chain integrated into its genome and which can be used to generate large panels of common light chain antibodies having diversity at the heavy chain and capable of specifically binding an antigen upon exposure to said antigen.

The term "common light chain" according to the invention refers to light chains which may be identical or have some amino acid sequence differences while the binding specificity of an antibody of the invention is not affected, i.e. the differences do not materially influence the formation of functional binding regions.

It is for instance possible within the scope of the definition of common chains as used herein, to prepare or find variable chains that are not identical but still functionally equivalent, e.g., by introducing and testing conservative amino acid changes, changes of amino acids in regions that do not or only partly contribute to binding specificity when paired with a cognate chain, and the like. Such variants are thus also capable of binding different cognate chains and forming functional antigen binding domains. The term 'common light chain' as used herein thus refers to light chains which may be identical or have some amino acid sequence differences while retaining the binding specificity of the resulting antibody after pairing with a heavy chain. A combination of a certain common light chain and such functionally equivalent variants is encompassed within the term "common light chain". Reference is made to WO 2004/009618 and WO2009/157771 for a detailed description of the use of common light chains.

A "Fab" means a binding domain comprising a variable region, typically a binding domain comprising a paired heavy chain variable region and light chain variable region. A Fab may comprise constant region domains, including a CH1 and a VH domain paired with a constant light domain (CL) and VL domain. Such pairing may take place, for example, as covalent linkage via a disulfide bridge at the CH1 and CL domains.

A "single-chain variable fragment" (scFv) means a binding domain comprising a VH domain and a VL domain which are connected via a linker, for example a peptide linker, for example from about 10 to about 25 amino acids in length.

Herein, the term "connected" refers to domains which are joined to each other by way of their primary amino acid sequence. For example, a base antibody portion may be connected to an additional binding domain (or an additional binding domain to an additional binding domain) via a linker. Similarly, a CH1 domain may be connected to a variable heavy region and a CL domain may be connected to a variable light region.

"Pairing" then refers to interactions between the polypeptides the invention such that they may multimerize. Domains of antibody chains or polypeptides, such as a mixed binding domain may interact and pair to form an interface, via covalent or non-covalent interactions, for example, via Van der Waals forces, hydrogen bonds, water-mediated hydrogen bonds, salt bridges or other electrostatic forces, attractive interactions between aromatic side chains, the formation of disulfide bonds, or other forces known to one skilled in the art.

"Percent (%) identity" as referring to nucleic acid or amino acid sequences herein is defined as the percentage of residues in a candidate sequence that are identical with the residues in a selected sequence, after aligning the sequences for optimal comparison purposes. The percent sequence identity comparing nucleic acid sequences is determined using the AlignX application of the Vector NTI Program Advance 10.5.2 software using the default settings, which employ a modified ClustalW algorithm (Thompson, J. D., Higgins, D. G., and Gibson T. J. (1994) Nuc. Acid Res. 22: 4673-4680), the swgapdnarnt score matrix, a gap opening penalty of 15 and a gap extension penalty of 6.66. Amino acid sequences are aligned with the AlignX application of the Vector NTI Program Advance 11.5.2 software using default settings, which employ a modified ClustalW algorithm (Thompson, J. D., Higgins, D. G., and Gibson T. J., 1994), the blosum62mt2 score matrix, a gap opening penalty of 10 and a gap extension penalty of 0.1.

"Plurality" means two or more.

A "variant" of an antibody as described herein may comprise a functional part, derivative and/or analogue of an antibody. This includes antibody mimetics, monobodies and aptamers.

A variant typically maintains the binding specificity of the antibody, for example the specificities of a bispecific antibody. A variant may be a functional part or derivative of a binding domain, multimer or antibody as described herein.

A functional part of a binding domain, multimer or antibody as described herein is a part comprising a variable domain that binds the same target as such binding domain, multimer or antibody.

A functional derivative of an antibody as described herein is a protein comprising a variable domain that binds one target and a variable domain that binds a second target that are linked by a linking region. The variable domains may be variable domains as such, or Fab fragments or variable domain like molecules such as single chain Fv (scFv) fragments comprising a VH and a VL linked together via a linker. Other examples of variable domain like molecules are so-called single domain antibody fragments. A single-domain antibody fragment (sdAb) is an antibody fragment with a single monomeric variable antibody region. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. Other non-limiting examples of variable domain-like molecules are VHH, Human Domain Antibodies (dAbs) and Unibodies. Preferred functional parts are parts that comprise variable domains comprising a heavy chain variable region and a light chain variable region. Non-limiting examples of such variable domains are F(ab)-fragments and Single chain Fv fragments. Bispecific formats for variable domain(-like) linkage are for instance Human Serum Albumin (HSA) bound to two different scFv; bispecific mini-antibodies comprising two different scFv bound together via dimerization motifs or self-associating secondary structures such as helix bundles or coiled coils to bring about dimerization of the scFv fragments (Morrison (2007) Nat. Biotechnol. 25:1233-34). Examples of suitable HSA linkers and method for coupling scFv to the linker are described in WO2009/126920.

A functional derivative can be an antibody mimetic, a polypeptide, an aptamer or a combination thereof. These proteins or aptamers typically bind to one target. The protein of the invention binds to two or more targets. It is to be understood that any combination of these antibodies, antibody mimetics, polypeptides and aptamers can be linked together by methods known in the art. For example, in some embodiments the binding molecule of the invention is a conjugate or a fusion protein.

An antibody mimetic is a polypeptide that, like antibodies, can specifically bind an antigen, but that is not structurally related to antibodies. Antibody mimetics are usually artificial peptides or proteins with a molar mass of about 3 to 20 kDa. Common advantages over antibodies are better solubility, tissue penetration, stability towards heat and enzymes, and comparatively low production costs. Non-limiting examples of antibody mimetics are affibody molecules (typically based on the Z domain of Protein A); affilins (typically based on Gamma-B crystalline or Ubiquitin); affimers (typically based on Cystatin); affitins (typically based on Sac7d from *Sulfolobus acidocaldarius*); alphabodies (typically based on Triple helix coiled coil); anticalins (typically based on Lipocalins); avimers (typically based on A domains of various membrane receptors); DARPins (typically based on ankyrin repeat motif); fynomers (typically based on SH3 domain of Fyn 7); kunitz domain peptides (typically based on Kunitz domains of various protease inhibitors); and monobodies (typically based on type Ill domain of fibronectin).

Monobodies are synthetic binding proteins that are constructed using a fibronectin type Ill domain (FN3) as a molecular scaffold. Monobodies are simple and robust alternative to antibodies for creating target-binding proteins. The term "monobody" was coined in 1998 by the Koide group who published the first paper demonstrating the monobody concept using the tenth FN3 domain of human fibronectin.

Monobodies and other antibody mimetics are typically generated from combinatorial libraries in which portions of the scaffold are diversified using molecular display and directed evolution technologies such as phage display, mRNA display and yeast surface display. A large number of antibody mimetics have high affinity and high specificity to their respective targets.

Aptamers are oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecules.

"Non-bonded" interactions" act between atoms which are not linked by covalent bonds. Accordingly these are bonds that do not involve the sharing of electrons, but rather involve the more dispersed variations of electromagnetic interactions between molecules or within a molecule. Non-bonded interactions include electrostatic interactions, such as hydrogen bonding, ionic interactions and Halogen bonding. Van der Waals forces are a subset of electrostatic interactions involving permanent or induced dipoles (or multipoles). These include the following: permanent dipole-dipole interactions, dipole-induced dipole interactions and induced dipole-induced dipole interactions. Salt bridges are a combination of two non-covalent interactions: hydrogen bonding and ionic bonding. Hydrophobic interactions are interaction of non-polar (un-ionizable) hydrocarbon molecules forced together because of stronger water-water interaction.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element. Variable Regions, Binding Domains, Multimers and Antibodies The invention relates to a binding domain and to multimers, such as antibodies, which comprise the binding domain or to a variant of any thereof. Typically, a binding domain of the invention comprises a variable region encoded by a nucleic acid based on, derived or obtained at least in part from a nucleic acid of an organism phylogenetically distal to a human, for example a bird, preferably chicken, duck or ostrich. That variable region is typically paired with a human variable region. Accordingly, a binding domain of an invention disclosed herein, may be a chimeric, or humanized or mixed binding domain.

Typically, the variable region is encoded by a nucleic acid based on, derived from or obtained from a nucleic acid of a bird, preferably a chicken, duck or ostrich, wherein the encoded variable region is a heavy chain variable region, which is capable of pairing stably with a human variable region, which is a light chain variable region. Alternatively, the variable region encoded by a nucleic acid based on, derived from or obtained from a nucleic acid of a bird, preferably a chicken may be a light chain variable region, which is capable of pairing with a human variable region that may be a heavy chain variable region.

"Based on", in reference to a nucleic acid means that the nucleic acid sequence encodes the same amino acid as a nucleic acid it is based on, irrespective of the particular codons matching the based on nucleic acid sequence or source, accounting for redundancy in genetic code, which provides for alternative codons that encode the same residue. "Derived from" means a nucleic acid may be cloned from a nucleic acid of an organism of interest, or produced synthetically that match sequence information of that source.

The binding domain may comprise a variable region, Fv domain, a Fab domain, a modified Fab domain or a scFv or a functional fragment of any thereof.
Birds A binding domain of an invention described herein, comprises an immunoglobulin variable region, or a portion thereof, encoded by a nucleic acid based on, derived or obtained from a nucleic acid of a bird comprising the order Galliformes, for example a chicken, turkey, grouse, New World quail, Old World quail, ptarmigan, partridge, pheasant, junglefowl, a bird of the family Cracidae a goose swan, duck or ostrich.

Figure 4B:
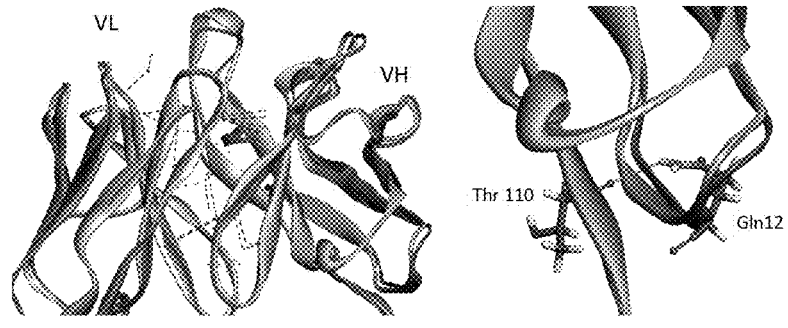
FIG. 4 provides a structure analysis of a model of the interface between a chicken VH region and human common light chain region.

A binding domain of an invention described herein, comprises a variable region encoded by a nucleic acid based on, derived or obtained from a nucleic acid of an animal phylogenetically distal to a human, preferably a heavy chain variable region, wherein such variable region comprises substantially the same number of non-bonded electrostatic interactions as present between a human VH and VL interface, such as that of a human Fab comprising a heavy chain variable region having SEQ ID NO: 1 and a light chain variable region having SEQ ID NO: 7 (see FIG. 4*a*), and preferably more such interactions.

A binding domain of an invention described herein, preferably is a mixed binding domain comprising a variable region, preferably a heavy chain variable region, encoded by a nucleic acid based on, derived or obtained from a nucleic acid of an animal, phylogenetically distal to a human, paired to a human chain, preferably a human VL, wherein the VH/VL interface have at least 5, and preferably 10 or more interactions at the VH/VL interface that are homologous, and preferably identical compared with the human VH and common VL found at the same positions of a human Fab comprising a heavy chain variable region having SEQ ID NO: 1 and a light chain variable region having SEQ ID NO: 7.

A binding domain of an invention described herein comprises a variable region encoded by a nucleic acid based on, derived or obtained from a nucleic acid of an animal phylogenetically distal to a human and encoding a human variable region.

A binding domain of an invention described herein can comprise a VH region encoded by a nucleic acid based on, derived or obtained from a nucleic acid of a bird, which forms an interface with a human light chain region, wherein the VH/VL interface of said binding domain comprises at least 4, preferably 5, preferably 8, and more preferably 10 electrostatic contact points between the VH region and human VL region that is identical or equivalent to the electrostatic contact points of a human VH region/human VL region binding domain interface, preferably wherein said human VL is that of the $IgV_K1-39*01/IGJ_K1*01$ common light chain (SEQ ID NO: 7); of the $IgV_K1-39/IGJ_K5$ common light chain (SEQ ID NO: 10); of the $IgV_K3-15/IGJ_K1$ common light chain (SEQ ID NO: 87); of the $IgV_K3-20/IGJ_K1$ common light chain (SEQ ID NO: 88); or of the $IgV_\lambda3-21/IGJ_\lambda3$ common light chain (SEQ ID NO: 89), most preferably wherein the human VL is that of the $IgV_K1-39*01/IGJ_K1*01$ common light chain (SEQ ID NO: 7), and preferably where the comparator human binding domain is a human Fab comprising a heavy chain variable region having SEQ ID NO: 1 and a light chain variable region having SEQ ID NO: 7.

Alternatively, a binding domain of an invention described herein comprises a VH region encoded by a nucleic acid based on, derived or obtained from a nucleic acid of a bird, which forms an interface with a human light chain region, wherein the VH/VL interface of said binding domain comprises at least fourteen (14) and more preferably twenty-four (24) electrostatic contact points, and more preferably twenty-eight (28) electrostatic contact points between the VH region and human VL region, preferably wherein said human VL is that of the $IgV_K1-39*01/IGJ_K1*01$ common light chain (SEQ ID NO: 7); of the $IgV_K1-39/IGJ_K5$ common light chain (SEQ ID NO: 10); of the $IgV_K3-15/IGJ_K1$ common light chain (SEQ ID NO: 87); of the $IgV_K3-20/IGJ_K1$ common light chain (SEQ ID NO: 88); or of the $IgV_\lambda3-21/IGJ_\lambda3$ common light chain (SEQ ID NO: 89), most preferably wherein the human VL is that of the $IgV_K1-39*01/IGJ_K1*01$ common light chain (SEQ ID NO: 7).

According to an invention disclosed herein, there is a binding domain or multimer, such as an antibody, or a variant thereof which comprises a variable region encoded by a nucleic acid based on, derived from or obtained from, at least in part, a nucleic acid of an animal phylogenetically distal from a human, wherein such variable region when paired with a human variable region, includes substantially the same electrostatic contact points at the variable region interface as exists for a human VH and human VL interface, preferably as in a human Fab comprising a heavy chain variable region having SEQ ID NO: 1 and a light chain variable region having SEQ ID NO: 7, comprising 4, preferably 5, preferably 8 and more preferably 10 electrostatic interactions with a human VL variable region at the VH, VL interface, preferably a $IgV_K1-39*01/IGJ_K1*01$ light chain, a $IgV_K1-39/IGJ_K5$ light chain, a $IgV_K3-15/IGJ_K1$ light chain, a $IgV_K3-20/IGJ_K1$ light chain, or a $IgV_\lambda3-21/IGJ_\lambda3$ common light chain, most preferably a $IgV_K1-39*01/IGJ_K1*01$ or $IgV_K1-39*01/IGJ_K1*05$ light chain, wherein such an animal is a chicken, an ostrich or a duck.

Constant regions of a binding domain, multimer or antibody of the invention are typically human constant regions (e.g., CH1, CH2, CH3 and CL), but may comprise rodent or other chimeric constant regions or constant regions from the same organism or source as the variable region encoded by a nucleic acid based on, derived from or obtained from, at least in part, a nucleic acid of an animal phylogenetically distal from a human.

A binding domain or, multimer, such as an antibody, or a variant of the invention may be one in which the variable region is encoded by a nucleic acid based on, derived or obtained from at least in part a bird nucleic acid, which has undergone V(D)J recombination including through B-cell development and/or in response to antigenic exposure of such animal. Said binding domain may be one in which said variable region is a heavy chain variable region paired with a human light chain variable region, preferably a common light chain, more preferably comprising the $IgV_K1-39*01/IGJ_K1*01$ light chain (SEQ ID NO: 5), $IgV_K1-39/IGJ_K5$ light chain (SEQ ID NO: 93), $IgV_K3-15/IGJ_K1$ light chain (SEQ ID NO: 94), $IgV_K3-20/IGJ_K1$ light chain (SEQ ID NO: 95), or the $IgV_\lambda3-21/IGJ_\lambda3$ common light chain (SEQ ID NO: 96), most preferably the $IgV_K1-39*01/IGJ_K1*01$ common light chain (SEQ ID NO: 5).

A binding domain or multimer, such as an antibody, or variant thereof of the invention may be one in which the variable region is encoded by a nucleic acid based on, derived or obtained from at least in part a bird nucleic acid, which has undergone V(D)J recombination including in response to antigenic exposure of such animal. Said binding domain may be one in which the said variable region is a light chain variable region paired with a human heavy chain variable region, preferably a common heavy chain.

A binding domain or multimer, such as an antibody, or variant thereof of the invention may be one in which the variable region is humanized, such that the CDRs are encoded by a nucleic acid based on, derived or obtained from at least in part a nucleic acid of a bird, which has undergone V(D)J recombination including through B-cell development and/or in response to antigenic exposure of such animal.

A multimer according to the invention comprises at least one binding domain as described herein. A multimer according to the invention can be a monovalent, bivalent or multivalent multimer or antibody.

A bivalent or multivalent antibody or multimer of an invention disclosed herein is capable of binding one, two or preferably more than two targets, wherein a target may be an antigen or an epitope of a given antigen.

Immunization of an Animal

A binding domain or multimer, such as an antibody, or variant thereof of the invention comprises a variable region encoded by a nucleic acid which is based on, derived or obtained at least in part from a nucleic acid of an animal phylogenetically distal to a human, for example a bird, which has been immunized with an antigen or epitope of interest. As such, the variable region has specificity against said antigen or epitope.

Methods of immunizing a diverse array of animals, including birds, for example chickens, ducks or ostriches are well known to persons of ordinary skill in the art. A suitable immunization protocol is typically one that causes the selective expansion of B cells, meaning that primary and booster immunizations are designed to cause selective expansions of B cells that produce antibodies that bind to the antigen or epitope of interest. The immunization protocol may for example use different forms or fragments of the antigen during primary immunization and each subsequent booster immunization. For example, the antigen may be expressed on the membrane of a cell, a recombinant protein, a recombinant protein fused to another protein, a domain of a protein or a peptide of a protein. The immunization protocol may include the use of an adjuvant during the primary and/or booster immunizations.

An adjuvant may be used during primary immunization only to limit the extent of non-specific expansion of bystander B cells. Bystander B cells are cells that are activated without the step of binding of antigen to the antibody receptor expressed on the surface of the B cell. It is known in the art that immunization with Fc-fusion proteins for example, often results in a robust anti-Fc response where up to about 70% of all B cells react to the Fc part of the fusion protein rather than to the antigen of interest. An immunization protocol may be used without adjuvant to preferentially expand B cells that have been activated by the antigen used for immunization.

A nucleic acid encoding a variable region suitable for use in a binding domain of the invention may be recovered from any suitable tissue, for example from eggs, from lymph tissue or from bone marrow (i.e. from tissue producing B cells).

Accordingly, a method for producing a binding domain or multimer or a variant thereof of the invention may comprise at least a step of isolating nucleic acids encoding variable regions of antibodies from a population of, for example, B cells, or from eggs or serum which are obtained from a bird, wherein said bird has been immunized with an antigen, such that selective clonal expansion of B cells that react with the antigen or epitope of interest is preferentially induced. A suitable animal, such as a bird, may be immunized with an antigen in the form of a protein or in the form of a nucleic acid sequence which is capable of expressing the antigen when the bird is immunized with said nucleic acid sequence.

Birds may be immunized by means of, for example, intramuscular vaccination or by means of Gene-Gun plasmid-immunization, or by any other means known in the art. A preferred way of inducing selective clonal expansion of B cells is DNA tattoo vaccination. The term 'DNA tattoo vaccination' refers to an invasive procedure involving a solid vibrating needle loaded with plasmid DNA that repeatedly punctures the skin, wounding both the epidermis and the upper dermis and causing cutaneous inflammation followed by healing (Bins et al., Nat Med 11:899-904, 2005; Pokorna et al., Genet. Vaccines Ther. 6: 4, 2008). Said DNA may be codon optimized for expression in birds, and may include sequences designed to prevent gene silencing.

Immunization protocols for chickens are known in the art. For example, see Schade et al., ATLA Altern. Lab. Anim. 24 (1996) 925-934. See also http://gallusimmunotech.com/igy-polyclonal-antibodies-immunization-protocol and https://www.thermofisher.com/nl/en/home/life-science/antibodies/custom-antibodies/custom-antibody-production/custom-polyclonal-antibody-production/custom-chicken-polyclonal-antibody-production-protocols.html.Commercially available companies performing chicken immunizations include for instance Aves Labs Inc., Davids Bio, Creative Biolabs, Lampire Biological Laboratories, Integral Molecular, Aldevron, Innovagen and Capralogics.

Ducks and ostriches may also be similarly immunized. Briefly, ducks and ostriches may receive subcutaneous or intramuscular injections of a mixture containing the antigen and Freund's complete adjuvant. Booster shots may then be administered using a mixture of the antigen and Freund's incomplete adjuvant.

One week after the first duck immunization, duck eggs may start to be collected and stored at 4° C. Booster shots may be repeated every four weeks and blood serum may be analysed 7 days after each booster injection. The subsequent procedures involve a short protocol of water extraction of IgY from the yolk, followed by delipidation, salting out, desalting and concentration. Protein concentration of the antibody solution may be determined by absorbance at 280 nm.

One week after the first ostrich immunization, serum antibody levels may be measured from blood samples obtained from the jugular vein. Boosters may be administered every other week. At four weeks, yolk antibody levels may be measured by precipitation reaction in agarose gel. Immunizations and antibody isolations of ducks are described in, for example, U.S. Pat. No. 6,680,376 B2 and AU784900 and Chiou et al., Clinical Toxicology. 2008, 46: 539-544 and immunizations and antibody isolations of ostriches are described in, for example, Adachi et al., Exp Ther Med. 2011, 2:41-45 and in WO2007026689.

A representative immunization protocol may include a step of collection of at least one egg prior or serum to immunization. IgY recovered from these eggs may be used as a control. On day 0, inject, for example, from 0.02 to 0.5 mg antigen, (for example with Freund's complete adjuvant Specol, lipopeptide (Pam$_3$-Cys-Ser-[Lys]$_4$, for example in an amount of 250 pg) subcutaneously and/or intramuscularly into the breast tissue of a chicken at multiple sites. The total volume of antigen/adjuvant may be about 1 ml with the adjuvant making up between half and two-thirds the volume. A comparable amount of antigen is used as would be used to immunize a rabbit. Dependent on the immunogenicity of the antigen, high antibody-titres (up to 1:100,000-1:1,000,000) may be achieved after only one or 2 or 3 or 4 or more boost immunizations. Thus, booster immunizations may be carried out on day 10, 20 and 30 using incomplete Freund's adjuvant and about half the amount of antigen (as compared with the initial immunization). Specific antibody should be detected by day 30 in the eggs or serum. For prolonged antibody production, chickens may receive additional booster immunizations, for example. In the case of a bird, such as a chicken, a hen normally lays eggs continuously for about 72 weeks and thereafter the laying capacity decreases. Eggs or serum may be collected as necessary and antibodies may then be recovered from the eggs, typically from the egg yolk.

Various IgY extraction methods are reviewed, for example, in detail by De Meulenaer & Huyghebaert (Food Agricult. Immunol. 2001; 13:275-288; for review see also Schade et al. Altern. Lab Anim. 2005; 33:129-154). In general, these methods can be divided into three principal groups:

1. Precipitation methods: involving ammonium or sodium sulphate, polyethyleneglycol (PEG), caprylic acid and caragenean.
2. Chromatographic methods: affinity chromatography, ion exchange chromatography, hydrophobic interaction chromatography, thiophylic interaction chromatography, and gel-filtration chromatography.
3. Ultrafiltration.

The purity of an IgY preparation can be increased by a combination of methods; for example, PEG precipitation can be combined with affinity chromatography or ammonium sulfate precipitation can be combined with Ion Exchange Chromatography. In some instances, depending on the final application, a water extract of IgY may be sufficient. Any combination of suitable methods may be used to recover an IgY preparation.

Transgenic Animals

A benefit of the present invention is that it obviates the need for the generation of a transgenic animal phylogenetically distal to a human, as variable regions and nucleic acids of an immunized animal suitable for the invention may be directly paired with a human variable region to form a mixed binding domain directly. Accordingly, a phage display library of mixed binding domains may be directly generated from a wild-type antibody repertoire of an animal suitable for use in the invention without the need to generate a transgenic variety of such an animal that includes human Ig loci or DNA. The phage displays a mixed binding domain comprising a variable region from the immunized animal and a cognate human variable region.

Optionally, an animal phylogenetically distal to a human which is immunized in order that a binding domain or multimer or a variant thereof of the invention may be generated may be a transgenic animal, for example by generation of a transgenic bird as described herein. Such a transgenic animal may comprises, at least in its B cell lineage, a nucleic acid encoding an immunoglobulin light chain or heavy chain.

The transgenic bird may be one wherein the heavy- or light-chain encoding sequence is provided with a means that renders it resistant to DNA rearrangements and/or somatic hypermutations.

The nucleic acid preferably encodes a human, human-like or humanized immunoglobulin chain. Preferably, the transgenic animal may be one, wherein the nucleic acid sequence encodes a light chain encoding sequence which is a human VK sequence or a human V lambda sequence. Preferably, the light chain is a human common light chain, for example as described herein.

Chickens, for example, have a heavy chain locus and a lambda light chain locus, but no kappa light chain locus. A human common light chain, for example, may be incorporated into the heavy chain locus or the lambda light chain locus of a chicken.

Methods for the preparation of non-human animals such as birds have been previously described in WO2009/15771 which is hereby incorporated by reference. Methods for the generation of transgenic chickens may be found in Ching et al., MABS 2018, 10(1), 71-80.

Method for Making a Binding Domain, Multimer, Such as an Antibody, or a Variant Thereof of the Invention The invention relates to a method for the preparation of a binding domain or multimer or a variant thereof of the invention, which method comprises:

immunizing an animal suitable for use in the invention with an antigen;

isolating from said animal a nucleic acid encoding a variable region which binds the antigen; and obtaining the variable region encoded by said nucleic acid and pairing said variable region with a cognate human variable region.

thereby to prepare a mixed binding domain, multimer, antibody or a variant thereof.

Such pairing may be carried out by expressing a nucleic acid encoding a variable region from the animal or based on, derived or obtained from a nucleic acid of the animal and a nucleic acid encoding the cognate human variable region such that the encoded variable regions may pair and thus generate a binding domain.

This may be carried out by expressing the two nucleic acid encoding the two variable regions of a binding domain in a suitable cell, which expresses said binding domain.

The invention relates a method for the preparation of a display library displaying a variety of mixed binding domains of the invention, which method comprises integrating a nucleic acid into an organism, such as a phage or yeast, or other vessel for peptide display, encoding a mixed binding domain of the invention, wherein said organism expresses and displays said binding domain on the surface of said organism or vessel. Multiple binding domains, typically multiple different binding domains may be displayed on the surface of multiple organisms, such as phages (each phage displaying one binding domain) by use of phage display library.

Thus, in a display library, a plurality of variable regions encoded by nucleic acids based on, derived or obtained from a nucleic acid of an immunized animal are paired with a plurality of human variable regions or are paired with a human common chain variable region. The display library may be, for example, a Fab phage display library.

The phage in a phage display library displays a mixed binding domain comprising a variable region from the immunized animal and a cognate human variable region. Phage display allows the selection of variable regions from the immunized animal that may be paired with a cognate variable region from a human. Thus, the binding domain is half humanized in this process. Binding domains in which the variable region from the immunized animal causes the binding to the antigen may be selected, for example using the antigen.

Expression of binding domains in cells and in phage display libraries is described in more detail below.

The invention also provides a method for producing a mixed binding domain of an antibody or fragment thereof, the method comprising combining a human light chain variable region, in particular a human common light chain variable region, with a heavy chain variable region encoded by a nucleic acid based on, derived or obtained from an animal phylogenetically distal from a human, such as a bird. Alternatively, the method may comprise combining a human heavy chain variable region, in particular a human common heavy chain variable region, with a light chain variable region encoded by a nucleic acid based on, derived or obtained from an animal phylogenetically distal from a human, such as a bird.

The invention also provides a method of producing a nucleic acid encoding a chimeric immunoglobulin binding domain by use of a transgenic animal, the method comprising:

(a) providing an animal whose genome comprises in its germline unrearranged immunoglobulin heavy chain V, D, and J gene segments and a human rearranged common light chain, wherein the animal in response to an antigen produces an antibody that comprises a heavy chain variable region encoded by the rearranged immunoglobulin heavy chain variable region;

(b) stimulating an immune response in the animal by exposing the animal to an antigen;

(c) isolating nucleic acid encoding the heavy chain variable region of the antibody;

(d) operably linking the DNA encoding the heavy chain variable region of the antibody to DNA encoding a human heavy chain constant region in a cell;

(e) integrating DNA encoding said human rearranged common light chain into said cell;

(f) growing the cell under conditions such that the cell expresses a binding domain comprising the heavy chain variable region and the human heavy chain constant region, and the human common light chain, which are capable of pairing; and (g) recovering the binding domain.

Such methods may comprise identification of a suitable animal for use of rearranged variable regions to generate a binding domain of the invention, including a step of determining the number of contact points between a rearranged variable region encoded by the nucleic acid of said animal and a human VL region interface. Preferably, a nucleic acid is selected that encodes a variable region that includes substantially the same electrostatic contact points at the human/animal variable region interface as exists for a human VH and human VL interface, preferably as in the interface of human Fab comprising a heavy chain variable region having SEQ ID NO: 1 and a light chain variable region having SEQ ID NO: 7, comprising 4, preferably 5, preferably 8 and more preferably 10 electrostatic interactions with a human VL region at said interface.

Display Library Technology

Various forms of display technologies including phage display, yeast display, ribosome display, mRNA display, among others, are known in the art, and encompassed by the invention described herein, for use of the binding domains described herein.

The following discussion focuses on phage display, but such description is not limiting and based on the description provided herein, could readily be applied to other forms of display technology.

Phage display is a prominent technique used including for the study of protein-protein, protein-peptide, and protein-DNA interactions that uses bacteriophages which are viruses that infect bacteria. Many of the protocols described herein are standard protocols for the construction of phage display libraries and the panning of phages for binding to an antigen of interest and are described in Antibody Phage Display: Methods and Protocols (editor(s): Philippa M. O'Brien, Robert Aitken). Libraries may be grown and harvested according to procedures know in the art, for example, as described by Kramer et al. 2003 (Kramer et al. 2003. Nucleic Acids Res. 31(11): e59) using VCSM13 (Stratagene) as helper phage strain. Phages may be grown and processed according to procedures known in the art, for example, as described by Kramer et al. 2003 (Kramer et al. 2003. Nucleic Acids Res. 31(11): e59) using VCSM13 as helper phage strain.

In the exemplary technique, a nucleic acid encoding a protein of interest, for example a nucleic acid encoding a variable region, is integrated into a phage coat protein gene, causing the phage to "display" the protein on its outside while containing the nucleic acid encoding for the protein on its inside. In this way, a connection between genotype and phenotype is established.

With regard to antibody discovery, in phage display, large collections (libraries) of VH and/or VL regions may be expressed on the surface of filamentous bacteriophage particles so that they pair to form binding domains. From these libraries, phages may be selected through binding interaction with an antigen and the displayed binding domain.

Thus, the displaying phages can be screened against other proteins, peptides or DNA sequences, or other forms of targets moieties, to detect interaction between the displayed VH, VL or binding domain and those other moeities. In this way, large libraries of VH, VL or binding domains can be screened and amplified in a process called in vitro selection, which is analogous to natural selection.

Accordingly, a binding domain of the invention may be displayed on phage, Typically, one of the variable regions in such a binding domain is based on, obtained or derived from, at least in part, a nucleic acid of an immunized animal as described herein, and also comprises a human variable region, preferably a common chain, more preferably a common light chain. Therefore, phage displaying the binding domain may be selected using the antigen that was used in to immunize the animal.

The invention thus provides a phage which comprises in its genome: a nucleic acid sequence encoding a first variable region encoded by a nucleic acid based on, derived or obtained from, at least in part, a nucleic acid of an animal that is phylogenetically distal to a human, preferably a bird, more preferably a chicken, duck or ostrich; and a nucleic acid sequence encoding a second human variable region. Preferably, the second variable region is capable of pairing with said first variable region.

The invention also provides a method for the preparation of a phage which comprises in its genome, a first variable region encoded by a nucleic acid based on, derived or obtained from, at least in part, a nucleic acid of an animal that is phylogenetically distal to a human, preferably a bird, more preferably a chicken, duck or ostrich; and a nucleic acid sequence encoding a second human variable region capable of pairing with said first variable region. Such a method comprises:

immunizing a bird with an antigen;

isolating from said animal a nucleic acid encoding a first variable region; and incorporating into the genome of a phage the said nucleic acid and a nucleic acid encoding a second human variable region which is capable of pairing with the first variable region, thereby to prepare a phage.

More generally, according to the invention, there is provided a method for generating binding domains using phage display. Such a method may comprise:

(a) immunizing a suitable animal with an antigen, such as a bird as is described herein, (b) obtaining one or more nucleic acids encoding a variable region from the animal (c) incorporating the one or more nucleic acids into one or more phage together with a nucleic acid encoding a cognate human variable region, so that each phage displaying two variable regions which are capable of pairing;

(d) selecting phage which displays a binding domain capable of binding to the antigen that was used in (a).

The following describes in more detail steps that may be followed in phage display screening to identify polypeptides, in this case binding domains comprising paired variable domains, that bind with high affinity to desired target protein or DNA sequence. The process can mimic immune selection, and antibodies with many different binding specificities have been isolated using this approach (Hoogenboom, H. R., et al. (2005). Nat. Biotechnol., 23, 1105).

1. The target protein (i.e. antigen used to immunize an animal) is typically immobilized to the wells of, for example, a microtiter plate.

In this step, the target protein may be any antigen that is used to immunize the animal and to which it is desired to generate antibodies. The types of animal that may be used in the invention and methods for immunizing them are described herein.

2. One or more nucleic acids encoding variable sequences are isolated from the animal that has been immunized with the target protein.

Typically, however, a large number of nucleic acid sequences encoding different variable regions capable of binding an antigen of interest are isolated from the animal. Typically the nucleic acids that are isolated are nucleic acids encoding VH sequences.

Isolation of nucleic acids from an animal typically begins with the recovery of appropriate tissue from the animal, for example spleen, bone marrow, or lymph node tissue, i.e. a tissue that comprises B cells. Cell suspensions may be prepared from such tissues and nucleic acids encoding variable sequences may then be isolated from the cell suspensions. Methods for preparing suitable cell suspensions, for example using Trisol are well known in the art. If desired, the splenic B cell fraction the splenic B cells may be purified by, for example, positive selection on the basis of CD19 selection. RNA may then be prepared from the cells and cDNA synthesized from the said RNA according to methods well known in the art.

PCR primer sets are then used that specifically amplify variable region encoding sequences from the cDNA (typically VH encoding sequences are amplified). This approach is described in De Haard et al. (J Biol Chem. 1999 Jun. 25; 274(26):18218-30), and specific primer sets for chicken are described in the Examples. Typically, primers are designed to introduce unique restriction enzyme sites at the 5" and 3' ends of amplified nucleic acids encoding VHs to facilitate cloning of the nucleic acids into a suitable phage display vector, for example a phagemid.

3. Nucleic acids encoding variable regions, such as VH regions, obtained from the animal may be used to generate a phage display library Phagemid vectors may be used to direct expression of binding domains of the invention in bacterial cells or to the surface of phage. A phagemid is a plasmid that contains an f1 origin of replication from an f1 phage. It can be used as a type of cloning vector in combination with filamentous phage M13. A phagemid can be replicated as a plasmid and also be packaged as single stranded DNA in viral particles. Phagemids contain an origin of replication (ori) for double stranded replication, as well as an f1 on to permit single stranded replication and packaging into phage particles.

Thus, a phagemid can be used to clone DNA fragments and be introduced into a bacterial host by a range of techniques, such as transformation and electroporation. Infection of a bacterial host containing a phagemid with a 'helper' phage provides the necessary viral components to permit single stranded DNA replication and packaging of the phagemid DNA into phage particles. The 'helper' phage infects the bacterial host by first attaching to the host cell's pilus and then, after attachment, transporting the phage genome into the cytoplasm of the host cell. Inside the cell, the phage genome triggers production of single stranded phagemid DNA in the cytoplasm. This phagemid DNA is then packaged into phage particles. The phage particles containing ssDNA are released from the bacterial host cell into the extracellular environment.

Accordingly, nucleic acids encoding variable regions isolated from an immunized animal suitable for the invention (or based on, derived or obtained from nucleic acid of such an animal) may be cloned into a phagemid vector together a nucleic acid encoding a cognate variable region. That is to say, each phagemid comprises a nucleic acid encoding a variable region isolated from the animal and a nucleic acid encoding its cognate variable region, for example the variable region of a cLC. It may be preferred that constant regions are also present to in order that a Fab fragment may be displayed when the phagemid is packaged into a phage.

A multiplicity of phagemids may be transformed or transfected into suitable bacterial cells in order to generate a library. In order to rescue phage from the library, a helper phage, for example VCSM13, is added to the bacterial cells and phage subsequently recovered using techniques well known to those skilled in the art.

4. The resulting phage-display library may then be added to a microtiter plate containing the target of interest, i.e. antigen, and after allowing the phage time to bind to said target, the dish may be washed.
5. Phage-displaying proteins that interact with the target molecules remain attached to the dish, while all others are washed away.
6. Attached phage may be eluted and used to create more phage by infection of suitable bacterial hosts. The new phage constitutes an enriched mixture, containing considerably less irrelevant phage (i.e. non-binding) than were present in the initial mixture.
7. Steps 4 to 6 may optionally be repeated one or more times, further enriching the phage library in binding proteins.
8. The nucleic acid (encoding the variable region based on, derived or obtained from a nucleic acid of an animal suitable for the invention) within the interacting phage may be sequenced to identify the interacting proteins or protein fragments.

In particular therefore, a method for the preparation of a phage display library, which comprises:

immunizing a bird animal with an antigen;

isolating a plurality of nucleic acids encoding a plurality of variable regions from said animal; and preparing a phage display library using said nucleic acids, wherein at least a portion of the variable regions encoded by said nucleic acids are paired with a human variable region, thereby to prepare a Fab phage display library.

Thus, one aspect of the invention provides a method for producing a population of binding domains, said method comprises at least the following steps:

a) providing a population of B cells
b) isolating nucleic acids from said B cells,
c) amplifying nucleic acid sequences encoding immunoglobulin heavy chain variable regions in said sample
d) at least partial sequencing of essentially all amplification products
e) performing a frequency analysis of all sequences from step d)
f) selecting the desired VH sequences,
g) providing a host cell with at least one vector comprising at least one of said desired VH sequences and at least one nucleic acid encoding a human light chain variable region;
h) culturing said host cells and allowing for expression of VH and VL polypeptides,
i) obtaining said binding molecules.

Alternatively, step c) and d) can be replaced by the alternative steps c' and d': c') constructing a cDNA library that is screened for VH region specific DNA sequences by probing with a nucleic acid probe specific for VH regions sequences and d') at least partial sequencing of clones containing VH inserts.

The invention further comprises the production of an antibody upon developing a phage display library and screening to identify a variable region that binds the target of interest. The method comprises:

a) isolating nucleic acid encoding the heavy chain variable region of a phage which displays a binding domain capable of binding to the antigen above;
b) operably linking the DNA encoding the variable region to DNA encoding a human heavy chain constant region;

c) integrating said variable region DNA and DNA encoding a human common light chain into a host cell;

d) growing the cell under conditions such that the cell expresses an antibody comprising the variable region operably linked to the human heavy chain constant region paired with the human common light chain, which are capable of pairing; and e) recovering the antibody.

Often, antibodies obtained from phage display libraries are subjected to in vitro affinity maturation to obtain high affinity antibodies (Hoogenboom, H. R., et al. (2005). Nat. Biotechnol., 23, 1105).

A phage of the invention, for example one identified by the procedures set out above, will typically be capable of displaying the variable region encoded by a nucleic acid based on, derived or obtained at least in part from a nucleic acid of a bird and a human variable region, wherein the said variable regions are paired with each other.

A phage display library according to the invention comprises a plurality of phagemids or phages. A phage display library of the invention may comprise up to $10^{10}$ nucleic acids each encoding a different variable region from a bird, for example up to $10^9$ or up to $10^8$ nucleic acids each encoding a different variable region from a bird. In a phage display library of the invention, substantially all phage display a binding domain of the invention, for example in the form of a Fab.

A phage library may be screened to identify binding domains that are capable of binding to the antigen used for immunization according to methods well known to those skilled in the art, for example by the use of FACS analysis. Thus, binding regions which have affinity and specificity for the antigen used to immunize the animal may be identified by screening using the said antigen. A fraction of binding regions display in a library may actually bind the antigen used to immunize. Some variable regions derived from the immunized animal may not bind the antigen (i.e. have a different specificity) and for others there may be a VH/VL pair formed in which the binding region has lost affinity or specificity due to alternative VH-VL CDR pairing.

Common Chain

It is a preferred aspect of the present invention that a binding domain or multimer thereof, such as an antibody, of the invention has a common light chain (variable region) that can combine with an array of heavy chain variable regions encoded by a nucleic acid based on, derived or obtained from a nucleic acid of an animal phylogenetically distal to a human, preferably a bird, more preferably a chicken, to form an antibody with functional antigen binding domains (WO2004/009618, WO2009/157771).

A common light chain (variable region) for use in the multivalent antibody of the invention is preferably a human light chain (variable region). A common light chain (variable region) preferably has a germline sequence. A preferred germline sequence is a light chain variable region that is frequently used in the human repertoire and has good thermodynamic stability, yield and solubility. A preferred germline light chain is the rearranged germline human kappa light chain IgVκ1-39*01/IGJκ1*01 (FIG. 17A; SEQ ID NO: 5). The common light chain variable region is preferably the variable region of the rearranged germline human kappa light chain IgVκ1-39*01/IGJκ1*01 (FIG. 17B; SEQ ID NOs: 6 and 7). A common light chain preferably comprises a light chain variable region as depicted in FIG. 17B or 17D (SEQ ID NOs: 7 or 10 respectively) with 0-5 amino acid insertions, deletions, substitutions, additions or a combination thereof.

Another preferred common light chain is the human kappa light chain IgVκ1-39/IGJκ5 (FIG. 19G; SEQ ID NO:25). Preferably, an antibody of the invention comprises the variable region of human kappa light chain IgVκ1-39/ IGJκ5.

A further preferred common light chain is the human kappa light chain IgVκ3-15/IGJκ1 (FIG. 19H; SEQ ID NO: 94). Preferably, an antibody of the invention comprises the variable region of human kappa light chain IgVκ3-15/IGJκ1.

A further preferred common light chain is the human kappa light chain IgVκ3-20/IGJκ1 (FIG. 19I; SEQ ID NO: 95). Preferably, an antibody of the invention comprises the variable region of human kappa light chain IgVκ3-20/IGJκ1.

A further preferred common light chain is the human lambda light chain IgVλ3-21/IGJλ3 (FIG. 19J; SEQ ID NO: 96). Preferably, an antibody of the invention comprises the variable region of human kappa light chain IgVλ3-21/ IGJλ3.

The common light chain preferably further comprises a light chain constant region, preferably a kappa light chain constant region. A nucleic acid that encodes the common light chain can be codon optimized for the cell system used to express the common light chain protein. The encoding nucleic acid can deviate from a germ-line nucleic acid sequence.

The common light chain (variable region) for use in the binding domain or multimer thereof, such as multivalent antibodies, of the invention can be a lambda light chain, such as the human lambda light chain IgVλ3-21/IGJλ3 (FIG. 19J), and this is therefore also provided in the context of the invention. The common light chain of the invention may comprise a constant region of a kappa or a lambda light chain. It is preferably a constant region of a kappa light chain, preferably wherein said common light chain is a germline light chain, preferably a rearranged germline human kappa light chain comprising the IgV$_K$1-39 gene segment, for example the rearranged germline human kappa light chain IgV$_K$1-39*01/IGJ$_K$1*01 (FIG. 17A); the human kappa light chain IgVκ1-39/IGJκ5 (FIG. 19G); the human kappa light chain IgVκ3-15/IGJκ1 (FIG. 19H); or the human kappa light chain IgVκ3-20/IGJκ1 (FIG. 19I). Those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions.

IgVκ1-39 is short for Immunoglobulin Variable Kappa 1-39 Gene. The gene is also known as Immunoglobulin Kappa Variable 1-39; IGKV139; IGKV1-39. External Ids for the gene are HGNC: 5740; Entrez Gene: 28930; Ensembl: ENSG00000242371. A preferred amino acid sequence for IgVκ1-39 is given in FIG. 17. This lists the sequence of the V-region. The V-region can be combined with one of five J-regions. FIG. 17 describes two preferred sequences for IgVκ1-39 in combination with a J-region. The joined sequences are indicated as IGKV1-39/jk1 and IGKV1-39/jk5; alternative names are IgVκ1-39*01/ IGJκ1*01 or IgVκ1-39*01/IGJκ5*01 (nomenclature according to the IMGT database worldwide web at imgt.org). These names are exemplary and encompass allelic variants of the gene segments.

IgVκ3-15 is short for Immunoglobulin Variable Kappa 3-15 Gene. The gene is also known as Immunoglobulin Kappa Variable 3-15; IGKV315; IGKV3-15. External Ids for the gene are HGNC: 5816; Entrez Gene: 28913; Ensembl: ENSG00000244437. A preferred amino acid sequence for IgVκ3-15 is given in FIG. 19D (SEQ ID NO: 90). This lists the sequence of the V-region. The V-region can be combined with one of five J-regions. The V-region can be combined with one of five J-regions. FIG. 19A describes the preferred sequence for IgVκ3-15 in combination with a J-region. The joined sequence is indicated as IGKV3-15/jk1; alternative name is IgVκ3-15*01/IGJκ1*01 (nomenclature according to the IMGT database worldwide web at imgt.org). This name is exemplary and encompasses allelic variants of the gene segments.

IgVκ3-20 is short for Immunoglobulin Variable Kappa 3-20 Gene. The gene is also known as Immunoglobulin Kappa Variable 3-20; IGKV320; IGKV3-20. External Ids for the gene are HGNC: 5817; Entrez Gene: 28912; Ensembl: ENSG00000239951. A preferred amino acid sequence for IgVκ3-20 is given in FIG. 19E (SEQ ID NO: 91). This lists the sequence of the V-region. The V-region can be combined with one of five J-regions. FIG. 19B describes the preferred sequence for IgVκ3-20 in combination with a J-region. The joined sequence is indicated as IGKV3-20/jk1; alternative name is IgVκ3-20*01/IGJκ1*01 (nomenclature according to the IMGT database worldwide web at imgt.org). This name is exemplary and encompasses allelic variants of the gene segments.

IgVλ3-21 is short for Immunoglobulin Variable Lambda 3-21 Gene. The gene is also known as Immunoglobulin Lambda Variable 3-21; IGLV320; IGLV3-21. External Ids for the gene are HGNC: 5905; Entrez Gene: 28796; Ensembl: ENSG00000211662.2. A preferred amino acid sequence for IgVλ3-21 is given in FIG. 19K (SEQ ID NO: 97). This lists the sequence of the V-region. The V-region can be combined with one of five J-regions. FIG. 19J describes the preferred sequence for IgVλ3-21 in combination with a J-region. The joined sequence is indicated as IGλV3-21/jk3; alternative name is IgVλ3-21/IGJκ3 (nomenclature according to the IMGT database worldwide web at imgt.org). This name is exemplary and encompasses allelic variants of the gene segments.

A cell that produces a common light chain can produce for instance rearranged germline human kappa light chain IgVκ1-39*01/IGJκ1*01 and a light chain comprising the variable region of the mentioned light chain fused to a lambda constant region. Where herein reference is made to a germ-line sequence it is preferred that the variable region is a germ-line sequence.

A preferred common light chain for use in a binding domain or multimer thereof, such as an antibody, of the invention is one comprising the sequence set out in SEQ ID NO: 5.

The common chain for use in the binding domain or multimer thereof, such as an antibody, of the invention can also be a heavy chain and this is therefore also provided in the context of the invention. Common heavy chains have been used in the art to make bispecific antibodies, and can be used here in making a multivalent antibody comprising three or more binding domains, two or more of said binding domains comprise a common heavy chain known in the art. For example, the use of antibody libraries in which the heavy chain variable domain is the same for all the library members and thus the diversity is based on the light chain variable domain are described, for example, in PCT/US2010/035619, and PCT/US2010/057780, each of which is hereby incorporated by reference in its entirety. These and other techniques to generating binding domains having common heavy chains can be generated by the skilled artisan, and can be employed in the present invention.

Production of a Multimer of the Invention

A multimer of the invention, for example an antibody, may be produced by co-transfection of individual cells with one or more genetic constructs which together encode the two or more, for example three, proteins that form the multimer such as those described above. For example, a host cell may be co-transfected with nucleic acid sequences encoding one or more heavy chain variable regions, based on, derived or obtained from a nucleic acid of an immunized animal suitable for the invention or from a display library according to the methods described above, and a common light chain variable region to produce an antibody. Alternatively, an antibody of the invention may be produced by co-transfection of individual cells with one or more genetic constructs which together encode one or more light chain variable regions and a common heavy chain. Multiple heavy chain variable regions or multiple light chain regions may be expressed from a cell in the event that a multispecific multimer, for example a bispecific antibody is desired.

In the event that a multispecific antibody, such as a bispecific antibody is desired, several methods have been published to favor the production of antibodies which are heterodimers. In the present invention it is preferred that the cell favors the production of the heterodimers over the production of the respective homodimers. This is typically achieved by modifying the constant region of the heavy chains such that they favor heterodimerization (i.e. dimerization with one heavy chain combining with the second heavy chain) over homodimerization. In a preferred embodiment the antibody of the invention comprises two different immunoglobulin heavy chains with compatible heterodimerization domains.

The compatible heterodimerization domains are preferably compatible immunoglobulin heavy chain CH3 heterodimerization domains. When wildtype CH3 domains are used, co-expression of two different heavy chains (A and B) and a common light chain will result in three different antibody species, AA, AB and BB. AA and BB are designations for the two homodimer antibodies and AB is a designation for the heterodimer antibody. To increase the percentage of the desired heterodimer product (AB) CH3 engineering can be employed, or in other words, one can use heavy chains with compatible hetero-dimerization domains, as defined hereunder. The art describes various ways in which such hetero-dimerization of heavy chains can be achieved.

The term 'compatible hetero-dimerization domains' as used herein refers to protein domains that are engineered such that engineered domain A' will preferentially form heterodimers with engineered domain B' and vice versa, homo-dimerization between A'-A' and B'-B' is diminished.

In U.S. Ser. No. 13/866,747 (now issued as U.S. Pat. No. 9,248,181), U.S. Ser. No. 14/081,848 (now issued as U.S. Pat. No. 9,358,286), WO2013/157953 and WO2013/157954, methods and means are disclosed for producing multivalent antibodies using compatible heterodimerization domains. These means and methods can also be favorably employed in the present invention. Specifically, an antibody of the invention preferably comprises mutations to produce essentially only bispecific full length IgG molecules.

Preferred mutations are the amino acid substitutions L351K and T366K (EU numbering) in the first CH3 domain or at positions corresponding thereto (the 'KK-variant' heavy chain) and the amino acid substitutions L351 D and L368E in the second domain or at positions corresponding thereto (the 'DE-variant' heavy chain), or vice versa. It was previously demonstrated in our U.S. Pat. Nos. 9,248,181 and 9,358,286 as well as the WO2013/157954 PCT application that the DE-variant and KK-variant preferentially pair to form heterodimers (so-called 'DEKK' bispecific molecules). Homodimerization of DE-variant heavy chains (DEDE homodimers) or KK-variant heavy chains (KKKK homodimers) hardly occurs due to repulsion between the charged residues in the CH3-CH3 interface between identical heavy chains.

In WO2019/190327, a method for the production of multivalent antibodies, for example trispecific or multispecific antibodies, is described. Modular formats for a multivalent antibody comprising three or more binding domains are described: in these formats, at least one binding domain is connected to a base antibody portion, said base antibody portion comprising two binding domains. The additional binding domain may comprise a variable region, Fv domain, a Fab domain or a modified Fab domain or a functional fragment of any thereof. The base antibody portion may be, for example, a full length antibody or fragment thereof, but in each case comprises two binding domains. The one or more additional binding domains are connected to the base antibody portion via a linker(s), providing one or more binding moieties in addition to those of the base antibody portion. A linker is used to connect the one or more additional binding domains to the base antibody portion. The linker comprises a peptide region, for example one or more hinge regions and/or one or more regions derived from a hinge region. A binding domain or multimer of the invention may be incorporated into such a multivalent antibody.

Nucleic Acid Sequences, Polypeptides, Vectors and Cells

The invention further provides nucleic acid sequences encoding polypeptides that may be used in the assembly of a multimer, such as an antibody, of the invention; vectors comprising such nucleic acid sequences; a cell which is capable of producing a multimer, such as an antibody, of the invention; and a method for the preparation of such a multimer, including an antibody, using such a cell.

Multimers, such as antibodies, according to the invention are typically produced by cells that express nucleic acid sequences encoding the polypeptides that together assemble to form a multimer, such as an antibody, of the invention.

The nucleic acid sequences employed to make the polypeptides of a multimer, such as an antibody, of the invention may be placed in any suitable expression vector and, in appropriate circumstances, two or more vectors in a single host cell.

Generally, nucleic acid sequences encoding variable domains are cloned with the appropriate linkers and/or constant regions and the sequences are placed in operable linkage with a promoter in a suitable expression construct in a suitable cell line for expression.

Accordingly, the invention also provides a method for the preparation of a multimer, such as an antibody, which method comprises:

providing a cell which comprises one or more nucleic acid sequences encoding polypeptides which are capable of assembly into a multimer, such as an antibody, of the invention; and cultivating said cell under conditions to provide for expression of the polypeptides and for their assembly into a multimer, such as an antibody.

In particular, the cell is provided with one or more nucleic acid sequences based on, derived or obtained from an animal phylogenetically distal from a human, and which nucleic acid sequences encode an immunoglobulin heavy or light chain variable region. If the cell is provided with one or more nucleic acid sequences encoding an immunoglobulin heavy chain variable region, the cell also comprises a nucleic acid encoding an immunoglobulin light chain variable region, preferably a common light chain variable region, such as those described herein. If the cell is provided with one or more nucleic acid sequences encoding an immunoglobulin light chain variable region, the cell also comprises a nucleic acid encoding an immunoglobulin heavy chain variable region, preferably a common heavy chain variable region. The cell further comprises one or more nucleic acids encoding heavy and/or light chain constant regions.

A host cell of the present invention may be capable of producing a multimer, such as an antibody, of the invention at a purity of at least about 50%, at least about 60%, least about 70%, at least about 80%, at least about 90%, at least about 95%, at least about 98% of the multimer, such as an antibody, of the invention on the basis of total expressed immunoglobulin.

A host cell of the invention may be capable of producing a multimer, such as an antibody, of the invention, wherein at least about 50%, at least about 60%, least about 70%, at least about 80%, at least about 90%, at least about 95%, at least about 98% of the multivalent antibody produced comprises a variable rearranged region paired with a cognate common chain for all binding sites.

A host cell of the invention may be capable of producing an antibody, wherein at least about 50%, at least about 60%, least about 70%, at least about 80%, at least about 90%, at least about 95%, at least about 98% of the common chain expressed is paired to the multivalent antibody and is not free, unassociated protein.

Expression of a Binding Domain or a Multimer, Such as an Antibody, or a Variant Thereof Expression of binding domains, multimers, such as antibodies, or variants thereof in recombinant host cells has been described in the art. The nucleic acid molecules encoding the variable regions in the case of a binding domain and the light and heavy chains of an antibody of the invention may be present as extrachromosomal copies and/or stably integrated into the chromosome of the host cell. The latter is preferred in which case a locus may be targeted that is known for lack of gene silencing.

To obtain expression of nucleic acid sequences encoding the polypeptides which assemble into a multimer, such as an antibody, of the invention, it is well known to those skilled in the art that sequences capable of driving such expression can be functionally linked to the nucleic acid sequences encoding the polypeptides. Functionally linked is meant to describe that the nucleic acid sequences encoding the polypeptides or precursors thereof are linked to the sequences capable of driving expression such that these sequences can drive expression of the polypeptides or precursors thereof. Useful expression vectors are available in the art, e.g. the pcDNA vector series of Invitrogen. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. Promoters can be constitutive or regulated, and can be obtained from various sources, including viruses, prokaryotic, or eukaryotic sources, or artificially designed.

Expression of nucleic acid sequences of the invention may be from the natural promoter or a derivative thereof or from an entirely heterologous promoter. Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter, promoters derived from Simian Virus 40 (SV40), and the like. Suitable promoters can also be derived from eukaryotic cells, such as methallothionein (MT) promoters, elongation factor Ia (EF-Ia) promoter, actin promoter, an immunoglobulin promoter, heat shock promoters, and the like. Any promoter or enhancer/promoter capable of driving expression of a nucleic acid sequence of the invention in a host cell is suitable in the invention. In one embodiment the sequence capable of driving expression comprises a region from a CMV promoter, preferably the region comprising nucleotides −735 to +95 of the CMV immediate early gene enhancer/promoter. The skilled person will be aware that the expression sequences used in the invention may suitably be combined with elements that can stabilize or enhance expression, such as insulators, matrix attachment regions, STAR elements and the like. This may enhance the stability and/or levels of expression.

Any cell suitable for expressing a recombinant nucleic acid sequence may be used to generate a multimer, such as an antibody, of the invention. Preferably said cell is adapted for suspension growth.

A multimer, such as an antibody, of the invention may be expressed in host cells, typically by culturing a suitable cell of the invention and harvesting said multimer, such as an antibody, from said culture. Preferably said cell is cultured in a serum free medium. A multimer, such as an antibody, of the invention may be recovered from the cells or, preferably, from the cell culture medium by methods that are generally known to the person skilled in the art.

Further provided is multimer, such as an antibody, obtainable by a method for producing a, multimer, such as an antibody, according to the invention. The multimer, such as an antibody, is preferably purified from the medium of the culture.

After recovery, a multimer, such as an antibody, may be purified from the culture by using methods known in the art. Such methods may include precipitation, centrifugation, filtration, size-exclusion chromatography, affinity chromatography, cation- and/or anion-exchange chromatography, hydrophobic interaction chromatography, and the like. Affinity chromatography, including based on the linker sequence as a means of separating the multimer, such as an antibody, of the invention may be used.

Pharmaceutical Compositions and Methods of Use

Also provided by the invention is a pharmaceutical composition which comprises a binding domain or multimer, such as an antibody, of the invention or a variant thereof and a pharmaceutically acceptable carrier and/or diluent.

Accordingly, the invention provides a binding domain or multimer, such as an antibody, of the invention or a variant thereof as described herein for use in the treatment of the human or animal body by therapy.

Further provided by the invention is a method for the treatment of a human or animal suffering from a medical condition, which method comprises administering to the human or animal a therapeutically effective amount of a binding domain or multimer, such as an antibody, as described herein or a variant thereof.

The amount of binding domain or multimer, such as an antibody, according to the invention or a variant thereof to be administered to a patient is typically in the therapeutic window, meaning that a sufficient quantity is used for obtaining a therapeutic effect, while the amount does not exceed a threshold value leading to an unacceptable extent of side-effects.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

Aspects of the Invention:

1. A binding domain or a multimer or a variant thereof which comprises a variable region encoded by a nucleic acid based on, derived or obtained from an animal phylogenetically distal from a human, which variable region is paired with a human variable region.

2. A binding domain or a multimer or a variant thereof according to aspect 1, wherein the animal phylogenetically distal from a human is a bird.

3. A binding domain or a multimer or a variant thereof according to aspect 1 or 2, wherein the multimer is an antibody.

4. A binding domain or multimer or a variant thereof according to aspect 3, wherein the constant regions of the antibody are human constant regions.

5. A binding domain or multimer or a variant thereof according to any one of aspects 1-4, wherein the variable region encoded by a nucleic acid based on, derived or obtained from an animal phylogenetically distal from a human is a rearranged VDJ region encoded by a nucleic acid based on, derived or obtained from said animal and the human variable region is a light chain variable region.

6. A binding domain or multimer or a variant thereof according to aspect 5 which comprises a common light chain, such as a human common light chain.

7. A binding domain or multimer or a variant thereof according to any one of aspects 1-6, wherein the variable region encoded by a nucleic acid based on, derived or obtained from an animal phylogenetically distal from a human is a rearranged VJ region encoded by a nucleic acid based on, derived or obtained from said animal and the human variable region is a heavy chain variable region.

8. A binding domain or multimer or a variant thereof according to aspect 7, which comprises a common heavy chain.

9. A binding domain or multimer or a variant thereof according to any one of aspects 1-8, wherein the bird comprises a functional VH gene segment encoding a VH region comprising at least 5, preferably at least 8 and more preferably at least 10 electrostatic interactions with a human VL region at the VH/VL interface.

10. A binding domain or multimer or a variant thereof according to any one of aspects 2 to 9, wherein the bird is a Galliform, such as a chicken, a turkey, a grouse, a New World quail, an Old World quail, a ptarmigan, a partridge, a pheasant, a junglefowl, a bird of the family Cracidae, a goose swan, a duck or an ostrich.

11. A binding domain or multimer or a variant thereof according to any one of aspects 1-10, wherein the binding domain or multimer or a variant thereof binds to mouse and/or human CXCR4, preferably to human CXCR4.

12. A binding domain or multimer or a variant thereof according to aspect 11, wherein the variable region encoded by a nucleic acid based on, derived or obtained from an animal phylogenetically distal from a human is a heavy chain variable region comprising an amino acid sequence comprising SEQ ID NO: 100; SEQ ID NO: 101 or SEQ ID NO: 102, or having at least 80%, 85%, preferably at least 90%, 95%, more preferably at least 97%, 98% or 99%, sequence identity thereto.

13. A binding domain or multimer or a variant thereof according to any one of aspects 1-12, wherein the variable region encoded by a nucleic acid based on, derived or obtained from an animal phylogenetically distal from a human is humanized.

14. A binding domain or multimer or a variant thereof according to any one of aspects 3 to 13, which is a bispecific antibody.

15. A binding domain or multimer of a variant thereof according to any one of aspects 3 to 14, which is a multispecific antibody, for example a trispecific antibody.

16. A method for the preparation of a binding domain or a multimer or a variant thereof, which method comprises:
  immunizing an animal phylogenetically distal from a human with an antigen;
  isolating a nucleic acid sequence encoding a variable region from said animal;
  obtaining a variable region from said isolated nucleic acid sequence; and
  pairing the variable region from the said animal with a human variable region,
  thereby preparing a binding domain or multimer or a variant thereof.

17. A method according to aspect 16, wherein the animal phylogenetically distal from a human comprises a functional VH gene segment, comprising 5, preferably 8 and more preferably 10 electrostatic interactions with a human VL variable region at the VH/VL interface.

18. A method according to claim 16 or 17, wherein the nucleic acid sequence encoding a variable region from said animal is a nucleic acid sequence encoding a heavy chain variable region and the human variable region is a light chain variable region.

19. A method according to any one of aspects 16-18, wherein the variable region encoded by the isolated nucleic acid sequence from an animal phylogenetically distal from a human is a rearranged VDJ region and the human variable region is a light chain variable region.

20. A method according to aspect 18 or 19, which comprises a common light chain.

21. A method according to any one of aspects 1-18, wherein the variable region encoded by the isolated nucleic acid sequence from an animal phylogenetically distal from a human is a rearranged VJ region and the human variable region is a heavy chain variable region.

22. A method according to aspect 21, which comprises a common heavy chain.

23. A method according to any one of aspects 16-22, wherein the animal phylogenetically distal from a human is a bird, such as a Galliform, such as a chicken, a turkey, a grouse, a New World quail, an Old World quail, a ptarmigan, a partridge, a pheasant, a jungle-fowl, a bird of the family Cracidae, a goose swan, a duck or an ostrich.

24. A method according to any one of aspects 16-23, wherein the multimer is an antibody, which is a bispecific antibody.

25. A method according to any one of aspects 16-24, wherein the multimer is a multispecific antibody, for example a trispecific antibody.

26. A method according to any one of aspects 16-25, wherein the animal phylogenetically distal from a human is a transgenic chicken comprising, at least in its B cell lineage, a nucleic acid encoding an immuno-globulin light chain or heavy chain.

27. A method according to aspect 26, wherein the heavy or light chain encoding nucleic acid is provided with a means that renders it resistant to DNA rearrangements and/or somatic hypermutations.

28. A method according to aspect 27, wherein the sequence of the light chain encoding nucleic acid is a human $V_K$ sequence.

29. A phage which comprises in its genome:
  a nucleic acid encoding a variable region, which nucleic acid is based on, derived or obtained from an animal phylogenetically distal from a human; and
  a nucleic acid encoding a human variable region.

30. A phage according to aspect 29, wherein the nucleic acid sequence encoding a variable region from said animal is a nucleic acid sequence encoding a heavy chain variable region and the human variable region is a light chain variable region.

31. A phage according to aspect 29 or 30, wherein the phage is capable of displaying the variable regions encoded by the nucleic acids, wherein the said variable regions are paired with each other.

32. A phage according to any one of aspects 29-31, wherein the variable regions are paired with each other to form a binding domain.

33. A phage according to any one of aspects 29-32, wherein the binding domain is in the form of a Fab.

34. A phage display library comprising a phage according to any one of aspects 29-33, which library comprises at least about $10^6$ phages.

35. A method for the preparation of a phage display library, which method comprises:
  immunizing an animal phylogenetically distal from a human with an antigen;
  isolating a plurality of nucleic acids encoding variable regions from said animal; and
  preparing a phage display library using said nucleic acids encoding said variable regions,
  thereby preparing a phage display library.

36. A method according to aspect 35, wherein the plurality of nucleic acid sequences encoding variable regions from said animal are nucleic acid sequences encoding heavy chain variable regions.

37. A method according to aspect 35 or 36, wherein the phages in the phage display library comprise a nucleic acid sequence encoding a human light chain variable region.

38. A method according to any one of aspects 35-37, wherein the plurality of nucleic acids encoding variable regions from the said animal are used to prepare a plurality of phages, each comprising a said nucleic acid.

39. A method according to any one of aspects 35-38, wherein the phage display library comprises at least one phage which comprises in its genome:
  a nucleic acid encoding a variable region, which nucleic acid is based on, derived or obtained from an animal phylogenetically distal from a human; and
  a nucleic acid encoding a human variable region.

40. A method according to aspect 39, wherein the variable regions are paired with each other to form a binding domain.

41. A method according to aspect 40, wherein the binding domain is in the form of a Fab 42. A method for the identification of a binding domain or a multimer or a variant thereof according to any one of aspects 1-15 that is capable of binding to an antigen, which method comprises:

immunizing an animal phylogenetically distal from a human with an antigen;

isolating a plurality of nucleic acids encoding variable regions from the said animal; and preparing a phage display library using the said nucleic acids encoding the said variable regions; and identifying a phage in the phage display library capable of binding to the antigen, thereby identifying a binding domain or a multimer or a variant thereof capable of binding to the antigen.

43. A method according to aspect 42, wherein the binding domain or a multimer or a variant thereof binds to the antigen.

44. A method according to aspect 42 or 43, wherein the plurality of nucleic acid sequences encoding variable regions from said animal are nucleic acid sequences encoding heavy chain variable regions 45. A method according to any one of aspects 42-44, wherein the phages in the phage display library comprise a nucleic acid sequence encoding a human light chain variable region.

46. A nucleic acid or nucleic acids encoding: a polypeptide comprising a heavy chain variable region which nucleic acid or nucleic acids is/are based on, derived or obtained from an animal phylogenetically distal from a human; and a polypeptide comprising a human light chain variable region.

47. A nucleic acid or nucleic acids according to aspect 46, wherein the polypeptides are capable of pairing to form a binding domain or a multimer or a variant thereof.

48. A nucleic acid or nucleic acids according to aspect 46 or 47, wherein the nucleic acid or nucleic acids encode: at least two polypeptides comprising a heavy chain variable region, at least one of which is based on, derived or obtained from an animal phylogenetically distal from a human; and a polypeptide comprising a human light chain variable region.

49. A nucleic acid or nucleic acids according to aspect 48, wherein the at least two polypeptides comprising a heavy chain variable region and the polypeptide comprising a human light chain variable region are capable of assembly into a multimer.

50. A nucleic acid or nucleic acids according to aspect 49, wherein the multimer is an antibody, for example a bispecific antibody or a multispecific antibody.

51. A host cell comprising a nucleic acid or nucleic acids according to any one of aspects 46 to 50.

52 A phage according to any one of aspects 29 to 33, a phage display library according to aspect 34, a method for the preparation of a phage display library according to any one of aspects 35 to 41, a method for the identification of a binding domain or a multimer or a variant thereof according to any one of aspects 42-45 or a nucleic acid or nucleic acids according to any one of aspects 46 to 50 or a host cell according to aspect 51, wherein the animal phylogenetically distal from a human is a bird, such as a Galliform, such as a chicken, a turkey, a grouse, a New World quail, an Old World quail, a ptarmigan, a partridge, a pheasant, a jungle-fowl, a bird of the family Cracidae, a goose swan, a duck or an ostrich.

53. A pharmaceutical composition which comprises a binding domain or a multimer or a variant thereof according to any one of aspects 1-15 and a pharmaceutically acceptable carrier and/or diluent.

54. A pharmaceutical composition which comprises an antibody according to any one of aspects 1-15 and a pharmaceutically acceptable carrier and/or diluent.

55. A binding domain or multimer or a variant thereof according to any one of aspects 1-15 for use in the treatment of the human or animal body by therapy.

56. A method for the treatment of a human or animal suffering from a medical indication, which method comprises administering to the human or animal a therapeutically effective amount of a binding domain or multimer or a variant thereof according to any one of aspects 1-15.

57. An animal phylogenetically distal from a human which is a transgenic animal comprising, at least in its B cell lineage, a nucleic acid encoding a human immunoglobulin light chain or heavy chain.

58. An animal according to aspect 57 which is a chicken, turkey, grouse, New World quail, Old World quail, ptarmigan, partridge, pheasant, junglefowl, goose swan, duck or ostrich.

The following Examples illustrate the invention but are not intended to limit the invention in any way.

EXAMPLES

Example 1. Chimeric Chicken VH-Human VL Antibodies

To produce a phage display library which displays binding domains comprised of VH regions encoded by a nucleic acid based on, derived or obtained from a nucleic acid of an immunized bird, preferably a chicken, duck or ostrich, wherein such VH region forms a multimer with a human light chain variable region, preferably a cLC, the VH regions must be capable of pairing with the VL region.

Herein, it is demonstrated that the repertoire of VH regions based on, derived or obtained from a nucleic acid of an immunized bird, preferably a chicken are capable of stably pairing with a human VL. The human VLs exemplified herein comprise an amino acid sequence set out in SEQ ID NO: 7; SEQ ID NO: 10; SEQ ID NO: 87; SEQ ID NO: 88; or SEQ ID NO 89.

A Fab of an antibody comprises a heavy chain and a light chain part that when paired together form a binding domain structure that does not unfold. Herein, it is demonstrated that such structures can be assembled even when light and heavy chain variable regions from different species are combined even where the variable regions originate from V gene segments which have low homology at the primary amino acid level.

All sequence identities were determined in these Examples using the AlignX component of Vector NTI Advance 11.5.2 software (ThermoFisher Scientific), using default settings. The percent sequence identity between two nucleic acid sequences was determined using the AlignX application of the Vector NTI Program Advance 11.5.2 software using the default settings, which employ a modified ClustalW algorithm (Thompson, J. D., Higgins, D. G., and Gibson T. J. (1994) Nuc. Acid Res. 22: 4673-4680), the swgapdnamt score matrix, a gap opening penalty of 15 and a gap extension penalty of 6.66. Amino acid sequences were aligned with the AlignX application of the Vector NTI Program Advance 11.5.2 software using default settings, which employ a modified ClustalW algorithm (Thompson, J. D., Higgins, D. G., and Gibson T. J., 1994), the blosum62mt2 score matrix, a gap opening penalty of 10 and a gap extension penalty of 0.1.

Figure 1:
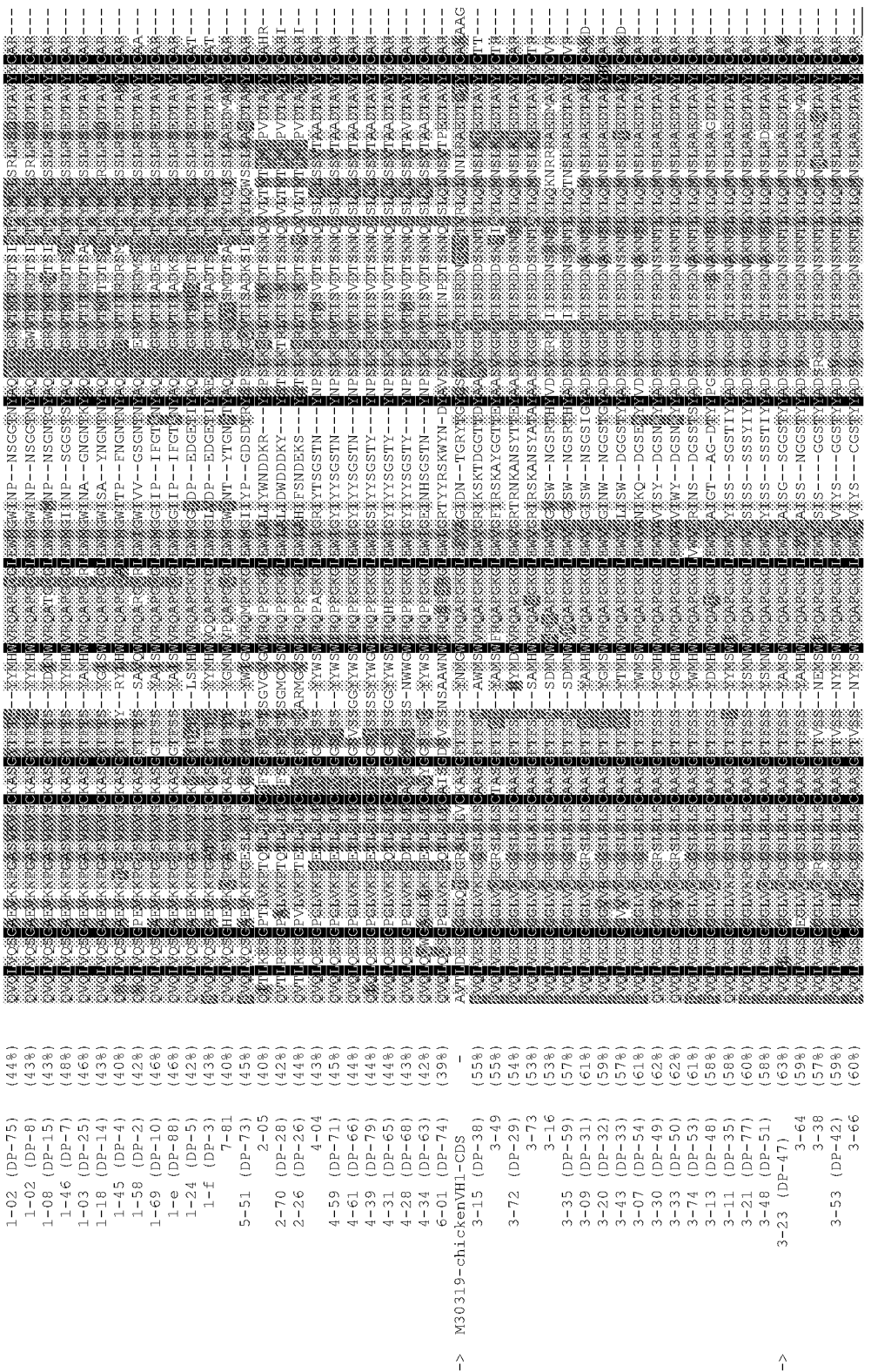
FIG. 1 sets out a protein sequence alignment of the amino acid sequences encoded by the one functional chicken VH gene segment (VH1) with 47 human germline VH gene segments that represent each of the 7 VH families, obtained via AlignX. Percentage identity for each human VH gene segment is given between brackets. AlignX is a component of Vector NTI Advance 11.5.2 software, and alignment is obtained using default settings.

1. The single functional chicken VH1 gene segment of SEQ ID NO: 14 is homologous to human VH gene segments as set out in the protein alignment shown in FIG. 1. It can be seen that the functional chicken VH1 gene segment has only low homology with human gene segments. The chicken gene segment and the human VH1-02 gene segment from which the heavy chain variable region having SEQ ID NO: 1 of human Fab3178 is derived (see below) have only 43% amino acid identity as set out in the protein alignment shown in FIG. 2. All sequence comparisons were carried out using the AlignX component of Vector NTI Advance 11.5.2 software, using default settings.

2. The FW4 region of the functional chicken JH gene segment is homologous to the corresponding region in human JH gene segments, with overall 73% amino acid identity as set out in the protein alignment shown in FIG. 3.

3. A 3D homology model of a human/chicken hybrid Fab was generated (see FIG. 4), based on the crystal structure of a human Fab comprising MF3178 (PDB entry 5O4O; containing a VH1-02 derived gene [Geuijen et al., 2018]) having SEQ ID NO: 1 and a VL having SEQ ID NO: 7. The algorithm used for homology modelling was MODELLER (https://salilab.org/modeller/). All structure analyses (including modelling) were carried out using Biovia Discovery Studio Software using default settings (http://accelrys.com/products/collaborative-science/biovia-discovery-studio/).

In the model, the human VH region was replaced by a modeled VH region based on the amino acid sequence of a chicken VH region taken from the structure of a chicken Fab (PDB 4GLR; [Shih et al., Shih et al. J. Biological Chemistry 287, 44425-44434, 2012]). The heavy chain variable region sequence of the chicken Fab PDB 4GLR is as follows:

```
                                         (SEQ ID NO: 2)
AVTLDESGGGLQTPGGGLSLVCKASGFTLSSYQMMWVRQAPGKGLEWVA

GITSRGGVTGYGSAVKGRATISRDNGQSTVRLQLNNLRAEDTGTYYCAK

PALDSDQCGFPEAGCIDAWGHGTEVTVSS
```

Analysis of the model showed that 24 non-bonded electrostatic interactions are present between the chicken VH and the human VL, whereas only 20 were identified in the fully human template (see FIG. 4a). Of these interactions, 10 are identical between the two structures and 2 are formed between equivalent or homologous residues found at the same positions. Interestingly, more hydrogen bonds (12 instead of 6) are found in the chicken VH-human VL interface compared to the human VH-human VL interface, indicating stable interactions in the chicken VH-cLC interface. Details on the interactions are shown in FIG. 4a.

Figure 4C:
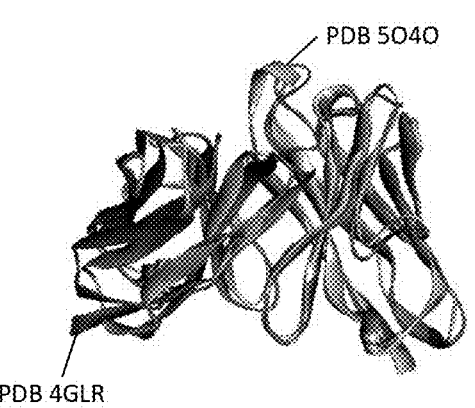

Additionally, a 1338T variation in the chicken VH sequence was introduced (SEQ ID NO: 2). This variation was added to account for the introduction of a BstEII cloning site at the nucleic acid level, which facilitates use of a wild-type immunized chicken heavy chain repertoire and its introduction of nucleic acids encoding those heavy chain variable regions directly into a phage display library, as explained in further detail below. The introduction of the I110T variant, and BstEII cloning site in the nucleic acid keeps the hydrogen bond formed with Q12 (see FIG. 4b). Of note, in the homology model, positions 12 and 110 are in FW1 and FW4 respectively. An overlay of the VL-VH regions of the human and chicken Fabs (PDB 5O4O and 4GLR) is shown in FIG. 4c. The structures, with a root-mean-square deviation (RMSD) of atomic positions of 1.27 Å, are similar with small differences mainly located in the CDRs and loops. Overall the homology model and structural analyses indicate that the folding of the hybrid Fab is similar to that of the human Fab, and evidence a stable interaction between the chicken VH domains and human VL domain, notwithstanding the fact that homology between human VH gene segments and the chicken VH gene segment is low at the primary amino acid level.

In another model based on an energy minimized and side chain minimized crystal structure of a human Fab comprising MF3178 PDB entry 5O4O, the heavy chain region of the chicken Fab PDB 4GLR (Shih et al. J. Biological Chemistry 287, 44425-44434, 2012) having SEQ ID NO: 92 was modeled against a human light chain region having SEQ ID NO: 94; SEQ ID NO: 95; SEQ ID NO: 93; or SEQ ID NO: 96 Results are shown in FIG. 20.

Analysis of the models showed that 31 non-bonded electrostatic interactions are present between the chicken VH-human CH1 and the human VL-CL of SEQ ID NO: 94, where 50 interactions were identified in the fully chicken template and 35 interactions in the fully human template. The chicken VH-human CH1 further has 47 non-bonded electrostatic interactions with the human VL-CL of SEQ ID NO: 95; 45 non-bonded electrostatic interactions with the human VL-CL of SEQ ID NO: 93; and 44 non-bonded electrostatic interactions with the human VL-CL of SEQ ID NO: 96.

This data indicates that the chicken VH region is capable of pairing with several different human VL regions.

Example 2. Chimeric Duck VH-human VL
Antibodies

Upon demonstrating the capacity of directly pairing chicken heavy chain variable regions with a human common light chain, and its capacity to generate an even larger number of stable interactions at the mixed VH-VL interface as compared to the human VH-VL interface, a further bird species, *Anas platyrynchos* (mallard duck), was modelled as described for the chicken VH above.

An amino acid sequence encoded by a duck VH gene segment XP_021132877.1 (SEQ ID NO: 12) is homologous to the amino acid sequence encoded by human VH gene segments as set out in the protein alignment shown in FIG. 8. The human VH gene segments encoding amino acid sequence with highest homology to the amino acid sequence encoded by the duck putative functional VH gene segment are human VH4-59, VH4-61, VH4-39 and VH4-31 which have a 41% amino acid identity as set out in the protein alignment shown in FIG. 9. All sequence comparisons were carried out using the AlignX component of Vector NTI Advance 11.5.2 software, using default settings.

A 3D homology model of a human/duck hybrid Fab was generated (see FIG. 10), based on the crystal structure of a human Fab comprising MF3178 (PDB entry 5O4O; containing a VH1-02 derived gene [Geuijen et al., 2018]), having SEQ ID NO: 1, as described above in Example 1.

In the model, the human VH was replaced by a modeled VH based on the amino acid sequence of a duck VH taken from Genbank accession number A46529. The heavy chain variable region sequence is as follows:

(SEQ ID NO: 3)
AETLDESGGGLVSPGGSLTLVCKGSGFTFSSNEMYWVRQAPGKGLEWVA

GITTGGYTGYAPAVKGRFTISRNNGQSTLTLQMNSLKAEDTATYYCAKI

TGYANCAGYGCAADIDLWGHGTEVTVSS

Analysis of the model showed that 28 non-bonded interactions are present between the duck VH and the human VL interface, whereas only 20 were identified in the fully human template (see FIG. 10a). Of these interactions, 12 are identical between the two structures and 1 is formed between equivalent or homologous residues found at the same positions between the mixed VH-VL interface and the human VH-VL interface. More hydrogen bonds (12 instead of 7) are found in the duck VH-human VL interface compared to the human VH-human VL interface, indicating stable interactions in the duck VH-cLC interface. Details on the interactions are shown in FIG. 10a.

An overlay of the VL-VH regions of the human and duck Fabs is shown in FIG. 10b. The structures, with a root-mean-square deviation (RMSD) of atomic positions of 1.27 Å, are similar with small differences mainly located in the CDRs and loops. Overall the homology model and structural analyses indicates that the folding of the hybrid Fab is similar to the heavy chain for the human MF3178 template, and evidence a stable interaction between the duck VH domains and humanVL domain.

Example 3. Chimeric Ostrich VH-Human VL Antibodies

Chickens and ducks represent biological orders fowl (clade Galloanserae), namely the Galliformes and Anseriformes. Accordingly, the ability of heavy chain variable regions of a non-fowl bird species (which is more distally related to ducks and chickens), namely the ostrich (*Struthio camelus*), to directly pair with a human light chain variable region (which can be used as a common light chain in multivalent multimer formats) was modelled as described for the chicken VH above in Example 1.

An amino acid sequence encoded by an ostrich VH gene segment XP_009669322.1 (SEQ ID NO: 13) is homologous to an amino acid sequence encoded by human VH gene segments as set out in the protein alignment shown in FIG. 5. The human VH gene segments, which encode amino acids having the highest homology to the encoded amino acid of the ostrich VH gene segment are human VH3-73 and VH3-23 which have a 76.5% amino acid identity as set out in the protein alignment shown in FIG. 6. All sequence comparisons were carried out using the AlignX component of Vector NTI Advance 11.5.2 software, using default settings.

A 3D homology model of a human/ostrich hybrid Fab was generated (see FIG. 7), based on the crystal structure of a human Fab comprising MF3178 (PDB entry 5O4O; containing a VH1-02 derived gene [Geuijen et al., 2018]), having SEQ ID NO: 1, as described above in Example 1.

In the model, the human VH was replaced by a modeled VH based on the amino acid sequence of a ostrich VH taken from Genbank accession number AFN02388. The heavy chain variable region sequence is as follows:

(SEQ ID NO: 4)
AVQLVESGGGLQQPGGSLRLSCKGTGFTLSSFGMSWIRQAPGKGLEPVA

GISSSGSDTYYADAVQGRFTISRDNGQSTLYLQMNGLKAEDTATYYCAK

CATDWGSCGPWNLDAWGRGASVTVSS

Analysis of the model showed that 14 non-bonded interactions are present between the ostrich VH and the human VL interface (see FIG. 7a). Of these interactions, 7 are identical between the two structures and 1 is formed between equivalent or homologous residues found at the same positions in the human VH and VL interface. Approximately the same number of hydrogen bonds (6 instead of 7) are found in the ostrich VH-human VL interface compared to the human VH-human VL interface, indicating stable interactions in the ostrich VH-cLC interface. Details on the interactions are shown in FIG. 7a.

Figure 7B:
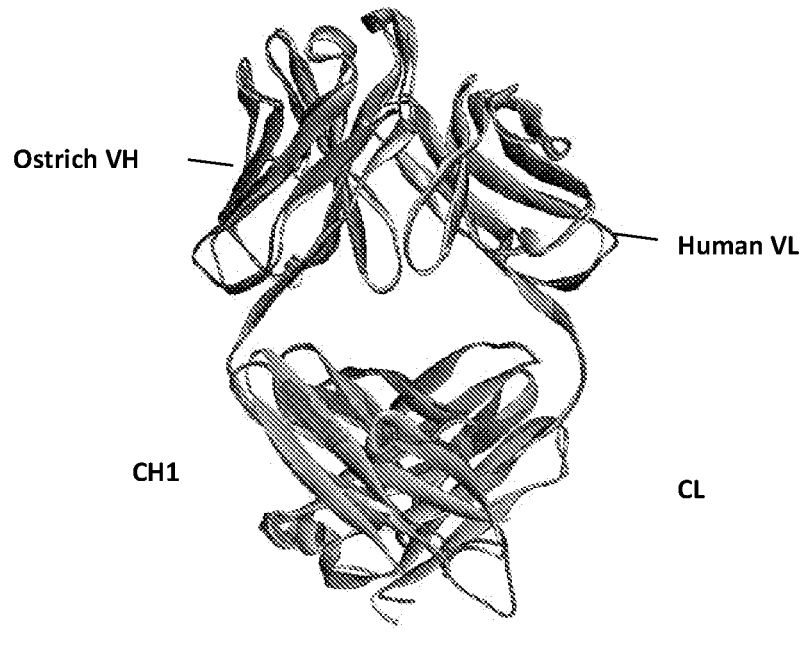
Figure 7C:
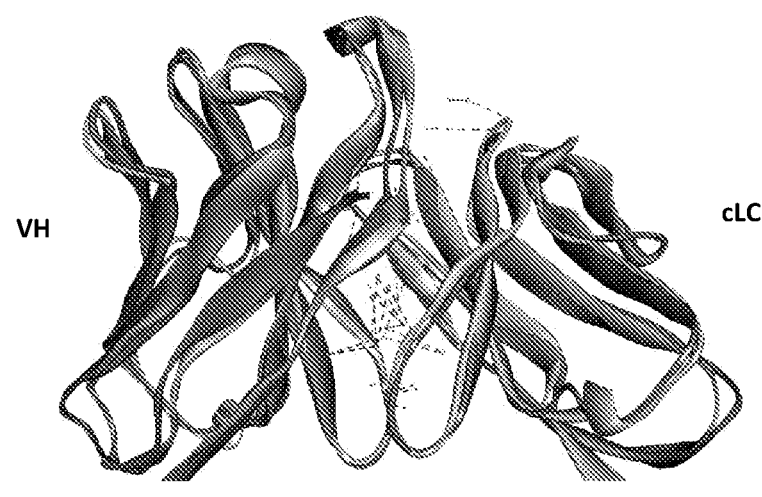

An overlay of the VL-VH regions of the human and ostrich Fabs is shown in FIG. 7b. The structures, with a root-mean-square deviation (RMSD) of atomic positions of 1.27 Å, are similar with small differences mainly located in the CDRs and loops. Overall the homology model and structural analyses indicates that the folding of the hybrid Fab is similar to that of the human Fab, and evidence a stable interaction between the ostrich VH domains and human VL domain, notwithstanding the fact that homology between human VH gene segments and the ostrich VH gene segment is low at the primary amino acid level.

Overall, Examples 1 to 3 demonstrate that a considerable amount of homology at the tertiary structure level exists between chicken and human variable regions, duck and human variable regions and ostrich and human variable regions, even though V gene segments from chicken, duck and ostrich share relatively low homology with human V gene segments at the primary amino acid level. Indeed, duck has lower homology to human V gene segments than chicken at the primary amino acid level, but even more modeled contact points with human cLC (compared to chicken), indicating a higher degree of tertiary structure homology. On the other hand, ostrich has higher homology to human V gene segments than chicken at the primary amino acid level, but fewer modeled contact points with human cLC (compared to chicken). Stable binding domains may thus be formed between rearranged variable regions.

Example 4: Generating Primers for the Introduction of Chicken VH Regions into Vectors for Use in Generating a Phage Display Library or for Introduction into a Host Cell Genomic chicken heavy chain locus sequences of a commercial broiler (CB) inbred line have been published (Reynaud et al., Cell 59, 171-183, 1989), including a fragment containing the single functional VH gene segment (VH1) that has been stored in the NCBI database at accession number M30319 (see FIG. 11), and a fragment containing the single functional JH gene segment (accession number M30320; see FIG. 12).

Since chickens contain only one functional VH gene segment and one functional JH gene segment, a single forward primer and a single reverse primer are sufficient to amplify VH region sequences from immunized chickens.

A forward primer named chVH-FW was designed as follows:

The first 33 bases (GTCCTCGCAACTGCGGCCCAGCCGGC-CATGGCC) of primer chVH-FW are identical to the first 33 bases of the forward primers that are known to amplify human, mouse or rat VH sequences (de Haard et al., *Journal of Biological Chemistry* 274, 18218-18230, 1999). This region encodes part of the leader peptide and contains a SfiI cloning site, as present in the vectors used for phage display.

The last 21 bases (GCCGTGACGTTGGACGAGTCC) of primer chVH-FW are identical to the first 21 bases of the single functional chicken VH gene segment. mRNA-derived VH sequences isolated from chickens usually contain no or very few mutations in this region (see e.g. Reynaud et al., 1989, supra), due to the fact that in this region, VH pseudogenes (which act as donor sequences in VH diversification) are completely or nearly identical to the functional VH gene segment that acts as acceptor. Exactly the same 21 bases have been used in a similar chicken VH amplification forward primer described by others (Andris-Widhopf et al., Journal of Immunological Methods 242, 159-181, 2000).

The total 54-base sequence of primer chVH-FW, with the SfiI site underscored, is:

```
                                    (SEQ ID NO: 15)
5'GTCCTCGCAACTGCGGCCCAGCCGGCCATGGCCGCCGTGACGTTGGA
CGAGTCC-3'
```

The annotated sequence of primer chVH-FW is given in FIG. 13.

The DNA alignment in FIG. 14 shows the homology between primer chVH-FW, part of the functional chicken VH and part of a specific phage display vector MV1511.

To check in silico that combining the leader of vector MV1511 with a chicken VH sequence leads to correct processing, the SignalP tool (http://cbs.dtu.dk/services/SignalP) was used to analyze a protein sequence comprising the MV1511 leader and the chicken VH1. The results indicated predicted cleavage at the expected position.

A reverse primer named chVH-RV was designed as follows:

Phage display vector MV1511 (see FIG. 18) contains BstEII and XhoI cloning sites as part of a sequence encoding the end of a JH that is highly homologous to the corresponding sequence in human, mouse and rat JH. The functional chicken VH contains an internal XhoI site (in FW3—see FIG. 11), so XhoI cannot be used to clone chicken VH. The BstEII site is not present in the chicken VH and this site is therefore incorporated in the reverse primer, which encodes the end of the JH sequence. This is not possible via silent mutations only; incorporation of the BstEII site leads to a single isoleucine to threonine mutation that changes the JH sequence from VIVSS to VTVSS. Based on analysis of VH crystal structures (see above), this variation is predicted to not significantly affect the structural and binding properties of the antibodies. This is an example of a variation to the chicken VH sequence for cloning purposes, as well as for humanization purposes, although persons of ordinary skill in the art understand that additional or different variations, which do not significantly affect the structure of binding of the chicken VH/human VL domain may be incorporated as well.

The sequence of the 24-base primer chVH-RV, with mutations away from the chicken JH gene segment underlined, and with the BstEII site in bold italics, is:

```
                                    (SEQ ID NO: 16)
   5'-GGAGGAGAC***GGTGACC***TCGGTCCC-3'
```

The annotated sequence of the reverse complement of primer chVH-RV is given in FIG. 15.

The DNA alignment in FIG. 16 shows the homology between the reverse complement of chVH-RV, part of the chicken JH and part of vector MV1511. The entire primer is 92% identical (22 of 24 bases) to the corresponding chicken JH sequence; the first 10 bases (on the 5' side) and the last 8 bases (on the 3' side) are 100% identical.

As described in detail in Example 6, the primers chVH-FW and chVH-RV are used to amplify VH regions from chickens immunized with huPD-1, followed by preparation of Fab phage display libraries via cloning the amplified VH regions into vector MV1511 that contains a human CH1 gene and the human cLC. These libraries are used to generate anti-huPD-1 Fab panels as set out in Example 6.

Example 5: Immunization of Wild-Type Chickens with Human PD-1

A suitable expression vector may be generated which incorporates nucleic acid encoding at least a portion of human PD-1 (huPD-1) in order that DNA immunization of a chicken may be carried out.

The nucleic acid encoding for huPD-1 is set out below in SEQ ID NO: 17. However, this sequence may be codon-optimized for expression in a chicken and only a part of the sequence may be used in order that only the extracellular domain of huPD-1 is expressed. A suitable codon-optimized nucleic acid sequence suitable for expression of the extracellular domain is set out in SEQ ID NO: 18.

The expression vector may comprise appropriate control elements, such as a promoter, which are suitable for a driving expression of huPD-1 polypeptide in a chicken following immunization.

```
                                      SEQ ID NO: 17
ATGCAGATCCCACAGGCGCCCTGGCCAGTCGTCTGGGCGGTGCTACAAC

TGGGCTGGCGGCCAGGATGGTTCTTAGACTCCCCAGACAGGCCCTGGAA

CCCCCCCACCTTCTCCCCAGCCCTGCTCGTGGTGACCGAAGGGGACAAC

GCCACCTTCACCTGCAGCTTCTCCAACACATCGGAGAGCTTCGTGCTAA

ACTGGTACCGCATGAGCCCCAGCAACCAGACGGACAAGCTGGCCGCCTT

CCCCGAGGACCGCAGCCAGCCCGGCCAGGACTGCCGCTTCCGTGTCACA

CAACTGCCCAACGGGCGTGACTTCCACATGAGCGTGGTCAGGGCCCGGC

GCAATGACAGCGGCACCTACCTCTGTGGGGCCATCTCCCTGGCCCCCAA

GGCGCAGATCAAAGAGAGCCTGCGGGCAGAGCTCAGGGTGACAGAGAGA

AGGGCAGAAGTGCCCACAGCCCACCCCCAGCCCCTCACCCAGGCCAGCCG

GCCAGTTCCAAACCCTGGTGGTTGGTGTCGTGGGGGGCCTGCTGGGCAG
```

51

-continued

```
CCTGGTGCTGCTAGTCTGGGTCCTGGCCGTCATCTGCTCCCGGGCCGCA

CGAGGGACAATAGGAGCCAGGCGCACCGGCCAGCCCCTGAAGGAGGACC

CCTCAGCCGTGCCTGTGTTCTCTGTGGACTATGGGGAGCTGGATTTCCA

GTGGCGAGAGAAGACCCCGGAGCCCCCCGTGCCCTGTGTCCCTGAGCAG

ACGGAGTATGCCACCATTGTCTTTCCTAGCGGAATGGGCACCTCATCCC

CCGCCCGCAGGGGCTCAGCTGACGGCCCTCGGAGTGCCCAGCCACTGAG

GCCTGAGGATGGACACTGCTCTTGGCCCCTCTGATGA
```

SEQ ID NO: 18

```
GGATCCCCAGGATGGTTCCTGGATAGCCCCGACAGACCATGGAACCCAC

CAACATTCAGCCCCGCTCTGCTGGTGGTTACCGAGGGCGATAACGCCAC

CTTCACATGCAGCTTCAGCAACACCAGCGAGAGCTTCGTGCTGAACTGG

TACAGAATGAGCCCCAGCAACCAGACCGACAAGCTGGCTGCTTTCCCCG

AGGATAGAAGCCAGCCAGGCCAGGACTGCAGATTCAGAGTGACACAGCT

GCCCAACGGCAGAGACTTCCACATGTCTGTTGTGCGCGCCAGAAGAAAC

GACAGCGGCACATATCTGTGCGGCGCGCCATTAGCCTGGCTCCAAAGGCTC

AGATCAAAGAGAGCCTGAGAGCCGAGCTGAGAGTGACAGAGCGCAGAGC

TGAAGTGCCCACAGCTCACCCATCTCCATCTCCAAGACCAGCCGGCCAG

TTCCAGACACTGGTGCTCGAG
```

The huPD-1 expression vector may be prepared for immunization, for example by attachment to a suitable adjuvant. Chickens, typically white leghorn chickens, are then immunized with huPD-1 DNA. Immunization may be intramuscular or may be intradermal (without adjuvant) using a genegun on a weekly basis (days 0, 7, 14 and 21) for 4 consecutive weeks. A suitable amount of DNA, for example 120 pg DNA, may be applied at each immunization point. Thus, a primary immunization may be carried out with two, three, four or more booster immunizations. Immunization of chickens by Genegun is described in, for example, Witkowski et al., J. Immunol. Methods. 2009; 341:146-153.

On day 0, one egg or serum per immunized chicken is collected as a pre-immune sample. Following the third or fourth booster immunization, for example, one egg per chicken per day or serum may be collected for several days. If needed/desired, eggs/serum may be collected after 8 immunizations or even after 12 immunizations.

IgY antibodies may be isolated from yolk of the collected eggs or serum using methods well known to those skilled in the art.

For chickens of which the IgY shows clear huPD-1 reactivity according to, for example, FACS analysis, spleen cells and bone marrow cells may be isolated, i.e. spleen and bone marrow are removed from chickens for which a significant humoral response is observed against the target protein. Cell suspensions are then generated from both spleen and bone marrow cells and subsequently these cells are lysed in Trizol LS Reagent (Thermo Scientific c #10296028) and stored at −80° C. until use, denaturing the protein present, while permitting the extraction of nucleic acid encoding the repertoire of chicken VH or VL regions.

IgY reactivity with huPD-1 may be analyzed using FACS and ELISA. The FACS may include suitable cells transiently transfected with the expression vector encoding huPD-1 as target cells, non-transfected cells as negative control cells, an anti-PD-1 antibody as positive control antibody, and an anti-tetanus toxoid (TT) antibody as negative control. As secondary antibody to detect the human IgG, PE-conjugated goat anti-human IgG (Invitrogen, cat. no. H10104) may be used. As secondary antibody to detect the chicken IgY, PE-conjugated goat anti-Chicken IgY (Jackson ImmunoResearch, cat. no. 103-117-008) may be used.

Example 6: Library Generation from Spleen and Bone Marrow (BM)

In order to generate phage display libraries of chicken VH regions with a human VL region, TRIzol samples from spleen and bone marrow cells of huPD-1 immunized chickens as produced following for instance the protocol described in Example 5 were used to generate individual libraries. The samples were used to isolate RNA and cDNA was then synthesized using an oligo(dT) primer. Multiple reactions may be carried out to generate enough material for subsequent PCR reactions.

The generated cDNA samples were then used as template to amplify and subsequently digest VH genes using the two chicken-specific primers chVH-FW and chVH-RV (see FIGS. 13 to 16 and SEQ ID NO:) essentially as described in Marks et al. (J. Mol. Biol. 222(3), 581-97, 1999).

For each cDNA sample, multiple PCRs may be performed in parallel (all using chVH-FW and chVH-RV) in order to generate sufficient PCR products for the subsequent steps. More than 10 or even more than 20 PCRs might be required.

The procedure is intended to result in at least 20 ng purified digested VH insert for each cDNA sample at a minimal concentration of 3 ng/μl.

Phage display libraries were made according to a plate-based protocol. In summary:

The PCR products were cloned in a phagemid vector for the display of Fab fragments on phage essentially as described in de Haard et al. (J Biol Chem. 1999 Jun. 25; 274(26):18218-30) with the exception that the light chain of SEQ ID NO: 5, which was used for everyFab, is encoded by the vector.

The nucleic acids encoding the VH regions were ligated into SfiI/BstEII-digested vector and the resulting ligated vectors transformed to TG1 cells, which should yield >1E6 cfu (colony-forming units) per library.

Colony PCR may be performed for a subset of clones for each library to determine the VH insert frequency. DNA sequencing may also be performed for a subset of clones per library to determine VH sequence diversity.

Example 7: Fab Validation

For all libraries to be generated, a number of random clones were picked and used to prepare soluble Fabs essentially according to J. Mol. Bio. 222(3), 581-97, 1991 and J. Biol. Chem. 274(26), 18218-30, 1999. Fully human clones are included as reference. This procedure yields non-purified periplasmic extracts containing the soluble Fabs.

To check that the Fabs are produced well and can be bound by Protein L, The ForteBIO Octet-QKe system comprising an Octet instrument that is controlled by Octet software on a separate computer attached to the instrument may be used. The system, based on Bio-Layer Interferometry (BLI), permits real-time quantitation and kinetic characterization of biomolecular interactions and it is used substantially according to the manufacturer's instructions (for details see www.fortebio.com). Quantitation of Fabs is performed using Protein L biosensors (FortéBIO, part. no. 18-5085).

The Fabs were purified from the supernatant using NAb™ Protein L. Spin Kit to allow analysis of the Fabs directly on a SDS-PAGE gel. Concentration of the supernatants and Protein L purified samples were measured.

The concentrations of the non-purified Fabs were in the usual range, around 50 µg/ml. This indicates that a Fab comprising a chicken VH and the human VL results in normal expression levels.

To check protein integrity, the Fabs were subjected to SDS-PAGE and Western blotting using a NuPAGE 4-12% Bis-Tris gel. HRP-labeled mouse antibody that recognizes the CH1 domain of human IgG (Becton Dickinson, cat. no. 555788) is used as the detection antibody. At non-reducing conditions a single band of approximately 50 kD is expected for the intact Fab which demonstrates correct pairing of chicken heavy chain and the human common light chain, whereas a band of approximately 25 kD is expected at reducing conditions for the heavy chain fragment of the Fab.

FIG. 21 shows that the purified chimeric Fabs and the human control Fab of SEQ ID NO: 98 give similar results, indicating correct heavy chain-light chain pairing of the chimeric Fabs. Non-reduced samples of these Fabs contain a band of 25 kD in addition to a band of 50 kD for the intact Fab. The 25 kD size is consistent with unpaired light chains as a result of Protein L. purification. Protein L. purification may change the ratio of intact Fab and non-paired light chains. These results were therefore further confirmed by Western blotting using ProtL-HRP (Ab108) and α-myc (Ab217) for detection. Results are shown in FIG. 23. The chimeric Fabs give similar results as the human control of SEQ ID NO: 98, thereby confirming correct pairing of the heavy and lights chains of the chimeric Fabs. The expected band of 50 kD indicative of intact Fab is present for all Fabs.

Example 8: Selection of PD-1 Fabs from Immunized Chicken Libraries

Phage Display Library Rescue

All libraries generated in Example 6 above are used separately during phage display selections in this Example.

All libraries used in this Example may be rescued by harvesting bacteria after overnight growth and phage may then be prepared according to established protocols (de Haard et al., J. Biol. Chem., 274(26), 18218-30, 1999).

Phage Display Selections

Several different selection strategies (recombinant protein and cell selections, each for huPD-1 and moPD-1) may be implemented to select phage, for example as described in this Example.

For all selection strategies, one round of selection may be performed. If no enrichments are observed, or if the hit-rate during screening is <20%, second round selections may be carried out. Such second round selections may be carried out using the same selection strategies as the first rounds or using a different format. For example, after a first round on huPD-1 recombinant protein, a second round may again be done on huPD-1 recombinant protein, or on moPD-1 recombinant protein, or even on cell-expressed huPD-1 or moPD-1.

Recombinant Protein Panning Selections

Recombinant proteins consisting of huFc fused to PD-1 from several species, as well as biotinylated PD-1 fusion proteins, are listed in Table 1 for use in selection. Panning selections are performed with the KingFisher Flex.

The KingFisher Flex magnetic particle processor is designed for automated transfer and processing of magnetic particles in microplate format. The technology of the King- Fisher Flex system is based on the use of magnetic rods covered with a disposable, specially designed tip comb and plates (see Kontermann R. and Dubel S. (2010) Antibody Engineering Vol. 1, Springer-Verlag Berlin Heidelberg, p 270).

Phage display selections are performed in a semi-automated form using the KingFisher Flex essentially according to the manufacturer's instructions. Two different selection formats are described here: 1) "in solution" selections, i.e. selections on soluble recombinant proteins; and 2) biotinylated cell selections. The antigens are typically biotinylated and captured on streptavidin-coated magnetic beads or magnetic beads coated with an anti-biotin antibody.

Recombinant biotinylated huPD-1 and moPD-1, for example the commercially available huPD-1-huFc-biotin and moPD-1-moFc-biotin (see Table 1, may be used at 5, 0.5 and 0 µg/ml (latter as negative control).

To avoid selection of binders specific for the huFc domain of the recombinant proteins, 100 µg/ml of huIgG (Sigma, cat. no. 4506) is added in solution during library incubation.

Bound phages are eluted using 1 mg/ml trypsin.

The elution samples from the KingFisher are thereafter transferred to rows of a round-bottom 96-well plate containing 5 µl 4 mg/ml AEBSF (Sigma-Aldrich, cat. no. A8456) to inactivate trypsin.

Phage titration by the spot method may be used to determine enrichment/output titers of the selections. Briefly, bacteria are infected with dilution series of the eluted phages, followed by spotting droplets of these on agar plates containing appropriate antibiotics, and after overnight incubation counting the number of colonies, which are representative for the output titer.

TABLE 1

Recombinant PD-1 proteins available for use in selection and ELISA

| Abbreviation | Full name | Supplier | Cat. no. | Concentration (µg/ml) |
|---|---|---|---|---|
| huPD-1-huFc | Recombinant Human PD-1 Fc Chimera Protein, CF | R&D Systems | 1086-PD | selection: 5 ELISA: 2 |
| moPD-1-huFc | Recombinant Mouse PD-1 Fc Chimera Protein, CF | R&D Systems | 1021-PD | selection: 5 |
| huPD-1-huFc-biotin | PD-1 (CD279), Fc fusion, Biotin-labeled (Human) HiP | BPS Bioscience | 71109 | n.a. |
| moPD-1-moFc-biotin | PD-1 (CD279), Fc fusion, Biotin-labeled (Mouse) HiP | BPS Bioscience | 71118 | n.a. |

Cell Selections

Cell selections are performed with the KingFisher essentially according to the manufacturer's instructions, with following remarks/changes:

Selections may be done using FreeStyle 293-F cells that are transiently transfected with an expression vector encoding huPD-1 or moPD-1.

A control FACS to confirm expression of PD-1 using commercial antibodies (see Table 2) may be performed before starting the biotinylation described below.

To detect huPD-1, a mouse antibody that recognizes huPD-1 (Abcam, cat. no. ab52587) may be used as primary antibody, with PE-conjugated goat anti-moIgG (Invitrogen, cat. no. M30004-4) as secondary antibody.

To detect moPD-1, a PE-conjugated rat anti-moPD-1
antibody (ITK-Diagnostics, cat. no. 109103; Merus
Ab0285) may be used.

Cells may be biotinylated using the EZ-Link™ Sulfo-
NHS-Biotin kit (ThermoFisher Cat #21217). This
includes checking the biotinylation efficiency using
FACS with streptavidin-PE (Caltag, cat. no. SA1004-4)
as detection reagent. At the same time, the FACS
described above may again be performed, to confirm
that PD-1 on the cells may still be recognized after the
biotinylation.

Bound phages are eluted using 1 mg/ml trypsin.

The elution samples from the KingFisher are thereafter
transferred to rows of a round-bottom 96-well plate
containing 5 μl 4 mg/ml AEBSF (Sigma-Aldrich, cat.
no. A8456) to inactivate trypsin.

Phage titration by the spot method as described above
may be used to determine enrichment/output titers of
the selections.

TABLE 2

| Commercial antibodies | | | | |
| --- | --- | --- | --- | --- |
| Description | Conjugate | Supplier | Cat. No. | FACS/ELISA concentration |
| Goat anti-moIgG | PE | Invitrogen | M30004-4 | 1:100 |
| Mouse anti-huIgG | HRP | Becton Dickinson | 555788 | 1:2000 |
| Mouse anti-M13 | HRP | Bioconnect | 11973-MM05T-H | 1:5000 |
| Mouse anti-huPD-1 | — | Abcam | ab52587 | 1:200 |
| Rat anti-moPD-1 | PE | ITK-Diagnostics | 109103 | 1:200 |

Screening

Clones are picked randomly and screened as phages.
Screening is carried out by FACS on cell-expressed huPD-1
or moPD-1, since these are the most relevant antigen formats
(screening by ELISA on recombinant PD-1 protein might
result in clones that do not bind cell-expressed PD-1).

Master Plate Picking and Phage Production

From each selection strategy, 24 or 48 clones (depending
on the enrichment observed during selections) are
picked into 96-well master plates (MPs).

As negative control, MF1025 (a phage containing an
anti-thyroglobulin Fab domain) may be inoculated in
one well of each plate.

One well of each MP is left blank (no bacteria), which
is used for adding a positive control antibody during
FACS screening as described below.

Phage Screening Using FACS

Phage FACS is performed using FreeStyle 293-F cells
that are transiently transfected with an expression vector
encoding huPD-1 or moPD-1. One well is used for com-
mercial positive control antibodies (Table 2) to confirm
PD-1 expression: to detect huPD-1, a mouse antibody that
recognizes huPD-1 (Abcam, cat. no. ab52587) may be used
as primary antibody, with PE-conjugated goat anti-moIgG
(Invitrogen, cat. no. M30004-4) as secondary antibody; and
to detect moPD-1, a PE-conjugated rat anti-moPD-1 anti-
body (ITK-Diagnostics, cat. no. 109103) may be used.

Sequencing

The VH genes of all clones that specifically bind to
huPD-1 and/or moPD-1 in FACS are sequenced. Sequences
are analyzed and grouped according to their CDR3
sequence.

Example 9: Generation of a Host Cell Expressing a
Bispecific Chimeric Chicken VH/Human VL
Antibody Bispecific antibodies with at least one chimeric chicken
VH-human VL, can be generated by (transient) transfection
of a plasmid or plasmids encoding a light chain and two
different heavy chains that are CH3 engineered to ensure
efficient hetero-dimerization and formation of the bispecific
antibodies. The production of these chains in a single cell
leads to the favored formation of bispecific antibodies over
the formation of monospecific antibodies.

Thus, nucleic acids encoding two different VHs may be
cloned into suitable expression vectors along with the rear-
ranged huVK1-39 light chain in order that bispecific anti-
bodies may be expressed in a single cell. One or both of the
nucleic acids of the VH regions may be of chicken origin
with the remainder human, e.g., one arm chicken VH-human
VL and the remainder human or two arms chicken VH-
human VL or any other permutation.

In U.S. Ser. No. 13/866,747 (now issued as U.S. Pat. No.
9,248,181), U.S. Ser. No. 14/081,848 (now issued as U.S.
Pat. No. 9,358,286) and PCT/NL2013/050294 (published as
WO2013/157954), incorporated herein by reference, meth-
ods and means are disclosed for producing bispecific anti-
bodies using compatible heterodimerization domains. These
means and methods can also be favorably employed in the
present invention. Specifically, a bispecific antibody of the
invention preferably comprises mutations to produce essen-
tially only bispecific full length IgG molecules. Preferred
mutations are the amino acid substitutions L351K and
T366K (EU numbering) in the first CH3 domain (the 'KK-
variant' heavy chain) and the amino acid substitutions L351
D and L368E in the second domain (the 'DE-variant' heavy
chain), or vice versa. It was previously demonstrated in our
U.S. Pat. Nos. 9,248,181 and 9,358,286 as well as the
WO2013/157954 PCT application that the DE-variant and
KK-variant preferentially pair to form heterodimers (so-
called 'DEKK' bispecific molecules). Homodimerization of
DE-variant heavy chains (DEDE homodimers) hardly
occurs due to repulsion between the charged residues in the
CH3-CH3 interface between identical heavy chains.

Such an approach may be applied to any animal suitable
for use in the invention as described herein.

Example 10: Immunization of Wild-Type Chickens
with Mouse CXCR4

CXCR4 is a chemokine receptor of the GPCR Class A,
subfamily A1. It has 7 transmembrane helices with an
extracellular N-terminus and an intracellular C-terminus.
This topology yields 4 extracellular domains. The mouse
homolog shares 91% overall homology with human
CXCR4, with 67% homology with the extracellular
domains. The chicken homolog shares 82% overall homol-
ogy with human CXCR4, with 48% with the extracellular
domains.

Five chickens were immunized with mouse CXCR4 using
a combination of DNA and lipoparticle immunization. Wild-
type full length sequence mouse CXCR4 (SEQ ID NO: 99)
was synthesized and cloned by Integral Molecular. Validation of the plasmid was performed by flow cytometry of transiently transfected HEK293 and QT6 cells, wherein Mab21651 (R&D Systems) was used for detection.

B cells from blood, bone marrow, and spleen were isolated from the chickens with the highest antibody response. RNA was extracted from the leukocytes, synthesized into DNA and DNA encoding heavy and light chain variable regions amplified by PCR. The amplified VH and VL products were cloned into the MV1511 vector (FIG. 18) and Fab phagemids were produced. DNA was transformed into bacteria to generate phage libraries, wherein the phages express a human light chain with SEQ ID NO: 5.

Figure 25:
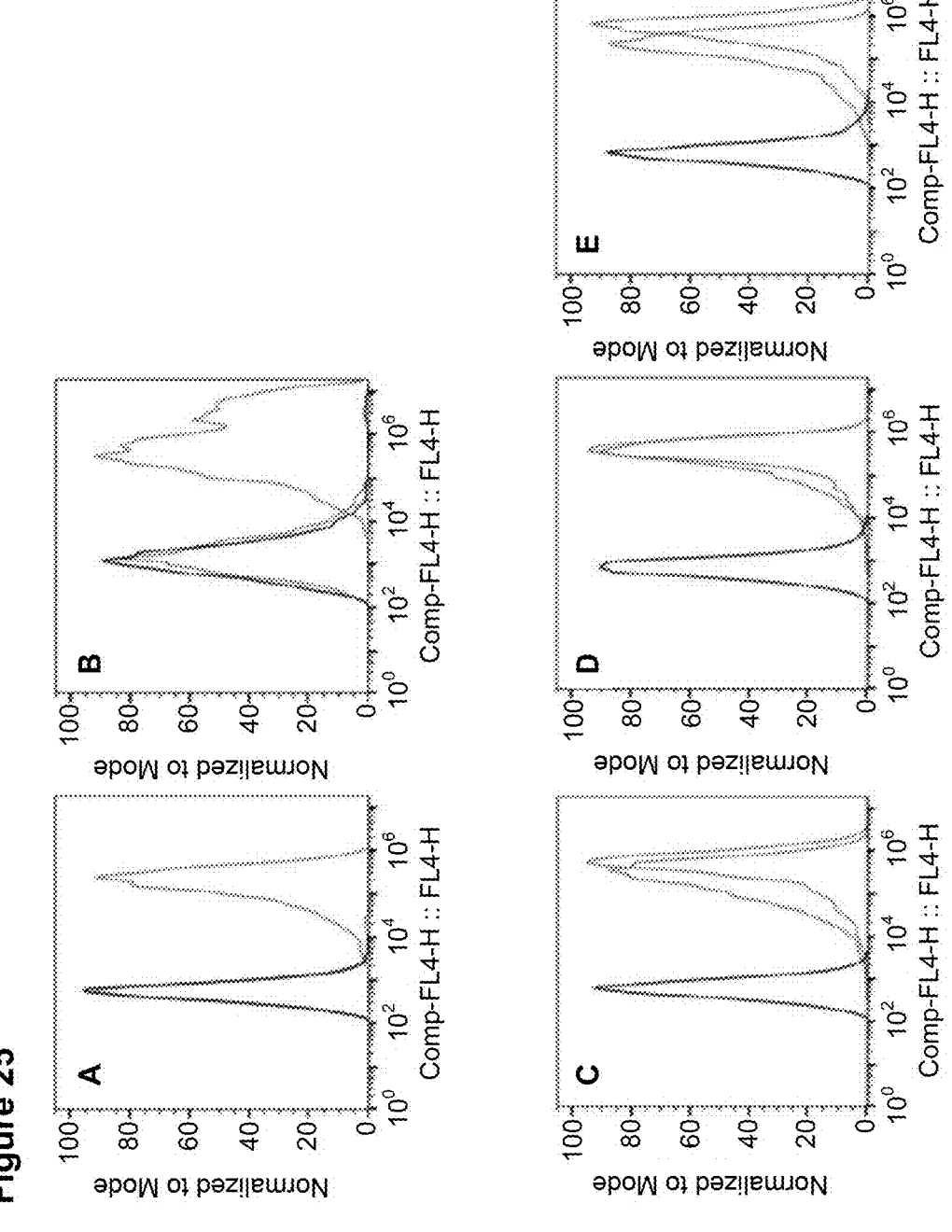

Fab phage libraries were panned on mouse CXCR4 lipoparticles. Clones were screened by lipoparticle ELISA. Binders were sequenced and grouped into families based on CDR3 homology. Fab from three VHCDR3 families were validated by flow cytometry using HEK293 cells expressing natively folded mouse CXCR4. These families were subsequently tested for binding to human CXCR4 by flow cytometry. The positive clones were recloned into IgG format according to standard methods. Three VHCDR3 families were identified that are crossreactive with human and mouse CXCR4. Results are shown in FIG. 25. The amino acid sequences of the heavy chain variable region of the mouse and human CXCR4 binding antibodies are set forth in SEQ Nos: 31, 32 and 33.

Antigen-specific chimeric antibodies comprising a chicken VH and a human VL were generated with functionally paired heavy and light chains.

TABLE 3

| Description of the sequences | |
| --- | --- |
| SEQ ID NO | Description |
| SEQ ID NO: 1 | VH region of MF3178 (PDB 5O4O) |
| SEQ ID NO: 2 | Amino acid sequence of the heavy chain variable region of the chicken Fab region PDB 4GLR |
| SEQ ID NO: 3 | Amino acid sequence of duck VH taken from the structure of amino acids 1 to 133 of Genbank accession no. A46529 |
| SEQ ID NO: 4 | Amino acid sequence of an ostrich VH region taken from the structure of Genbank accession no. AFN02388.1 |
| SEQ ID NO: 5 | Amino acid sequence of human kappa light chain IgVκ1-39*01/IGJκ1*01 |
| SEQ ID NO: 6 | Nucleic acid sequence of common light chain variable region—IGKV1-39/jk1 |
| SEQ ID NO: 7 | Amino acid sequence of common light chain variable region—IGKV1-39/jk1 |
| SEQ ID NO: 8 | Nucleic acid sequence of common light chain constant region |
| SEQ ID NO: 9 | Amino acid sequence of common light chain constant region |
| SEQ ID NO: 10 | Amino acid sequence of common light chain variable domain—IGKV1-39/jk5 |
| SEQ ID NO: 11 | Amino acid sequence of common light chain variable domain V gene segment—IGKV1-39 |
| SEQ ID NO: 12 | Amino acid sequences encoded by one putative functional duck VH gene segment XP_021132877.1 |
| SEQ ID NO: 13 | Amino acid sequences encoded by the ostrich VH gene segment XP_009669322.1 |
| SEQ ID NO: 14 | Amino acid sequence of chicken VH1 gene segment M30319 (FIG. 1) |
| SEQ ID NO: 15 | Nucleic acid sequence of chVH-FW primer |
| SEQ ID NO: 16 | Nucleic acid sequence of chVH-RV primer |
| SEQ ID NO: 17 | Nucleic acid sequence encoding full length of human PD-1 |
| SEQ ID NO: 18 | Nucleic acid encoding extracellular domain of huPD-1 (codon optimized for chicken expression) |
| SEQ ID NO: 87 | Amino acid sequence of common light chain variable region IgVκ3-15/IGJκ1 |
| SEQ ID NO: 88 | Amino acid sequence of common light chain variable region IgVκ3-20/IGJκ1 |
| SEQ ID NO: 89 | Amino acid sequence of common light chain variable region IgVλ3-21/IGJλ1 |
| SEQ ID NO: 90 | Variable gene region sequence IgVκ3-15 |
| SEQ ID NO: 91 | Variable gene region sequence IgVκ3-20 |
| SEQ ID NO: 92 | Amino acid sequence of the heavy chain variable region of the chicken Fab region PDB 4GLR and a human constant region CH1 |
| SEQ ID NO: 93 | Amino acid sequence of human kappa light chain IgVκ1-39/IGJκ5/CK |
| SEQ ID NO: 94 | Amino acid sequence of human kappa light chain IgVκ3-15/IGJκ1/CK |
| SEQ ID NO: 95 | Amino acid sequence of human kappa light chain IgVκ3-20/IGJκ1/CK |
| SEQ ID NO: 96 | Amino acid sequence of human lambda light chain IgVλ3-21/IGJλ3/CA |
| SEQ ID NO: 97 | Variable gene region sequence IgVλ3-21 |
| SEQ ID NO: 98 | Human control Fab |
| SEQ ID NO: 99 | Wild Type full length sequence mouse CXCR4 |
| SEQ ID NO: 100 | VH region of CXCR4-1 |
| SEQ ID NO: 101 | VH region of CXCR4-2 |
| SEQ ID NO: 102 | VH region of CXCR4-3 |

The invention claimed is:

1. A phage which comprises in its genome:
   a nucleic acid encoding a bird heavy chain variable region (VH) and
   a nucleic acid encoding a human common light chain variable region (VL).

2. A phage display library comprising the phage according to claim 1.

3. A method for preparing a phage display library comprising:
   immunizing a bird with an antigen;
   isolating a plurality of nucleic acids encoding heavy chain variable regions from said bird; and
   preparing a phage display library using said nucleic acids encoding said heavy chain variable regions and nucleic acids encoding human light chain variable regions that pair with said heavy chain variable regions,
   thereby preparing a phage display library.

4. The method according to claim 3, wherein the nucleic acids encoding light chain variable regions encode a human common light chain variable region.

5. A method for the identification of a binding domain or a multimer or a variant thereof that has binding specificity for an antigen, which method comprises:
   immunizing a bird with an antigen;
   isolating a plurality of nucleic acids encoding heavy chain variable regions from said bird;
   preparing a phage display library using said nucleic acids encoding said heavy chain variable regions, wherein said phage display library comprises phages comprising a nucleic acid sequence encoding a human common light chain variable region; and
   identifying a phage in the phage display library that binds to the antigen, thereby identifying a binding domain or a multimer or a variant thereof that has binding specificity for the antigen.

6. The phage according to claim 1, wherein the nucleic acids encode a binding domain, or a multimer or a variant thereof, comprising the bird VH that is paired with the VL.

7. The phage according to claim 6, wherein the binding domain is a Fab.

8. The phage according to claim 7, wherein the Fab comprises a CH1 and a VH region paired with a constant light chain (CL) region and a VL region.

9. The phage according to claim 8, wherein the CH1 and CL regions are human.

10. The phage according to claim 8, wherein the CH1 and CL regions are of a bird.

11. The phage according to claim 8, wherein the CH1 is of a bird and the CL region is human.

12. The phage according to claim 6, wherein the bird heavy chain variable region comprises at least 5 electrostatic interactions with the human VL region at the VH/VL interface.

13. The phage according to claim 1, wherein the bird is a Galliform, a chicken, a turkey, a grouse, a New World quail, an Old World quail, a ptarmigan, a partridge, a pheasant, a junglefowl, a bird of the family Cracidae, a goose swan, a duck or an ostrich.

14. The phage according to claim 13, wherein the bird is a chicken, a duck or an ostrich.

15. The phage according to claim 6, wherein the bird heavy chain variable region comprises an amino acid sequence comprising SEQ ID NO: 100; SEQ ID NO: 101 or SEQ ID NO: 102.

16. The phage according to claim 1, wherein the human light chain variable region is a human germline light chain variable region (VL) or a human light chain variable region selected from IgVκ1-39/IGJκ1, IgVκ1-39/IGJκ5, IgVκ3-15/IGJκ1, IgVκ3-20/IGJκ1, or IgVλ3-21/IGJλ3.

17. The method according to claim 5, wherein the binding domain or the multimer is an antibody.

18. The method according to claim 17, wherein the antibody is a bispecific antibody.

19. The method according to claim 17, wherein the antibody is a multispecific or a trispecific antibody.

20. The method according to claim 5, wherein the binding domain or the multimer is subjected to humanization.

21. The method according to claim 5, wherein the bird is a Galliform, a chicken, a turkey, a grouse, a New World quail, an Old World quail, a ptarmigan, a partridge, a pheasant, a junglefowl, a bird of the family Cracidae, a goose swan, a duck or an ostrich.

22. The method according to claim 21, wherein the bird is a chicken, a duck or an ostrich.

23. The method according to claim 21, wherein the human common light chain variable region is a human germline light chain variable region (VL) or a human light chain variable region selected from IgVκ1-39/IGJκ1, IgVκ1-39/IGJκ5, IgVκ3-15/IGJκ1, IgVκ3-20/IGJκ1, or IgVλ3-21/IGJλ3.

* * * * *